US012617848B2

(12) United States Patent
Mao et al.

(10) Patent No.: US 12,617,848 B2
(45) Date of Patent: *May 5, 2026

(54) METHODS OF TREATING OCULAR PATHOLOGIES USING BIFUNCTIONAL MOLECULES THAT TARGET GROWTH FACTORS

(71) Applicant: UNIVERSITY OF MARYLAND, BALTIMORE, Baltimore, MD (US)

(72) Inventors: Li Mao, Pasadena, MD (US); Hening Ren, Highland, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1214 days.

This patent is subject to a terminal disclaimer.

(21) Appl. No.: 17/453,981

(22) Filed: Nov. 8, 2021

(65) Prior Publication Data

US 2022/0056120 A1 Feb. 24, 2022

Related U.S. Application Data

(63) Continuation-in-part of application No. 16/325,764, filed as application No. PCT/US2017/046934 on Aug. 15, 2017, now Pat. No. 11,186,632.

(60) Provisional application No. 62/375,894, filed on Aug. 16, 2016.

(51) Int. Cl.
*C07K 16/22* (2006.01)
*A61K 39/00* (2006.01)
*A61P 27/02* (2006.01)

(52) U.S. Cl.
CPC .............. *C07K 16/22* (2013.01); *A61P 27/02* (2018.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 2003/0190708 A1 | 10/2003 | Burgess |
| 2007/0037748 A1 | 2/2007 | Stahl |
| 2007/0243191 A1 | 10/2007 | Mao et al. |
| 2014/0213769 A1 | 7/2014 | Hong |
| 2020/0071392 A1 | 3/2020 | Mao |

FOREIGN PATENT DOCUMENTS

| | | |
|---|---|---|
| WO | 2015046783 | 4/2015 |
| WO | 2015153514 | 10/2015 |
| WO | 2015153974 | 10/2015 |
| WO | 2016007775 | 1/2016 |

OTHER PUBLICATIONS

Communication pursuant to Article 94(3) EPC; EPO Appln 17 841 989.1-1111, daled Apr. 19, 2024, 6 pages.
International Preliminary Report on Patentability received for PCT Patent Application No. PCT/US2017/046934, mailed on Feb. 28, 2019, 10 pages.
International Search Report and Written Opinion, International Patent Application No. PCT/US2017/046934, mailed Feb. 14, 2018.
Shen, et al., A bi-functional antibody-receptor domain fusion protein simultaneously targeting IGF-IR and VEGF for degradation, MAbs 2015, 7(5): 931-945; Abstract, pp. 933, Fig 1 and its legend.
Zhao, et al. Anti-HDGF targets cancer and cancer stromal stem cells resistant to chemothreapy. Clin Cancer Res. 2013, 19(13); 3567-76; Abstract, p. 3568, col. 2; p. 3570, col. 1.
Zhang, et al., Suppression of tumor growth and metastasis by simultaneously blocking vascular endothelial growth factor (VEGF)-A and VEGF-C with a receptor-immunoglobulin fusion protein. Cancer Res. 2010, 70(6); 2495-503; Abstract, p. 2495, col. 2.
Zhang et al., Down-regulation of hepatoma-derived growth factor inhibits anchorage-independent growth and invasion of non-small cell lung cancer cells, Cancer research, 2006, pp. 18-23, vol. 66.
Thirant et al., Differential proteomic analysis of human glioblastoma and neural stem cells reveals HDGF as a novel angiogenic secreted factor, Stem cells, 2012, pp. 845-853, vol. 30.
Ren et al., Expression of hepatoma-derived growth factor is a strong prognostic predictor for patients with early-stage non-small-cell lung cancer, Journal of clinical oncology, 2004, pp. 3230-3237, vol. 22.
Iwasaki, et al., Hepatoma-derived growth factor as a prognostic marker in completely resected non-small-cell lung cancer, Oncology reports, 2005, pp. 1075-1080, vol. 13 (6).
Ren et al., Antibodies targeting hepatoma-derived growth factor as a novel strategy in treating lung cancer, Molecular cancer therapeutics, 2009, pp. 1106-1112, vol. 8.
Zhang et al., Development and clinical evaluation of a multi-purpose mAb and a sandwich Elisa test for hepatoma-derived growth factor in lung cancer patients, Journal of immunological methods, 2010, pp. 61-67, vol. 355.
Narron et al., Hepatoma-derived growth factor is expressed after vascular injury in the rat and stimulates smooth muscle cell migration, Pediatric research, 2006, pp. 778-783, vol. 59.
Leblanc et al., The regulatory role of hepatoma-derived growth factor as an angiogenic factor in the eye, Molecular Vision, 2016, pp. 374-386, vol. 22.

(Continued)

*Primary Examiner* — Marianne P Allen
(74) *Attorney, Agent, or Firm* — Wolter Van Dyke Davis, PLLC; Eugene J. Molinelli; Martha Cassidy

(57) ABSTRACT

This invention relates to pharmaceutical compositions and methods for treatment of ophthalmic or ocular diseases and conditions. The compositions contain targeting molecules that are made up of a bifunctional hepatoma-derived growth factor-specific antibody covalently attached to a trapper that specifically binds vascular endothelial growth factor and/or transforming growth factor beta. Specific eye conditions that can be beneficially affected by the compositions and methods of the invention include age-related macular degeneration, diabetic retinopathy, peripheral vitreoretinopathy, and retinal vein occlusion.

5 Claims, 18 Drawing Sheets

Specification includes a Sequence Listing.

(56) References Cited

OTHER PUBLICATIONS

Everett et al., Hepatoma-derived growth factor is a pulmonary endothelial cell-expressed angiogenic factor, American journal of physiology lung cellular and molecular physiology, 2004, pp. L1194-201, vol. 286.

Ooi et al., Hepatoma-derived growth factor and its role in keloid pathogenesis, Journal of cellular and molecular medicine, 2010, pp. 1328-1337, vol. 14.

Greenhalgh et al., Healing scars: targeting pericytes to treat fibrosis, Q J Med, 2015, pp. 3-7, vol. 108.

Voelkel et al., The role of vascular endothelial growth factor in pulmonary arterial hypertension. The angiogenesis paradoxiwa, American journal of respiratory cell and molecular biology, 2014, pp. 474-484, vol. 51.

Yang et al., Hepatoma Derived Growth Factor Predicts Disease Severity and Survival in Pulmonary Artery Hypertension, American journal of respiratory and critical care medicine, 2016, pp. 1264-1272, vol. 194.

Extended European Search Report, European Patent Application No. 17841989.1, mailed Feb. 21, 2020, pp. 1-16.

Lee et al., Simultaneous blockade of VEGF and DII4 by HD105, a bispecific antibody, inhibits tumor progression and angiogenesis, mAbs, 2016, pp. 892-904, vol. 8.

Neal et al., Aflibercept in lung cancer, Expert opinion Biol. Ther., 2013, pp. 115-120, vol. 13.

Kou et al., A bispecific antibody effectively inhibits tumor growth and metastasis by simultaneous blocking vascular endothelial growth factor A and osteopontin, Cancer Letters, 2010, pp. 130-136, vol. 299.

Husain et al., Expanding the Boundaries of Biotherapeutics with Bispecific Antibodies, BioDrugs, 2018, pp. 441-464, vol. 32.

Shibuya, M., "VEGFR and Type-V RTK Activation and Signaling," Cold Spring Harbor Laboratory Press, 2013, pp. 1-14.

John C. Zwaagstra, et al.; "Engineering and Therapeutic Application of Single-Chain Bivalent TGF-B Family Traps"; American Association for Cancer Research, Molecular Cancer Therapeutics 2012; 11:1477-1487.

NCBI Reference Sequence: NP_002253.2, Natural Killer Cells Antigen CD94 isoform 1(*Homo Sapiens*), Jul. 4, 2020, accessed Aug. 4, 2020.

FIG. 1

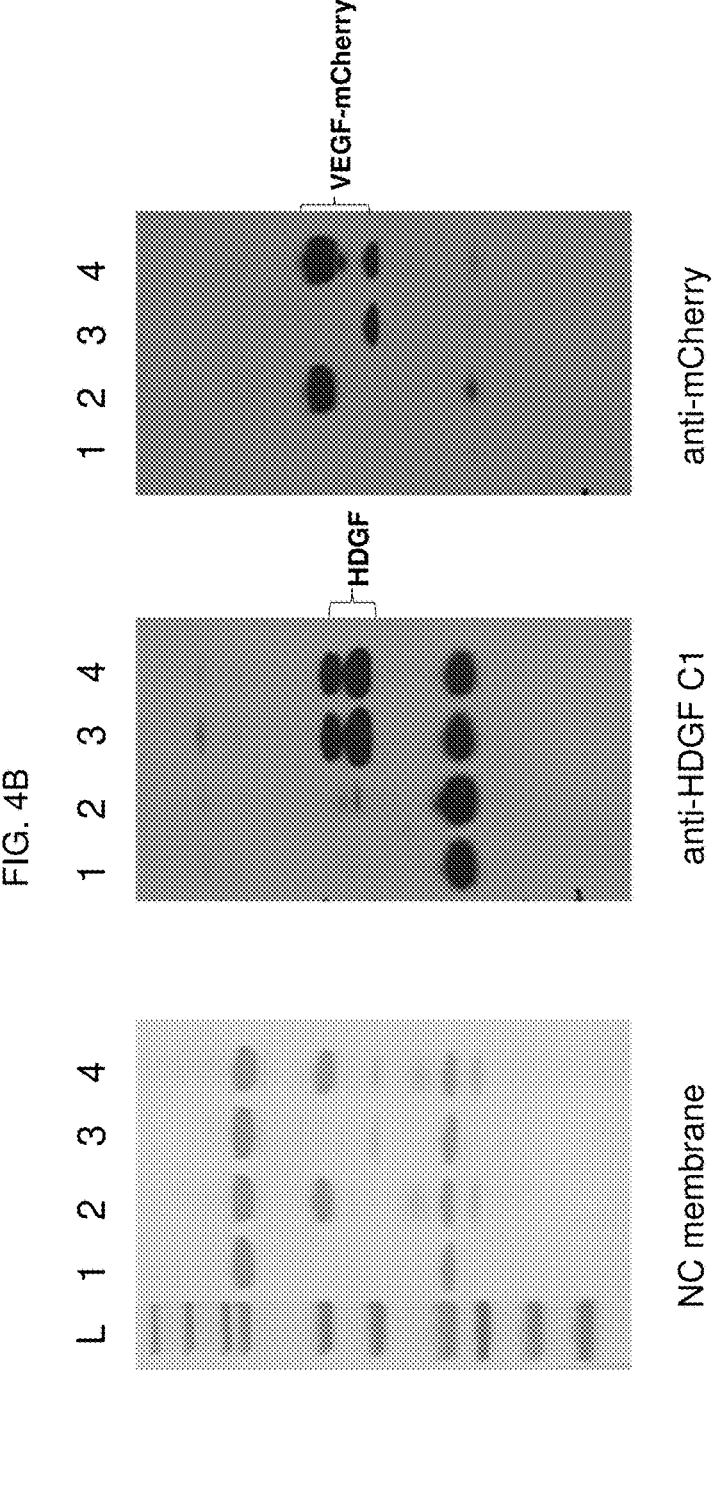

FIG. 5

Reorganization of native
and post-transcriptionally
modified HDGF by
various antibodies.

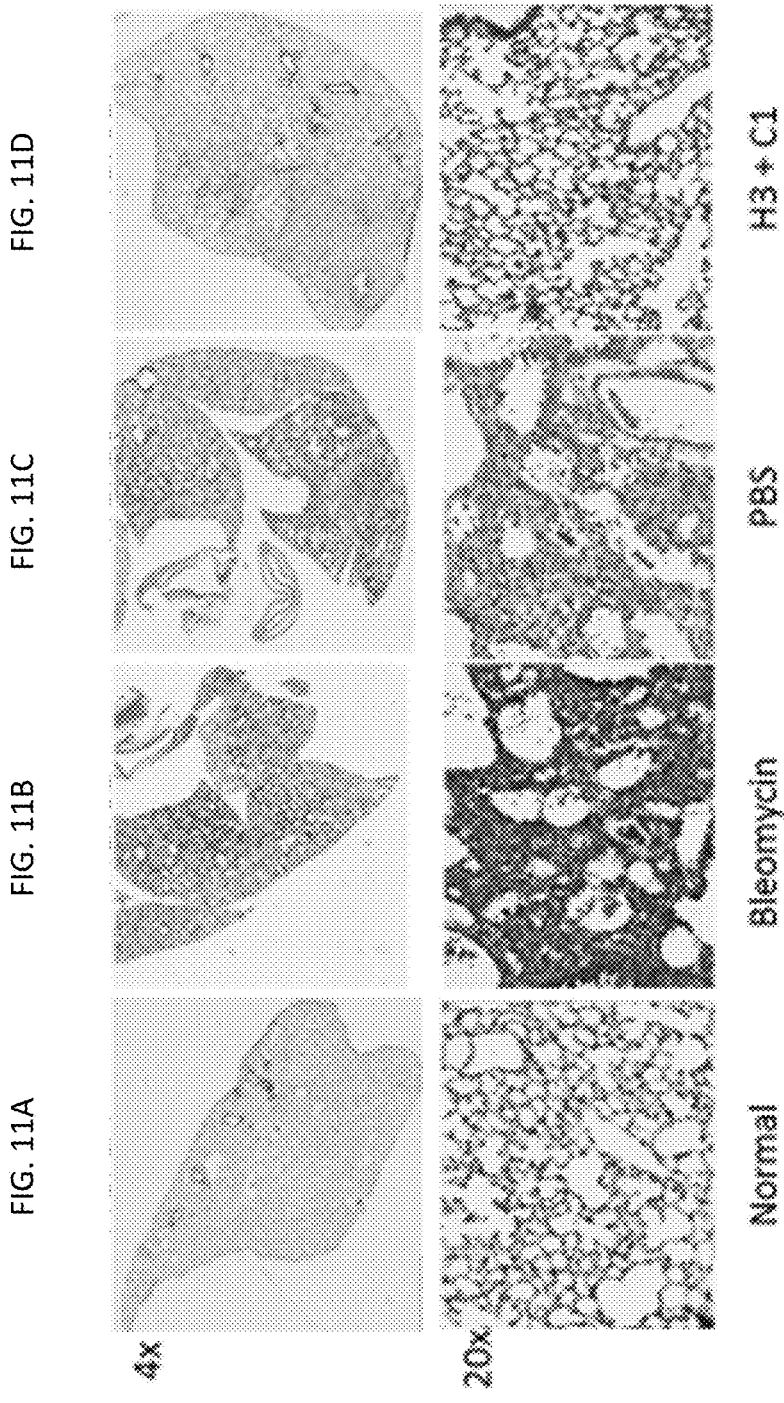

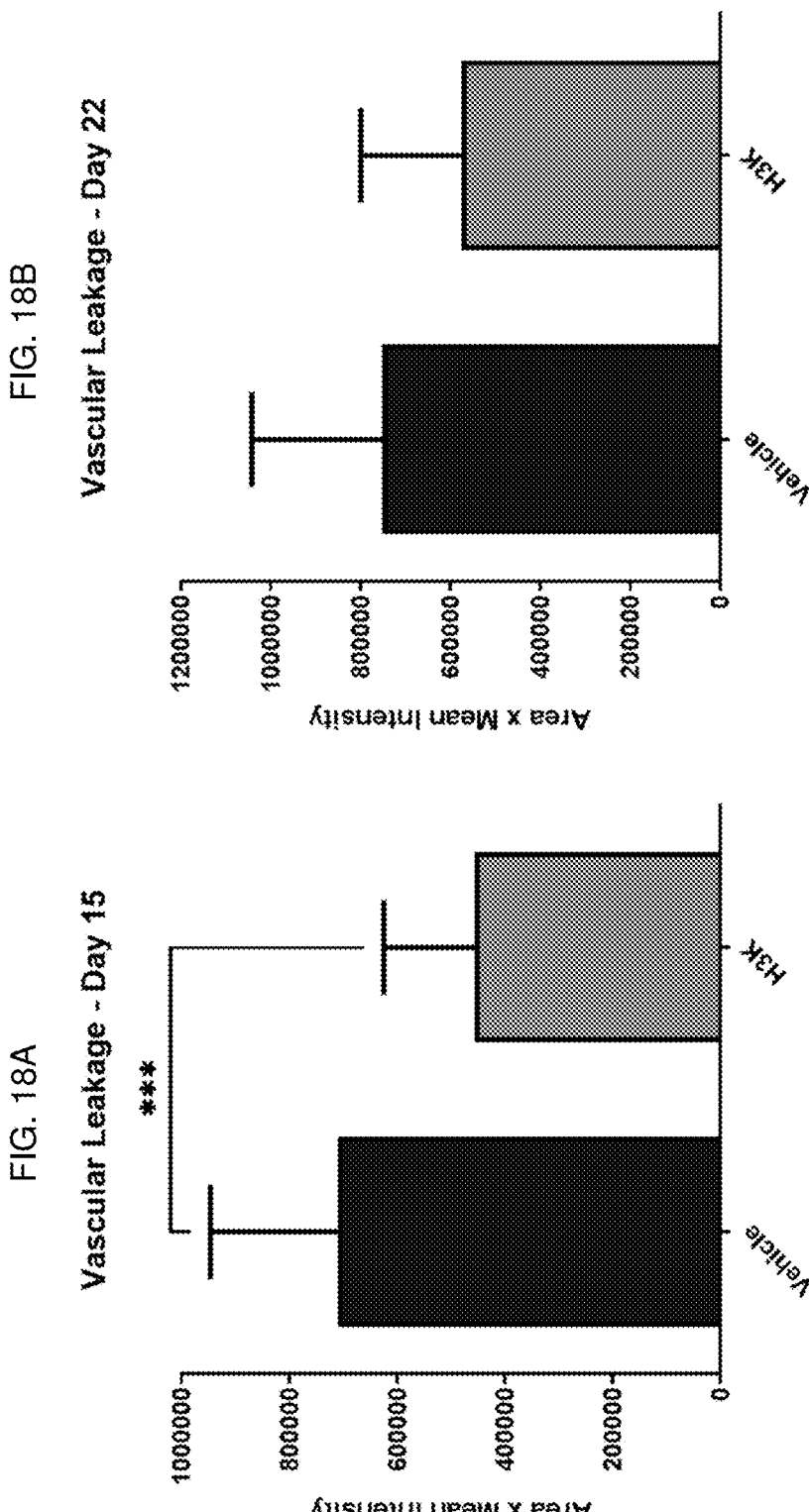

METHODS OF TREATING OCULAR PATHOLOGIES USING BIFUNCTIONAL MOLECULES THAT TARGET GROWTH FACTORS

CROSS-REFERENCE TO RELATED APPLICATIONS

This application is a continuation-in-part of Ser. No. 16/325,764 filed Feb. 15, 2019, which is a 371 national stage application of PCT Application No. PCT/US2017/046934, filed Aug. 15, 2017, and claims benefit of Provisional Application No. 62/375,894, filed Aug. 16, 2016, the entire contents of each of which are hereby incorporated by reference as if fully set forth herein, under 35 U.S.C. § 119(e).

REFERENCE TO SEQUENCE LISTING SUBMITTED VIA EFS-WEB

This application includes an electronically submitted sequence listing in .txt format. The .txt file contains a sequence listing entitled "2021-06-15_15024-342US1_ST25.txt" created on Jun. 15, 2021 and is 60,512 bytes in size. The sequence listing contained in this .txt file is part of the specification and is hereby incorporated by reference herein in its entirety.

BACKGROUND

1. Field of the Invention

The invention relates to the field of medicine and pharmacology. In particular, the invention relates to an ophthalmic pharmaceutical composition including a bifunctional hepatoma-derived growth factor (HDGF)-vascular endothelial growth factor (VEGF) trapper antibody-based targeting protein, and a method for using this composition and a method for treating ophthalmic pathologies such as diabetic retinopathy, age-related macular degeneration, neovasular age-related macular degeneration, peripheral vitreoretinopathy, retinal vein occlusion, and the like.

2. Background of the Invention

Lung diseases including lung cancer and pulmonary fibrosis (PF) are a leading cause of death worldwide. PF is one of a family of related diseases called interstitial lung diseases that can result in lung scarring. As the lung tissue becomes scarred, it interferes with a person's ability to breathe. Hyperproliferation of cells (e.g., fibroblasts or cancer cells) can cause various types of medical conditions (i.e., hyperproliferative conditions) such as keloids, idiopathic pulmonary fibrosis, and lung cancer. Keloids are a type of abnormally formed scar which is composed mainly of collagen as a result of an overgrowth of fibroblasts during wound healing. While keloid scars are benign and not contagious, it may be accompanied by severe itchiness, pain, and changes in skin texture. On the other hand, interstitial lung diseases, particularly idiopathic pulmonary fibrosis, are life threatening and have no cure currently.

Hepatoma-derived growth factor (HDGF) is a heparin-binding growth factor identified from media conditioned by a human hepatoma-derived cell line. It produces mitogenic activity in various cells types. Normally, HDGF is highly expressed during embryonic development in smooth muscle, gut, and endothelium, but not after birth. It has also been implicated in angiogenesis. High-level HDGF is observed in various human cancers. Specifically, HDGF is overexpressed in lung cancer and is a novel mitogenic growth factor for fibroblasts, vascular endothelial cells, and smooth muscle cells. High HDGF expression can also be found in keloid scar tissues but not in normal scar tissue. The molecular mechanisms of HDGF in cancer progression are poorly understood but we have demonstrated that lung cancer cells with down-regulated HDGF formed significantly smaller tumors in vivo (Zhang J., et al., "Down-regulation of hepatoma-derived growth factor inhibits anchorage-independent growth and invasion of non-small cell lung cancer cells," Cancer Res 2006; 66:18-23). Diseases of the lung remain difficult to treat effectively. Therefore, a novel strategy to prevent and treat diseases due to abnormal proliferation of cells (i.e., fibroblasts, cancer cells) is needed.

Ophthalmic conditions and diseases of the eye have a serious impact on life and livelihood of a great number of people. Ophthalmic conditions or pathologies include age-related macular degeneration, neovascular age-related macular degeneration, diabetic retinopathy, peripheral vitreoretinopathy, retinal vein occlusion (sometimes associated with neovascular glaucoma), and retinopathy of prematurity.

Macular degeneration typically occurs in older people due to damage to the macula of the retina. The disease is divided into early, intermediate, and late types. Late macular degeneration also can occur in "wet" and, more commonly, "dry" form. This condition affects more than 190 million people. Current therapy for neovascular age-related macular generation (wet age-related macular degeneration) mainly relies on anti-VEGF-based therapy, includes ranibizumab (Lucentis™), a monoclonal antibody Fab fragment that binds VEGF, for intraocular use (a monthly intravitreal injection) and the older and less effective treatment of photodynamic therapy with verteporfin. Ranibizumab only stabilizes the condition and must be administered monthly by injection into the eye at high cost. An off-label alternative at lower cost is bevacizumab (Avastin™), which has not been subject to a randomized controlled clinical trial for FDA clearance for ocular use. Anti-VEGF treatment with Eylea™ have been suggested as well.

Diabetic retinopathy is a condition of damage to the retina due to diabetes mellitus and is found in up to 80% of long-term diabetes patients. The condition is managed to reduce vision loss by laser surgery, vitrectomy, or injection of corticosteroids or anti-VEGF agents into the eye. These methods do not cure the disease, however.

Retinal vein occlusion, or central retinal vein occlusion, occurs when the central retinal vein blocked by thrombosis, leading to severe damage to the retina and consequent blindness due to ischemia. Treatment for retinal vein occlusion consists of anti-VEGF drugs (e.g., Lucentis) or intravitreal steroid implant and pan-retinal laser photocoagulation.

Proliferative vitreoretinopathy (PVR), formerly named "massive vitreous retraction" and "massive periretinal proliferation." describes the abberant process whereby epi/subretinal membranes form following rhematogenous retinal detachment (RRD), ultimately leading to retinal traction and recurrent retinal detachment. Intraretinal PVR is caused by glial tissue that is activated to proliferate within the retina and can cause retinal shortening. PVR arises in an estimated 5-10% of RRD cases, and therefore represents a major complication of retinal detachment.

Retinopathy of prematurity (ROP) occurs in premature neonates. Normally, the retina becomes completely vascularized at full term. In the premature baby, the retina remains incompletely vascularized at the time of birth. Rather than continuing in a normal fashion, vasculogenesis in the premature neonatal retina becomes disrupted. Abnormal new proliferating vessels develop at the juncture of vascularized and avascular retina. These abnormal new vessels grow from the retina into the vitreous, resulting in hemorrhage and tractional detachment of the retina.

New and different treatments for these ophthalmic conditions are needed in the art.

SUMMARY OF THE INVENTION

It has been discovered that various ocular pathologies can be treated with a single bi-functional chimeric antibody which simultaneously targets HDGF and other over-produced angiogenic factors (i.e., VEGF) in tissue that is damaged, scarred, or cancerous. The simultaneous targeting of these growth factors using a single molecule allows for easier administration and improved efficacy.

Therefore, embodiments of the invention include methods of treating ocular pathologies, including fibrosis, macular degeneration, and especially neovascular age-related macular degeneration. In particular, embodiments of the invention relate to an ophthalmic pharmaceutical composition comprising a bifunctional hepatoma-derived growth factor (HDGF)-vascular endothelial growth factor (VEGF) trapper antibody-based targeting protein and a pharmaceutically acceptable carrier for ophthalmic use, wherein the targeting protein comprises an HDGF-binding antibody binding site, and (a) a receptor domain which specifically binds to vascular endothelial growth factor (VEGF); or (b) or both (a) and a receptor domain which specifically binds to transforming growth factor beta (TGFβ).

In certain preferred embodiments, the VEGF is selected from the group consisting of VEGF-A, VEGF-B, and VEGF-C. In certain other preferred embodiments. TGFβ is selected from the group consisting of TGFβ subtype 1, TGFβ subtype 2, and TGFβ subtype 3.

In some embodiments, the targeting protein comprises both a receptor domain which specifically binds to VEGF and a receptor domain which specifically binds to TGFβ.

Preferably, the antibody binding sites comprise CDRs selected from mouse, human, rabbit, or rat CDRs, most preferably one or more mouse CDRs. In addition, the antibody preferably is humanized or chimeric.

In most preferred embodiments, the targeting protein is H3K. In most preferred embodiments, the targeting protein comprises two antibody heavy chains of SEQ ID NO: 4 and two antibody light chains of SEQ ID NO: 18.

The invention also relates, in certain embodiments, to a pharmaceutical composition comprising the targeting protein as described above and a pharmaceutically acceptable vehicle. Preferably, the vehicle is pharmaceutically acceptable for ophthalmic use via intraocular injection. Preferably the ophthalmic use is intraocular administration or topical ophthalmic administration.

Optionally, pharmaceutical compositions according to embodiments of the invention can further comprise an additional ophthalmic active agent.

Most preferred dosing of the pharmaceutical compositions according to embodiments of the invention contain about 2 mg of the targeting protein.

Additional embodiments of the invention relate to a method of treating an ophthalmic pathology comprising administering the pharmaceutical compositions and targeting proteins discussed herein. In preferred embodiments, the pharmaceutical composition or targeting protein down-regulates HDGF and VEGF expression, HDGF and TGFβ expression, or HDGF, VEGF and TGFβ expression, and is effective to reduce the growth of hyperproliferative cells. The hyperproliferative cells preferably are vascular endothelial cells or a vascular smooth muscle cells.

In preferred embodiments, the patient suffers from an ophthalmic pathology, which can be selected from the group consisting of diabetic retinopathy, age-related macular degeneration, neovasular age-related macular degeneration, peripheral vitreoretinopathy, retinal vein occlusion, or a combination thereof.

BRIEF SUMMARY OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1 is a schematic diagram illustrating an example bi-functional chimeric antibody-based targeting protein (hc-H3-V-T-traps) specific embodiments of which are referred to as H3K or H3T.

FIG. 4A is a photograph of an SDS PAGE gel, stained with Coomassie Blue.

FIG. 4B is a set of SDS-PAGE co-immunoprecipitation assays.

FIG. 5 is a schematic diagram of a vector for recombinant antibody expression in mammalian cells (expression cassette of pLVBHN).

5 ug each (H3+C1, squares); and (3) anti-HDGF H3 250 μg plus Avastin 100 μg (H3+A, triangles). The treatments were given every 3 days thereafter for a total 6 doses, and animals were monitored daily.

Figure 9:
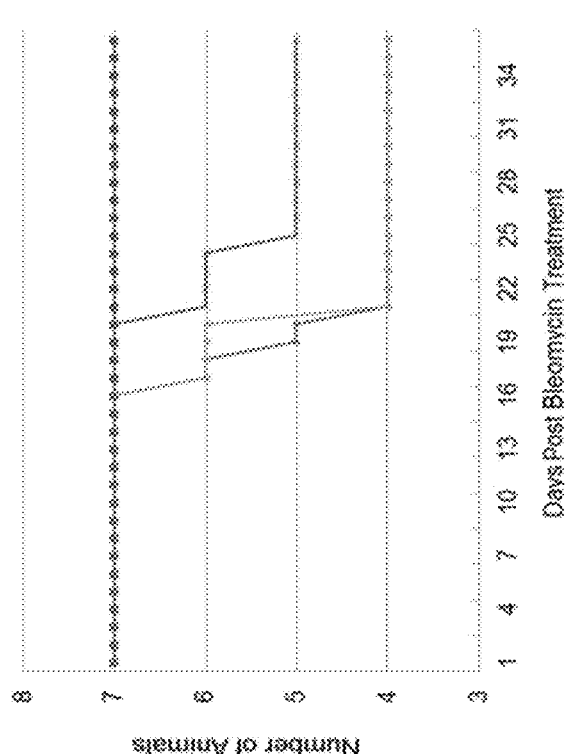

FIG. 9 is a graph illustrating results from mice (5-6 weeks old, 7 per group) primed with antibody intraperitoneally according to the following treatment groups: (1) control (PBS, diamonds); (2) anti-HDGF H3 plus anti-HDGF C1 125 ug each (H3+C1, squares); (3) chimeric anti-HDGF H3/VEGF trapper plus anti-HDGF C1, 125 ug each (H3K+C1, triangles); and (4) chimeric anti-HDGF H3/TGFB trapper plus anti-HDGF C1, 125 ug each (h3T+C1, x). Bleomycin (36 ug/animal) was given intratracheally 24-hours later under anesthesia. Antibodies were again given on day 3 (24-hr post-bleomycin instillation), and every three days thereafter for a total of 7 doses (including priming). Animals were monitored daily.

Figure 10B:
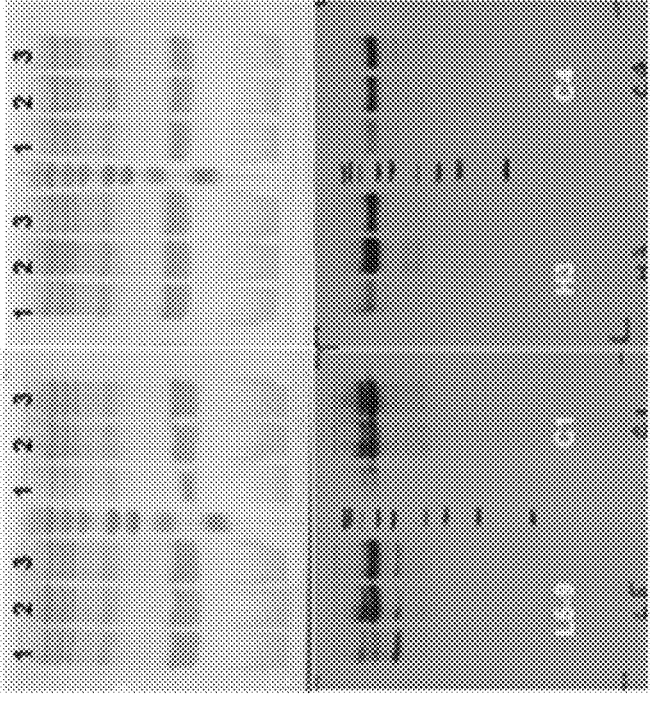
Figure 10A:
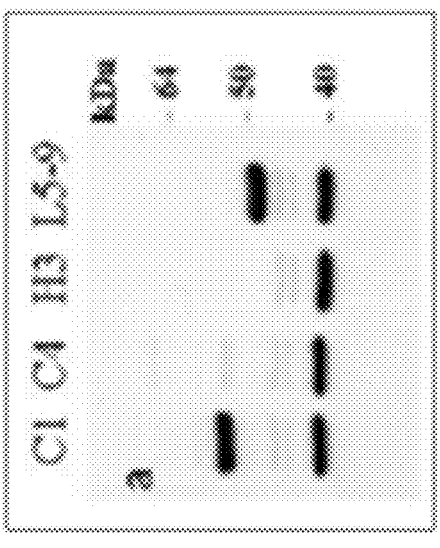

FIG. 10A and FIG. 10B are images of high-level, sustained HDGF expression results after bleomycin treatment induced lung injury. FIG. 10A: Reorganization of native and post-transcriptionally modified HDGF by various anti-HDGF antibodies in A549 lung cancer cell protein extract on Western blot. FIG. 10B: Anti-HDGF antibody staining of protein extracts from Bleomycin treated lung.

FIG. 11A, FIG. 11B, FIG. 11C, and FIG. 11D are images of anti-HDGF antibody inhibiting fibrosis in bleomycin damaged lung tissue. Mice were instilled with bleomycin intratracheally; anti-HDGF H3 plus C1 were given 24 hours later. Mice then were sacrificed after one week. Lung were dissected, fixed in 4% formalin, embedded in paraffin, then 4 um sections were cut. The tissue sections were stained with hematoxylin and cosin. FIG. 11A: normal lung; FIG. 11B: Bleomycin only; FIG. 11C: Bleomycin plus PBS sham treatment; and FIG. 11D: Bleomycin plus anti-HDGF treatment.

Figures 12A, 12B:
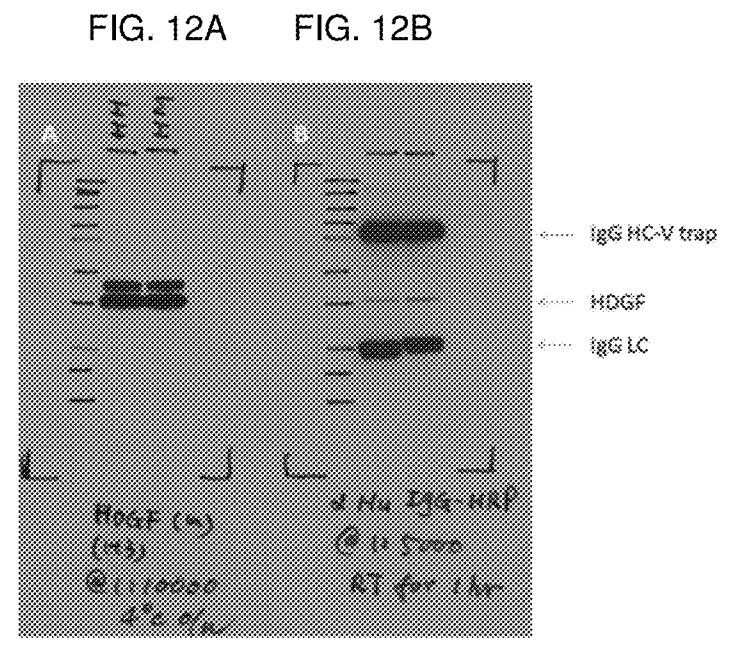

FIG. 12A and FIG. 12B are illustrations of immunoprecipitation of HDGF by humanized H3K. Humanized H3 was incubated with lung cancer cell lysate to bind HDGF. The immune complex was captured with Protein G beads and analyzed by western blotting. The lane marked HH was produced using humanized heavy chain-V trap and humanized light chains; the lane marked HM was produced using humanized heavy chain-V trap and chimeric light chain.

FIG. 12A shows staining with mouse anti-HDGF H3 antibody. In FIG. 12B, shows blot re-staining with goat-anti-human IgG HRP conjugate.

Figure 13C:
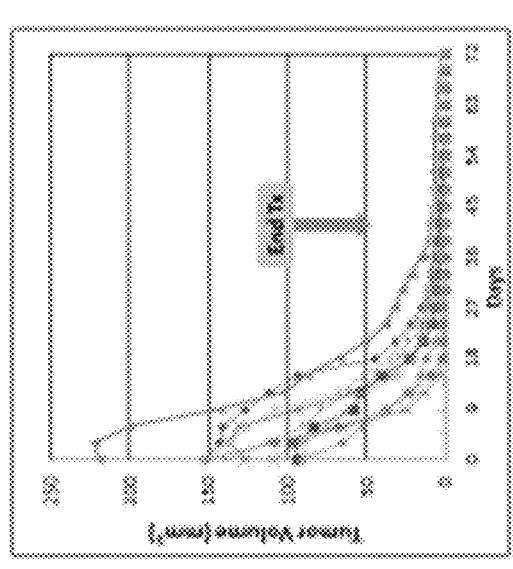
Figure 13B:
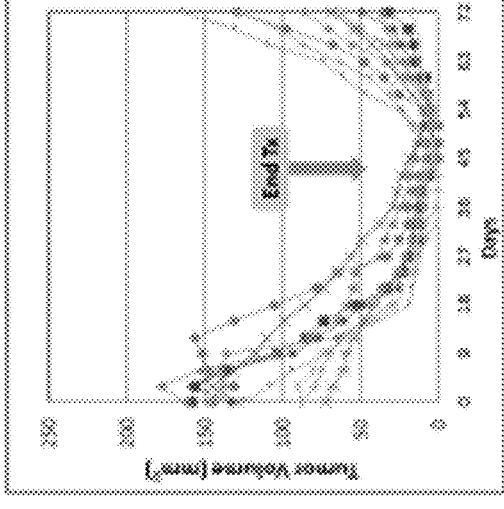
Figure 13A:
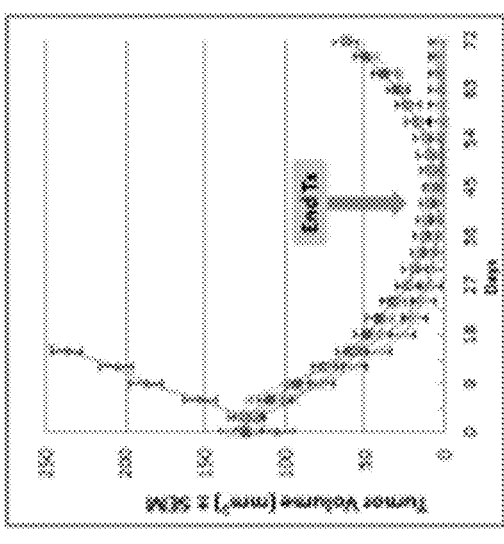

FIG. 13A, FIG. 13B, and FIG. 13C are a series of three graphs showing the response of nude mice carrying human NSCLC PDX tumor MDA274 to the indicated anticancer therapies. FIG. 13A shows a summary of five treatment regimens. FIG. 13B and FIG. 13C show tumor volumes of individual mice. See Example 7.

Figures 14A, 14B, 14C:
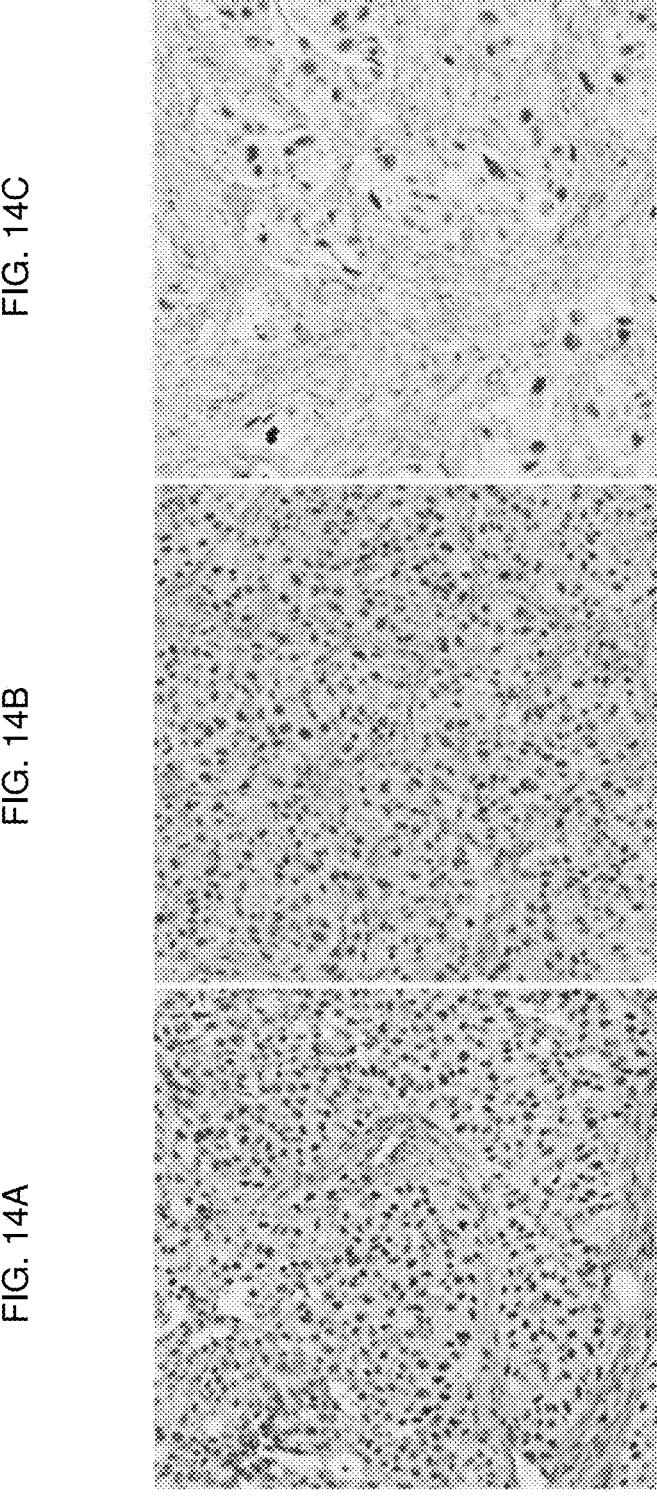

FIG. 14A, FIG. 14B, and FIG. 14C are a series of three photographs showing MDA 2131 anti SOX2 immunohistochemical staining of treatment naïve tumor (FIG. 14A), tumor treated with Gemzar™ plus anti-VEGF treatment (FIG. 14B), and tumor treated with Gemzar™ plus H3K (FIG. 14C).

Figures 15A, 15B, 15C:
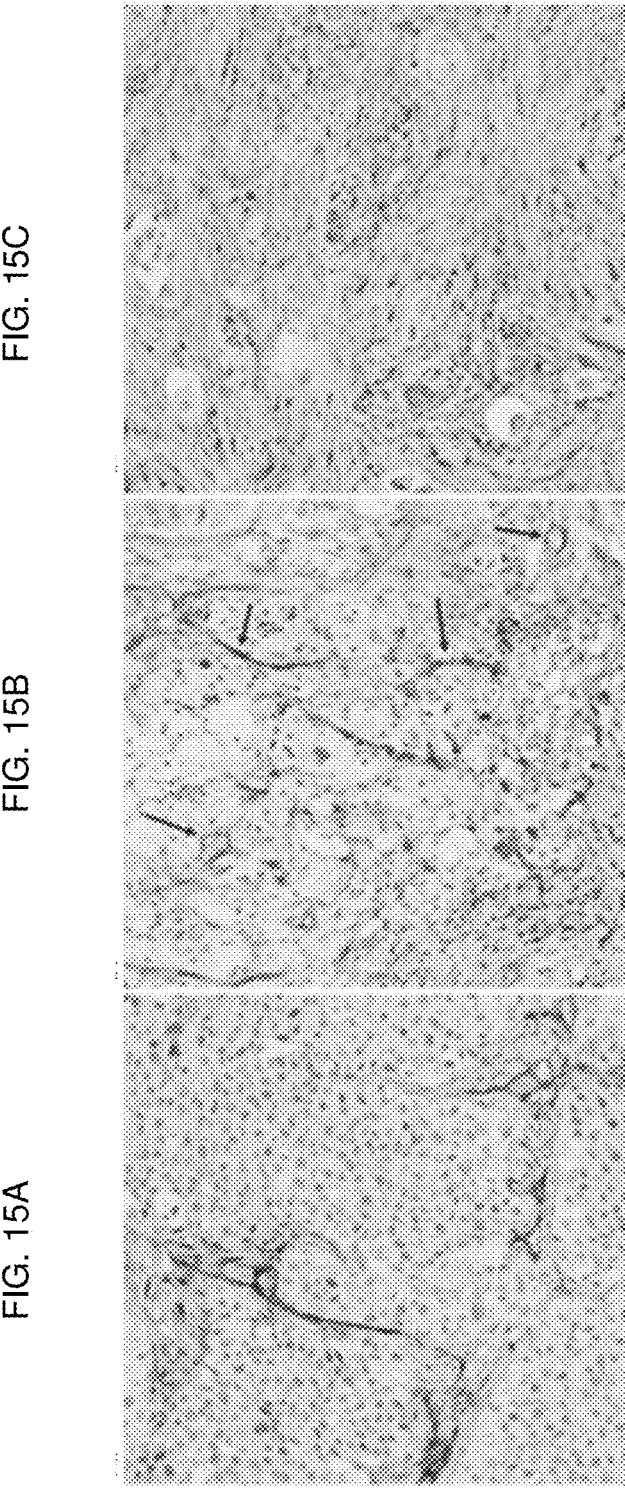

FIG. 15A, FIG. 15B, and FIG. 15C are a series of three photographs showing MDA 2131-8 anti-CD34 immunohistochemical staining of treatment naïve tumor (FIG. 15A), tumor treated with Gemzar™ plus anti-VEGF treatment (FIG. 15B), and tumor treated with Gemzar™ plus H3K (FIG. 15C).

Figures 16A, 16B, 16C:
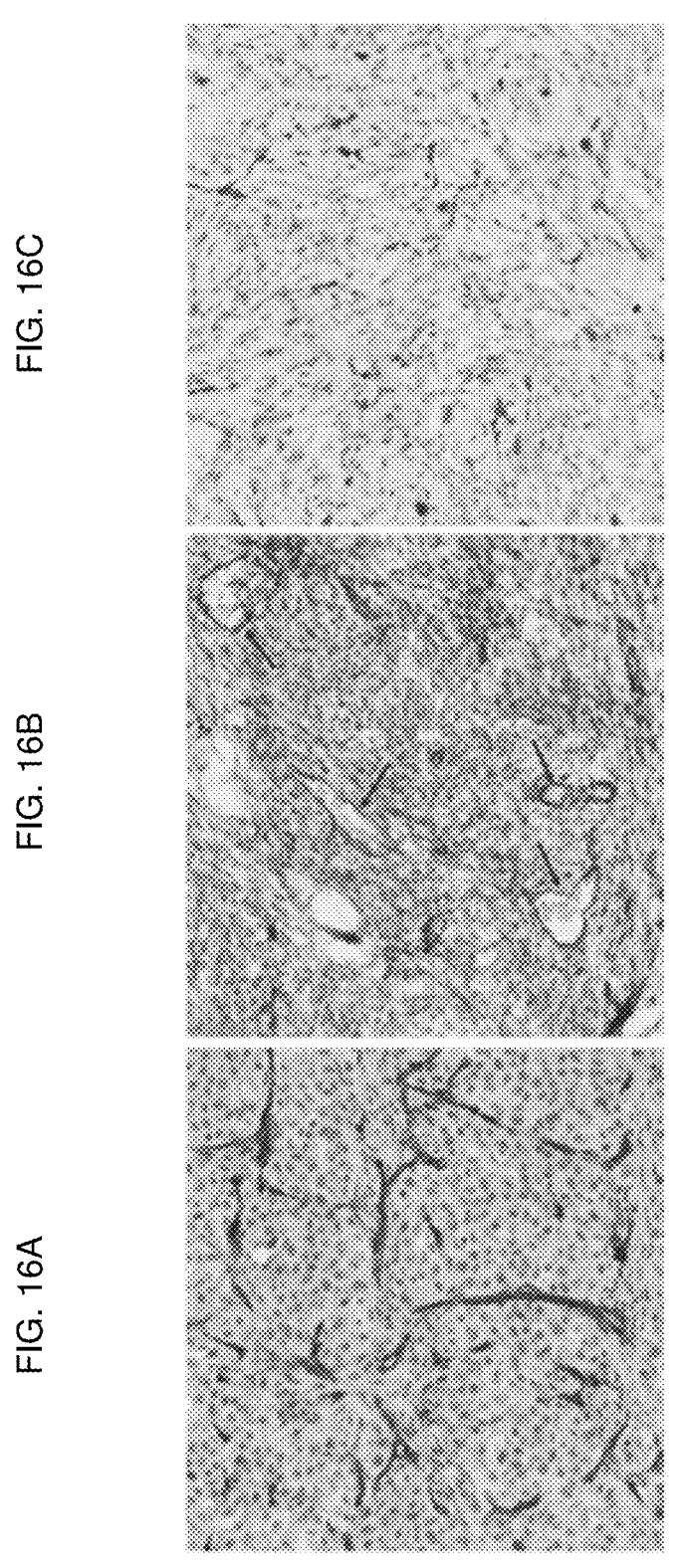

FIG. 16A FIG. 16B, and FIG. 16C are a series of three photographs showing MDA 2131-8 anti-CD31 immunohistochemical staining of treatment naïve tumor (FIG. 16A), tumor treated with Gemzar™ plus anti-VEGF treatment (FIG. 16B), and tumor treated with Gemzar™ plus H3K (FIG. 16C).

Figures 17A, 17B:
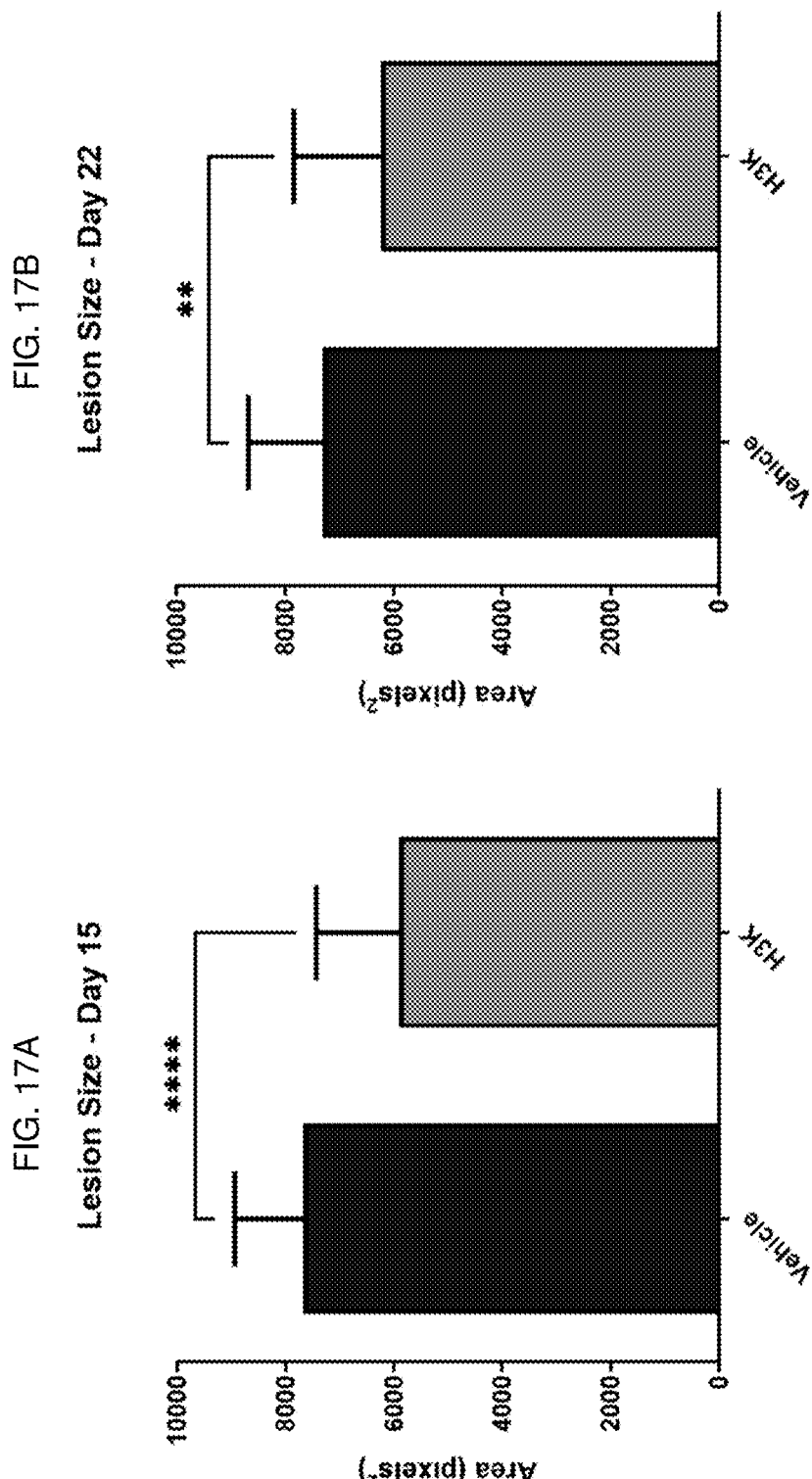

FIG. 17A and FIG. 17B show results for the lesion size (neovascularization) on day 15 (FIG. 17A) and day 22 (FIG. 17B). Vehicle: Balanced Saline Solution (BSS); H3K: 0.336 mg.

FIG. 18A and FIG. 18B show results for vascular leakage on day 15 (FIG. 18A) and day 22 (FIG. 18B). Vehicle: BSS; H3K: 0.336 mg.

DETAILED DESCRIPTION OF PREFERRED EMBODIMENTS

1. Introduction

A panel of anti-HDGF antibodies as shown in Table 1 (C1, C4, H3, cH3, hH3, H3K, hH3K, H3T, hH3T, and L5-9) has been generated in an effort to generate an antibody-based therapeutic strategy to treat hyperproliferative conditions as described herein. Treating abnormal proliferation of fibroblasts that cause keloid scarring or lung fibrosis and treating lung cancer with a novel bi-functional molecule targeting growth factors (e.g., H3K, hH3K, H3T, and hH3T) allow for a more effective simultaneous targeting of not only HDGF, but one or both of two over-produced angiogenic factors (i.e., VEGF and TGFβ).

TABLE 1

Antibodies Targeting Growth Factors in Treating Hyperproliferative Conditions.

| ANTIBODY | TYPE OF ANTIBODY | TARGET | PRODUCTION VEHICLE |
|---|---|---|---|
| H3 | mouse monoclonal | HDGF | hybridoma cell line |
| cH3 | chimeric | HDGF | plasmid expression clones |
| hH3 | humanized | HDGF | plasmid expression clones |
| H3K | chimeric bifunctional | HDGF, VEGF-A, VEGF-C | plasmid expression clones |
| hH3K | humanized bifunctional | HDGF, VEGF-A, VEGF-C | plasmid expression clones |
| H3T | chimeric bifunctional | HDGF, TGF-beta | plasmid expression clones |
| hH3T | humanized bifunctional | HDGF, TGF-beta | plasmid expression clones |
| C1 | mouse monoclonal | HDGF | hybridoma cell line |
| C4 | mouse monoclonal | HDGF | hybridoma cell line |
| L5-9 | mouse monoclonal | HDGF | hybridoma cell line |

Therefore, embodiments are directed to a bifunctional hepatoma-derived growth factor (HDGF)-specific antibody comprising at least one complementarity determining region (CDR) specific for HDGF and at least one receptor domain that specifically binds to a growth factor selected from vascular endothelial growth factor (VEGF) or transforming growth factor beta (TGFβ). In some embodiments, pharmaceutical compositions comprising the bifunctional hepatoma-derived growth factor (HDGF)-specific antibody with a pharmaceutically acceptable carrier are provided. Further embodiments include methods reducing the growth of hyperproliferative cells in a subject by administering to the subject the bifunctional hepatoma-derived growth factor (HDGF)-specific antibody in an amount of that down regulates HDGF and VEGF expression or HDGF and TGFβ expression and is effective to reduce the abnormal growth of the hyperproliferative cells. The antibody and the bifunctional antibody did not reduce the expression of these factors in the cells that produce them, only to block the binding of these factors to cells that have receptors for these factors, e.g., fibroblasts, vascular endothelial cells, or cancer cells). Therefore, methods are provided for simultaneously reducing expression of HDGF and VEGF or HDGF and TGFβ (or both) in a subject in need thereof by administering bifunctional hepatoma-derived growth factor (HDGF)-specific antibody. The subject in need suffers from a hyperproliferative condition selected from the group consisting of interstitial lung disease, keloids, lung fibrosis, idiopathic pulmonary fibrosis, lung cancer, pancreatic cancer, colon cancer, ovarian cancer, liver cancer, glioblastoma, diabetic retinopathy, age-related macular degeneration, and squamous cell carcinoma.

2. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d cd., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "antibody" as used herein means an immunoglobulin molecule, a fragment of an immunoglobulin molecule, or a derivative or variant of either thereof, which has the ability to specifically bind to an antigen under typical physiological conditions.

The term, "chimeric antibody (cAb)" as used herein, means an antibody wherein the variable region is derived from one species (e.g., derived from rodents) and the constant region is derived from a different species, such as human. Chimeric antibodies may be generated by antibody engineering. "Antibody engineering" is a term used generically for different kinds of modifications of antibodies, and which is a well-known process for the skilled person. In particular, a chimeric antibody may be generated by using standard DNA techniques known in the art. Thus, the chimeric may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may for typically contain non-human (e.g., murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin. A chimeric antibody made by fusing the antigen binding region (variable domains of the heavy and light chains, VH and VL) from one species like a mouse, with the constant domain (effector region) from another species such as a rabbit. The chimeric antibodies retain the original antibody's antigen specificity and affinity.

The term "humanized antibody" as used herein, refers to a genetically engineered non-human antibody, which contains human antibody constant domains and non-human and human variable domains modified to contain a high level of sequence homology to human variable domains. This can be achieved by grafting the antibody complementarity-determining regions (CDRs), which together form the antigen binding site, onto a homologous human acceptor framework region (FR) In order to fully reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties. The humanized or chimeric antibody according to any aspect or embodiment of the present invention may be termed "humanized or chimeric H3 antibody" (e.g., H3K or H3T). The amino acid sequence of an antibody of non-human origin is distinct from antibodies of human origin, and therefore a non-human antibody is potentially immunogenic when administered to human patients. However, despite the non-human origin of the antibody, its CDR segments are responsible for the ability of the antibody to bind to its target antigen and humanization aims to maintain the specificity and binding affinity of the antibody. Thus, humanization of non-human therapeutic antibodies is performed to minimize its immunogenicity in man while such humanized antibodies at the same time maintain the specificity and binding affinity of the antibody of non-human origin.

The term "immunoglobulin heavy chain", "heavy chain of an immunoglobulin" or "heavy chain" as used herein is intended to refer to one of the chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The heavy chain constant region may further comprise a hinge region. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized. Within the structure of the immunoglobulin, the two heavy chains are inter-connected via disulfide bonds in the so-called "hinge region." As in the heavy chains, each light chain typically comprises several regions; a light chain variable region (abbreviated herein as VL) and a light chain constant region (abbreviated herein as CL). The light chain constant region typically comprises one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL typically is composed of three CDRs and four FRs, arranged from amino-terminus to carboxy-terminus in the following order: FR1, CDR1, FR2, CDR2, FR3, CDR3, FR4. CDR sequences may be determined by use of methods known in the art.

The term "Fab-antigen binding region" as used herein, refers to a region comprising, in the direction from the N- to C-terminal, at least a hinge region, a VL and VH region, and a CL and CH1 region. It binds to antigens and is composed of one constant and one variable domain of each of the heavy and the light chain.

The term "Fc-effector binding region" as used herein, refers to a region comprising, in the direction from the N- to C-terminal, at least a hinge region, a CH2 region and a CH3 region. An Fc region may further comprise a CH1 region at the N-terminal end of the hinge region.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat.

The term "isotype" as used herein, refers to the immunoglobulin class (for instance IgG1, IgG2, IgG3, IgG4, IgD, IgA, IgE, or IgM) or any allotype thereof, that is encoded by heavy chain constant region genes. Thus, in one embodiment, the antibody comprises a heavy chain of an immunoglobulin of the IgG1 class or any allotype thereof. Further, each heavy chain isotype can be combined with either a kappa (K.) or lambda (2) light chain.

The term "hyperproliferative condition" as used herein refers to a condition or disorder or disease due to an abnormal proliferation of cells (e.g., endothelial cells, pericytes, smooth muscle cells). In preferred embodiments, fibroblasts, cancer cells, and vascular endothelia cells are examples of cells.

The terms "ophthalmic pathologies" or "ocular pathologies" as used herein refers to conditions and diseases of the eye, including, but not limited to macular degeneration (including wet (neovascular) and dry forms, diabetic retinopathy, retinal vein occlusion, neovascular vitreoretinopathy, retinopathy of prematurity, and the like.

The terms "macular degeneration" or "age-related macular degeneration," as used herein, refers to a medical condition involving blurring or loss of vision in the central field. Neovascular age-related macular degeneration" is a type of age-related macular degeneration, also known as "wet" age-related macular degeneration, which is characterized by the formation of new blood vessels underneath the retina (choroidal neovascularization) that can lead to blood or fluid leaking to produce distorted vision.

The term, "subject" as used herein means an organism that, including but not limited to mammals, e.g., humans, dogs, cows, horses, kangaroos, pigs, sheep, goats, cats, mice, rabbits, rats, and transgenic non-human animals. Synonyms used herein include "patient" and "animal."

The term, "therapeutically effective amount" as used herein means an amount of a therapeutic agent that achieves an intended therapeutic effect in a subject, e.g., eliminating or reducing or mitigating the severity of a disease or condition, or a symptom of the disease or condition. The full therapeutic effect does not necessarily occur by administration of one dose and may occur only after administration of a series of doses. Thus, a therapeutically effective amount may be administered in one or more administrations.

The term, "treating" as used herein means taking steps to obtain beneficial or desired results, including clinical results, such as, for example, mitigating, alleviating or ameliorating one or more symptoms of a disease; diminishing the extent of disease; delaying or slowing disease progression; ameliorating and palliating or stabilizing a metric (statistic) of disease. The effect may be prophylactic in terms of completely or partially preventing a conditions or disease or symptom thereof and/or may be therapeutic in terms of a partial or complete cure for a condition or disease and/or adverse effect attributable to the condition or disease. "Treatment" refers to the steps taken. It can include any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example causing regression of the condition or disease or symptom thereof by administering a therapeutically effective amount of the antibody.

3. Background

A. HDGF

In 1994, investigators described a novel human HDGF in Nakamura, H., et al., "Molecular cloning of complementary DNA for a novel human hepatoma-derived growth factor: its homology with high mobility group-1 protein," J. Biol. Chem. 269:25143-25149, 1994. HDGF was purified from conditioned medium of human hepatoma-derived cell line HuH-7. Molecular cloning of a cDNA from the cDNA library of the same cell line was done on the basis of the N-terminal amino acid sequence. The cDNA was 2.4 kb long and the deduced amino acid sequence contained 240 amino acids without a signal peptide-like N-terminal hydrophobic sequence. By immunofluorescence study, investigators showed that HDGF is localized in the cytoplasm of hepatoma cells. Northern blots illustrated that HDGF is expressed ubiquitously in normal tissues and tumor cell lines. It was then suggested that it is a novel heparin-binding protein with mitogenic activity for fibroblasts. By PCR screening of a commercial monochromosomal hybrid panel, investigators described the gene encoding HDGF in Wanschura, S., et al., in "Mapping of the gene encoding the human hepatoma-derived growth factor (HDGF) with homology to the high-mobility group (HMG)-1 protein to Xq25," Genomics 32:298-300, 1996 mapped HDGF to the X chromosome. By FISH, they refined the localization to Xq25. Subsequently, however, the International Radiation Hybrid Mapping Consortium mapped the HDGF gene to chromosome 1. Amberger, J. S. Personal Communication. Baltimore, Md. Dec. 11, 2007 refined the localization to 1q21 based on an alignment of the HDGF sequence (GenBank D16431 with the genomic sequence (build 36.2). HDGF in *Mus musculus* bears Accession number NP_032257.

B. VEGF

Another growth factor known as VEGF was purified by Gospodarowicz et al. (1989) and Ferrara and Henzel (1989) from conditioned medium of bovine pituitary folliculostellate cells. An endothelial cell proliferation assay was used to monitor the biological activity of the protein. Vascular endothelial growth factor (VEGF), originally known as vascular permeability factor (VPF), is a signal protein produced by cells that stimulates vasculogenesis and angiogenesis. VEGF is part of a larger system that restores the oxygen supply to tissues when blood circulation is inadequate such as in hypoxic conditions. It has been noted that VEGF serum concentration is high in bronchial asthma and diabetes mellitus. VEGF's normal function is to create new blood vessels during embryonic development, new blood vessels after injury, muscle following exercise, and new vessels (collateral circulation) to bypass blocked vessels.

When VEGF is overexpressed, it can contribute to disease. Solid cancers cannot grow beyond a limited size without an adequate blood supply. Cancer cells that can express VEGF are able to grow and metastasize. Overexpression of VEGF can cause vascular disease in the retina of the eye. Drugs such as aflibercept, bevacizumab, and ranibizumab can inhibit VEGF and control or slow those diseases.

More specifically, VEGF is a sub-family of growth factors, the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature). The VEGF family comprises in mammals five members: VEGF-A, placenta growth factor (PGF), VEGF-B, VEGF-C and VEGF-D. See Table 2, below.

TABLE 2

| VEGF Family. | |
| --- | --- |
| Type | Function |
| VEGF-A | Angiogenesis<br>↑ Migration of endothelial cells<br>↑ mitosis of endothelial cells<br>↑ Matrix metalloproteinase activity<br>↑ avß3 activity<br>creation of blood vessel lumen<br>creates fenestrations<br>Chemotactic for macrophages and granulocytes<br>Vasodilation (indirectly by NO release |
| VEGF-B | Embryonic angiogenesis (myocardial tissue, to be specific) |
| VEGF-C | Lymphangiogenesis |
| VEGF-D | Needed for the development of lymphatic vasculature surrounding lung bronchioles |
| PIGF | Important for Vasculogenesis, Also needed for angiogenesis during ischemia, inflammation, wound healing, and cancer. |

Adapted from Wikipedia.

VEGF-A has been correlated with poor prognosis in breast cancer. Numerous studies show a decreased overall survival and disease-free survival in those tumors overexpressing VEGF. The overexpression of VEGF-A may be an early step in the process of metastasis, a step that is involved in the "angiogenic" switch. Although VEGF-A has been correlated with poor survival, its exact mechanism of action in the progression of tumors remains unclear. VEGF-A is also released in rheumatoid arthritis in response to TNF-α, increasing endothelial permeability, swelling, and stimulating angiogenesis. VEGF-A is also implicated in diabetic retinopathy (DR). The microcirculatory problems in the retina of people with diabetes can cause retinal ischemia, which results in the release of VEGF-A. This can cause the creation of new blood vessels in the retina and elsewhere in the eye, heralding changes that may threaten the sight. VEGF-A plays a role in the disease pathology of the wet form age-related macular degeneration (AMD), which is the leading cause of blindness for the elderly of the industrialized world. The vascular pathology of AMD shares certain similarities with diabetic retinopathy, although the cause of disease and the typical source of neovascularization differ between the two diseases. Once released, VEGF-A may elicit several responses. It may cause a cell to survive, move, or further differentiate. Hence, VEGF is a potential target for the treatment of cancer. The first anti-VEGF drug, a monoclonal antibody named bevacizumab, was approved in 2004. Approximately 10-15% of patients benefit from bevacizumab therapy; however, biomarkers for bevacizumab efficacy are not yet known. VEGF-D serum levels are significantly elevated in patients with angiosarcoma. Patients suffering from pulmonary emphysema have been found to have decreased levels of VEGF in the pulmonary arteries. In the kidney, increased expression of VEGF-A in glomeruli directly causes the glomerular hypertrophy that is associated with proteinuria. VEGF alterations can be predictive of early-onset pre-eclampsia.

C. TGFβ

A growth factor known as transforming growth factor beta (TGF-β) is a multifunctional cytokine belonging to the transforming growth factor superfamily that includes three different isoforms (TGF-β 1 to 3, HGNC symbols TGFB1, TGFB2, TGFB3) and many other signaling proteins produced by white blood cell lineages. Activated TGF-β complexes with TGF-β receptors, which is composed of both type 1 and type 2 receptor subunits. After the binding of TGF-β, the type 2 receptor kinase phosphorylates and activates the type 1 receptor kinase that activates a signaling cascade. This leads to the activation of different downstream substrates and regulatory proteins, inducing transcription of different target genes that function in differentiation, chemotaxis, proliferation, and activation of many immune cells.

TGF-β is secreted by many cell types, including macrophages, in a latent form in which it is complexed with two other polypeptides, latent TGF-beta binding protein (LTBP) and latency-associated peptide (LAP). Serum proteinases such as plasmin catalyze the release of active TGF-β from the complex. This often occurs on the surface of macrophages where the latent TGF-β complex is bound to CD36 via its ligand, thrombospondin-1 (TSP-1). Inflammatory stimuli that activate macrophages enhance the release of active TGF-β by promoting the activation of plasmin. Macrophages can also endocytose IgG-bound latent TGF-β complexes that are secreted by plasma cells and then release active TGF-β into the extracellular fluid. Among its key functions is regulation of inflammatory processes, particularly in the gut.[4] TGF-β also plays a crucial role in stem cell differentiation as well as T-cell regulation and differentiation. As such, it is a highly researched cytokine in the fields of cancer, auto-immune diseases, and infectious disease.

The TGFβ superfamily includes endogenous growth inhibiting proteins; an increase in expression of TGFβ often correlates with the malignancy of many cancers and a defect in the cellular growth inhibition response to TGFβ. Its immunosuppressive functions then come to dominate, contributing to oncogenesis. The dysregulation of its immunosuppressive functions is also implicated in the pathogenesis of autoimmune diseases, although their effect is mediated by the environment of other cytokines present.

The primary three types are:

TGF beta 1—TGFB1

TGF beta 2—TGFB2

TGF beta 3—TGFB3

The peptide structures of the TGF-β isoforms are highly similar (homologies on the order of 70-80%). They are all encoded as large protein precursors; TGF-β1 contains 390 amino acids and TGF-β2 and TGF-β3 each contain 412 amino acids. They each have an N-terminal signal peptide of 20-30 amino acids that they require for secretion from a cell, a pro-region called latency associated peptide (LAP), and a 112-114 amino acid C-terminal region that becomes the mature TGF-β molecule following its release from the pro-region by proteolytic cleavage. The mature TGF-β protein dimerizes to produce a 25 KDa active protein with many conserved structural motifs. TGF-β has nine cysteine residues that are conserved among its family. Eight of the residues form disulfide bonds within the protein to create a cysteine knot structure characteristic of the TGF-β superfamily. The ninth cysteine forms a disulfide bond with the ninth cysteine of another TGF-β protein to produce a dimer. Many other conserved residues in TGF-β are thought to form secondary structure through hydrophobic interactions. The region between the fifth and sixth conserved cysteines houses the most divergent area of TGF-β proteins that is exposed at the surface of the protein and is implicated in receptor binding and specificity of TGF-β.

In normal cells, TGFβ, acting through its signaling pathway, stops the cell cycle at the G1 stage to stop proliferation, induce differentiation, or promote apoptosis. In many cancer cells, parts of the TGFβ signaling pathway are mutated, and TGFβ no longer controls the cell. These cancer cells proliferate. The surrounding stromal cells (fibroblasts) also proliferate. Both cells increase their production of TGFβ. This TGFβ acts on the surrounding stromal cells, immune cells, endothelial and smooth-muscle cells. It causes immunosuppression and angiogenesis, which makes the cancer more invasive. TGFβ also converts effector T-cells, which normally attack cancer with an inflammatory (immune) reaction, into regulatory (suppressor) T-cells, which turn off the inflammatory reaction.

4. Overview

HDGF, VEGF, and TGFβ are overexpressed in hyperproliferative conditions such as keloids, lung fibrosis and lung cancer. The overexpression correlates with aggressive biologic behaviors and poor clinical outcomes. Monoclonal antibodies specific for HDGF and chimeric and humanized versions of them (i.e., H3, C1, C4, and L5-9) have been previously developed by us and are provided in Table 1 and described in Ren, H. et al., "Antibodies targeting hepatoma-derived growth factor as a novel strategy in treating lung cancer." Mol Cancer Ther. 2009 May; 8 (5): 1106-1112 and incorporated herein. Ren et al. determined that anti-HDGF was effective to inhibit tumor growth in non-small cell lung cancer xenograft models. When the monoclonal antibody H3 was combined with either bevacizumab or gemcitabine, tumor growth inhibition was enhanced. Here, both chimeric and humanized bifunctional antibodies have been created (i.e., H3K, hH3K, H3T, and hH3T) to simultaneously target two additional growth factors (VEGF and TGFβ) in tumor tissue. In patient-derived tumor xenograft mouse models, treatment with the bi-functional antibody H3K interfered with tumor drug resistance and demonstrated long-term remission. In mouse models of lung fibrosis, anti-HDGF antibodies in various combinations before or after bleomycin-induced damage showed therapeutic effects on survival and inhibition of fibrosis. Without being bound by theory, treatment of abnormal proliferation of fibroblasts with the bi-functional antibodies (i.e., H3K, hH3K. H3T, and hH3T) will provide an improved response in view of the simultaneous targeting of HDGF and VEGF or HDGF and TGFβ. This novel molecule targeting HDGF, with a VEGF trap or TGFβ trap is easier to administer as a single molecule and enhances treatment by providing equal or better effects while triggering ADCC in cancer cells. Strategies are also provided herein for reducing abnormal proliferation of fibroblasts using antibodies described in Table 1.

5. Embodiments

Therefore, embodiments of the invention include a bifunctional hepatoma-derived growth factor (HDGF)-specific antibody molecule (e.g., H3K, hH3K, H3T and hH3T) comprising at least one complementarity determining region (CDR) specific for HDGF and at least one receptor domain that specifically binds to a growth factor selected from vascular endothelial growth factor (VEGF) and transforming growth factor beta (TGFβ). In other embodiments, a single chain antibody (scFv) is created and can be combined with a variety of functional moieties. In some embodiments, pharmaceutical compositions comprising the bifunctional hepatoma-derived growth factor (HDGF)-specific antibody with a pharmaceutically acceptable carrier are provided. The pharmaceutical composition may be formulated for parenteral, intravenous, intraocular, topical administration, or administration of eye drops. Preferably the pharmaceutical composition is formulated for administration in an amount from 5 to 25 mg/kg every 1-3 weeks. Further embodiments include methods reducing the growth of hyperproliferative cells in a subject by administering to the subject the bifunctional hepatoma-derived growth factor (HDGF)-specific antibody in an amount of that down regulates HDGF and VEGF expression or HDGF and TGFβ expression and is effective to reduce the abnormal growth of the hyperproliferative cells. In some embodiments, the hyperproliferative cell may be a fibroblast or a cancer cell, or a vascular endothelial cell. The cancer cell may be selected from the group consisting of lung, pancreas, colon, ovarian, liver, breast, glioblastoma, and squamous cell carcinoma. And in other embodiments, methods are provided for simultaneously reducing expression of HDGF and VEGF or HDGF and TGFβ in a subject in need thereof by administering bifunctional hepatoma-derived growth factor (HDGF)-specific antibody. The subject in need suffers from a hyperproliferative condition selected from the group consisting of interstitial lung disease, keloids, lung fibrosis, idiopathic pulmonary fibrosis, lung cancer, pancreatic cancer, colon cancer, ovarian cancer, liver cancer, glioblastoma, diabetic retinopathy, age-related macular degeneration, melanoma, and squamous cell carcinoma. Particular ocular pathologies which are contemplated for method claims within the scope of this invention include age-related macular degeneration (including neovascular macular degeneration), diabetic retinopathy, retinal vein occlusion (neovascular glaucoma), peripheral vitreoretinopathy, retinopathy of prematurity.

A. Bi-Functional Molecules and Methods of Making them

Some embodiments of the invention include a bifunctional hepatoma-derived growth factor (HDGF)-specific chimeric or humanized antibody (e.g., H3K hH3K, H3T or hH3T) and each comprises at least one complementarity determining region (CDR) specific for HDGF and at least one receptor domain that specifically binds to a growth factor selected from vascular endothelial growth factor (VEGF) and transforming growth factor beta (TGFβ). The CDR may be selected from a mouse, human, rabbit, rat, CDR, preferably a mouse CDR. The antibody may be humanized or chimeric and comprises two receptor domains (e.g., VEGFR2) each of which independently bind to a growth factor selected from vascular endothelial growth factor (VEGF-A, VEGF-C, and VEGF-E) and transforming growth factor beta (TGFβ) (i.e., a TGFβ selected from TGFβ subtype 1, subtype 2, and subtype 3). In certain aspects the bifunctional hepatoma-derived growth factor (HDGF)-specific antibody is linked to a reporter molecule selected from the group consisting of, an enzyme, a radiolabel, a hapten, a fluorescent label, a phosphorescent molecule, a chemiluminescent molecule, a chromophore, a luminescent molecule, a photoaffinity molecule, a ligand, a colored particle, or biotin. In the alternative, the antibody is linked to an effector molecule selected from the group consisting of, a toxin, an apoptotic molecule, an antitumor agent, a therapeutic enzyme, or a cytokine. In some aspects of the invention, the antitumor agent is selected from the group consisting of gemcitabine, pemetrexed, cisplatin, docetaxel, vinorelbine, doxorubicin, 6-fluorouracil, erlotinib, gefitinib, and crizotinib.

Embodiments include antibodies that are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies and are responsible for binding the target antigen. The constant regions show less sequence diversity and are responsible for binding a number of natural proteins to elicit important biochemical events. In humans there are five different classes of antibodies including IgA (which includes subclasses IgAQ1 and IgA2), IgD, IgE, IgG (which includes subclasses IgG1, IgG2, IgG3, and IgG4), and IgM. The distinguishing features between these antibody classes are their constant regions, although subtler differences may exist in the V region. IgG antibodies are tetrameric proteins composed of two heavy chains and two light chains. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant γ1 domain, constant γ2 domain, and constant γ3 domain respectively). The IgG light chain is composed of two immunoglobulin domains linked from N- to C-terminus in the order VL-CL, referring to the light chain variable domain and the light chain constant domain respectively.

In some embodiments, a chimeric antibody is an antibody made by combining genetic material from a nonhuman source, like a mouse, with genetic material from a human being. Chimeric antibodies are generally around two thirds human, reducing the risk of a reaction to foreign antibodies from a non-human animal when they are used in therapeutic treatments. A closely related concept is a humanized antibody, made in a similar way but containing closer to 90% human genetic material. Using recombinant technology, people can cut and splice genetic material from multiple sources and fuse it together. A chimeric antibody contains antibodies developed with animal cells in culture, with sections of the genetic code replaced with human genes in order to address concerns about a potential reaction with the animal's genetic material.

The variable region of the Fab-antigen binding region of antibodies in some embodiments contains the antigen binding determinants of the molecule, and thus determines the specificity of an antibody for its target antigen. The variable region is so named because it is the most distinct in sequence from other antibodies within the same class. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. In preferred embodiments, the CDR is mouse CDR for HDGF.

In preferred embodiments, the CDR is a mouse CDR for HDGF. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. The sequence and structural features of antibody variable regions are well characterized (Morca et al., 1997, Biophys. Chem. 68:9-16; Morea et al., 2000, Methods 20:267-279, entirely incorporated by reference), and the conserved features of antibodies have enabled the development of a wealth of antibody engineering techniques (Maynard et al., 2000, Annu. Rev. Biomed. Eng. 2:339-376, entirely incorporated by reference). For example, it is possible to graft the CDRs from one antibody, for example a murine antibody, onto the framework region of another antibody, for example a human antibody. This process, referred to in the art as "humanization," reduces the immunogenicity of antibody therapeutics compared to nonhuman antibodies. Fragments including the variable region can exist in the absence of other regions of the antibody, including for example the antigen binding fragment (Fab) including VH-C.gamma.1 and VH-CL, the variable fragment (Fv) including VH and VL, the single chain variable fragment (scFv) including VH and VL linked together in the same chain, as well as a variety of other variable region fragments (Little et al., 2000, Immunol Today 21:364-370, entirely incorporated by reference).

A Fab fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544 546, 1989) consists of a VH domain. A single-chain antibody (scFv) is an antibody in which a VL and VH regions are paired to form monovalent molecules via a synthetic linker that enables them to be made as a single protein chain (Bird et al., Science 242:423 426, 1988 and Huston et al., Proc. Natl. Acad. Sci. USA 85:5879 5883, 1988). Such linker molecules are commonly known in the art and described in U.S. Patent Application No. 20130245233 A1, Denardo et al., (1998) Clin. Cancer Res. 4(10): 2483-90; Peterson et al., (1999) Bioconjug. Chem. 10(4): 553-7; and Zimmerman et al., (1999) Nucl. Med. Biol. 26(8): 943-50, each incorporated by reference in their entireties. Diabodies are bivalent, bispecific, or bi-functional antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., Proc. Natl. Acad. Sci. USA 90:6444 6448, 1993, and Poljak, R. J., et al., Structure 2:1121 1123, 1994). One or more CDRs may be incorporated into a molecule either covalently or noncovalently to make it bispecific.

An Fc-effector binding region is a fragment containing a constant region, termed the Fc domain, which engages a diversity of cellular receptors, thereby triggering antibody-mediated effector functions. The Fc domain acts as a bridge between the specificity dictated by the Fab region and cells of the innate and adaptive immune system. A notable common characteristic of both classes of therapeutic antibodies is the importance of the IgG Fc domain, which connects the fine specificity of an antibody with immune cells that mediate antibody-triggered effector functions through their engagement of Fc receptor (FcR) family members. In antibody dependent cellular cytotoxicity (ADCC), FcvRs on the surface of effector cells (natural killer cells, macrophages, monocytes, and eosinophils) bind to the Fc region of an IgG which itself is bound to a target cell. Engineering the antibody Fc region to enhance the cytotoxic activity of therapeutic antibodies is preferred in some embodiments. In preferred embodiments, the Fc-effort region comprises a human VEGF/TGFβ trap. The growth factor receptor dimers bind GF dimer. Fusion with the heavy chain creates a receptor dimer which may be required or enhance the binding of GF.

In preferred embodiments, anti-HDGF hybridoma were generated from Balb/c mice by immunizing with recombinant HDGF in Freund's adjuvant. Solenocytes from immunized animals were fused with P3x63Ag8.653 cells and screened for HDGF reactivity in the culture supernatant. Positive clones were identified, and anti-HDGF antibody secretion was verified by immunoblot analysis of cancer cell lysate and purified HDGF. RNA from anti-HDGF antibody producing hybridoma was extracted, reverse transcribed into cDNA. Primers designed to amplify the Ig variable region (Larrick, J. W., et al. 1989. Biochem. Biophys. Res. Comm. 160, 1250. Jones, S. T. and Bendig, M. M. 1991. Biotechnology 9, 88) were used to amplify the cDNA encoding the mouse Ig heavy and light chain. The amplified product were cloned and sequenced. The cDNA sequence that encoded the murine Ig heavy chain and light chain, and the CDRs were identified as described in http://www.bioinf.org.uk/abs/. The DNA fragments that encoded the murine antibody variable domain (VH and VL) were grafted to the N-terminal of the constant region of their human IgG1 count part by standard molecular biology techniques and cloned into a mammalian expression vector respectively. To produce the chimeric antibody, plasmids encoding for the heavy and light chain were co-transfected into Expi293 cells (Invitrogen®) at a ratio of 1:2. The antibody was purified from the conditioned media by protein G affinity chromatograph. The cDNA sequence that encoded the murine Ig heavy chain and light chain, and the CDRs were identified as described by Martin A.C.R. (http://www.bioinf.org.uk/abs/). The humanized anti-HDGF Vh sequences were then created by replacing the CDRs in human Ig G1 Vh with the corresponding murine CDRs. The DNA sequence that encodes the humanized sequence is then synthesized and grafted on the N-termini of the human IgG1 heavy chain constant region, cloned into a mammalian expression vector to generate a humanized Ig heavy chain expression construct. The humanized VL expression construct was created similarly. To produce the humanized anti-HDGF antibody, the plasmids that encode for the heavy and light chain was used to transfect Expi293 cell at a ratio of 1:2. The antibody was purified from the conditioned media by protein G affinity chromatograph.

Construction of Fc-fused growth factor binding domain (GF trapper) included a DNA fragment corresponding to domain 2 and 3 (D2 and D3) of human VEGF receptor 2 (kinase insert domain receptor) amino acid residue 122 to residue 327 (based on NP_002253) and was amplified from HEK 293 cDNA. The amplified sequence was fused to the C-terminus of the human IgG1 heavy chain via a poly-GlySer linker, (GlyGlyGlyGlySer)$_2$ (SEQ ID NO:23), or (G4S) 2. The full-length anti-HDGF antibody heavy chain-VEGF trapper sequence was cloned into a mammalian expression plasmid.

Construction of Fc-TGFB trapper included a DNA fragment corresponding to human TGFBR2 extracellular domain amino acid residue 27 to residue 184 (based on NP_001020018) was amplified from human lung cDNA. The amplified sequence was fused to the C-terminus of the human IgG1 heavy chain via a poly-GlySer linker, (GlyGlyGlyGlySer)$_2$ (SEQ ID NO:23), or (G4S) 2. The full-length anti-HDGF antibody heavy chain-TGFB trapper sequence was cloned into a mammalian expression plasmid. To produce the recombinant anti-HDGF antibody, plasmids encoding for the heavy and light chain were co-transfected into Expi293 cells (Invitrogen®) at a ratio of 1:2. The antibody was purified from the conditioned media by protein G affinity chromatograph.

Chimeric antibodies may be generated by substituting all constant region sequences of a non-human (such as murine) antibody with constant region sequences of human origin or vice versa. Thus, fully non-human variable region sequences are maintained in the chimeric antibody. Thus, a chimeric antibody according to the present invention may be produced by a method comprising the step of expressing the non-human variable heavy chain, non-human variable light chain sequences, human constant heavy chain and human constant light chain sequences in suitable expression systems, and thereby generating a full-length chimeric antibody. Alternative methods may be used. Such methods of producing a chimeric antibody is within the knowledge of the skilled person, and thus, the skilled person would know how to produce a chimeric antibody according to the present invention.

The term "recombinant human antibody," as used herein, is intended to include all human antibodies that are prepared, expressed, created or isolated by recombinant means, such as (a) antibodies isolated from an animal (e.g., a mouse) that is transgenic for human immunoglobulin genes, (b) antibodies expressed using a recombinant expression vector transfected into a host cell, (c) antibodies isolated from a recombinant, combinatorial human antibody library, and (c) antibodies prepared, expressed, created or isolated by any other means that involve splicing of human immunoglobulin gene sequences to other DNA sequences. Such recombinant human antibodies preferably have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline $V_H$ and $V_L$ sequences, may not naturally exist within the human antibody germline repertoire in vivo. Antigen-binding portions include, inter alia, Fab, Fab', F(ab')$_2$, Fv. dAb, and complementarity determining region (CDR) fragments, single-chain antibodies (scFv), chimeric antibodies, diabodies and polypeptides that contain at least a portion of an immunoglobulin that is sufficient to confer specific antigen binding to the target ceramide. Also included in the definition of antibodies is the SuperAntibody including those chemically conjugated to T15 peptide or genetically engineered into a human IgG1 backbone (see Y. Zhao, D. Lou, J. Burkett and H. Kohler. Enhanced Anti-B-cell Tumor Effects with Anti-CD20 Super-Antibody. *J. Immunotherapy*, 25:57-62, 2002). The immunoglobulin subtype can be any subtype; typically, IgG and IgM are used, but IgA, IgE, etc. also can be effective.

In preferred embodiments, the chimeric antibody may have one or more binding sites and is a bifunctional hepatoma-derived growth factor (HDGF)-specific chimeric or humanized antibody (e.g., H3K hH3K, H3T or hH3T). If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

Figure 1:
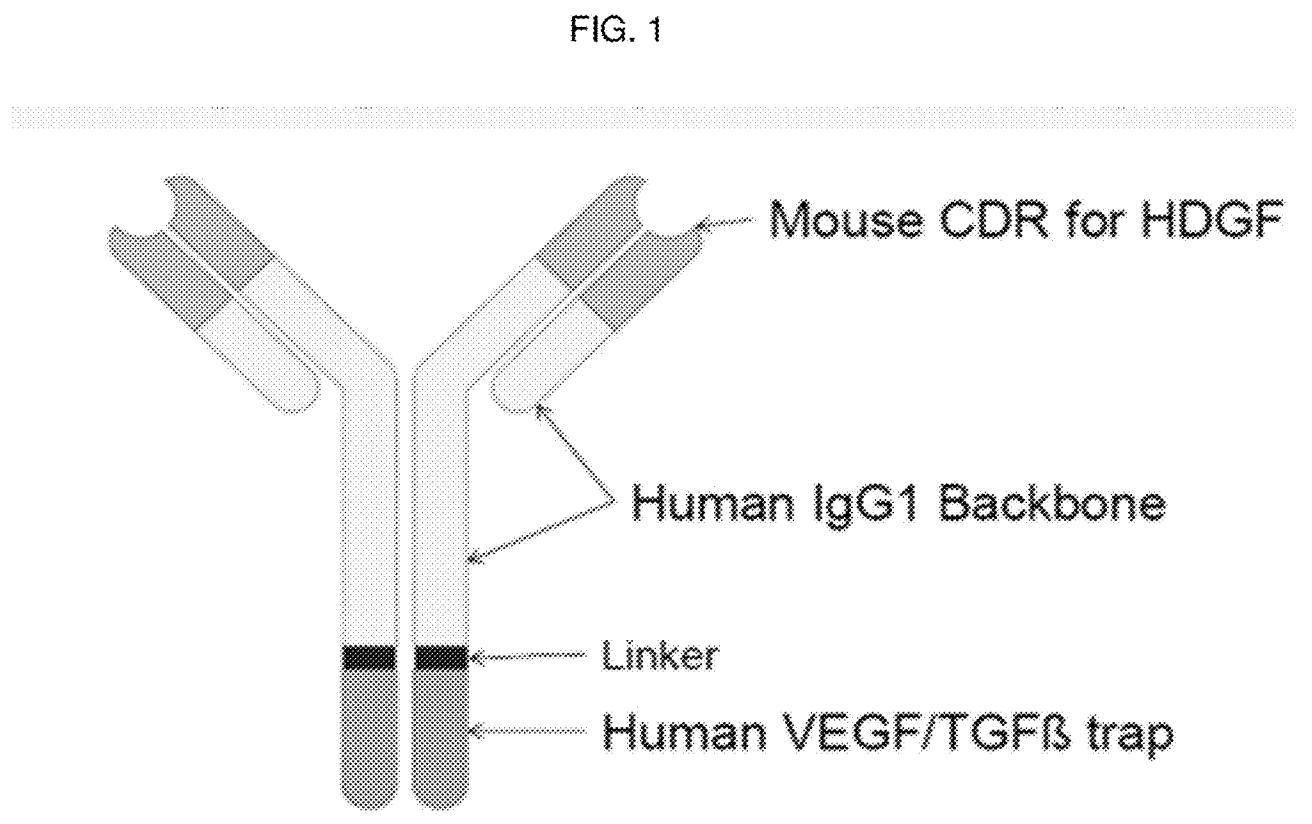
Figure 3A:
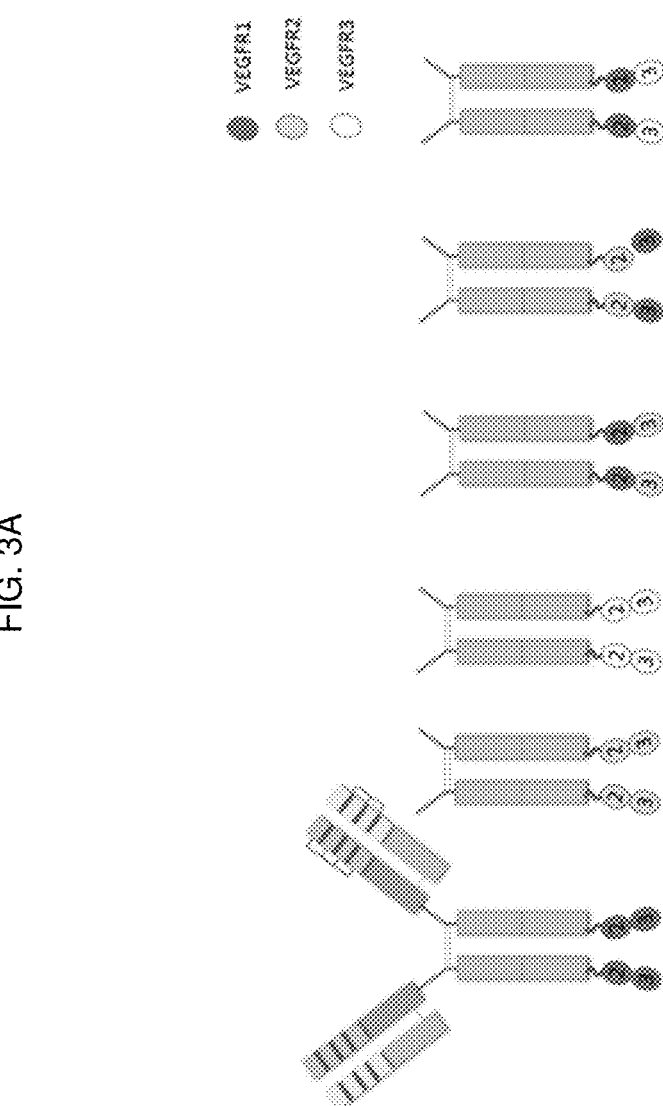
FIG. 3A and FIG. 3B are diagrams showing exemplary VEGF trapper molecules.
Figure 3B:
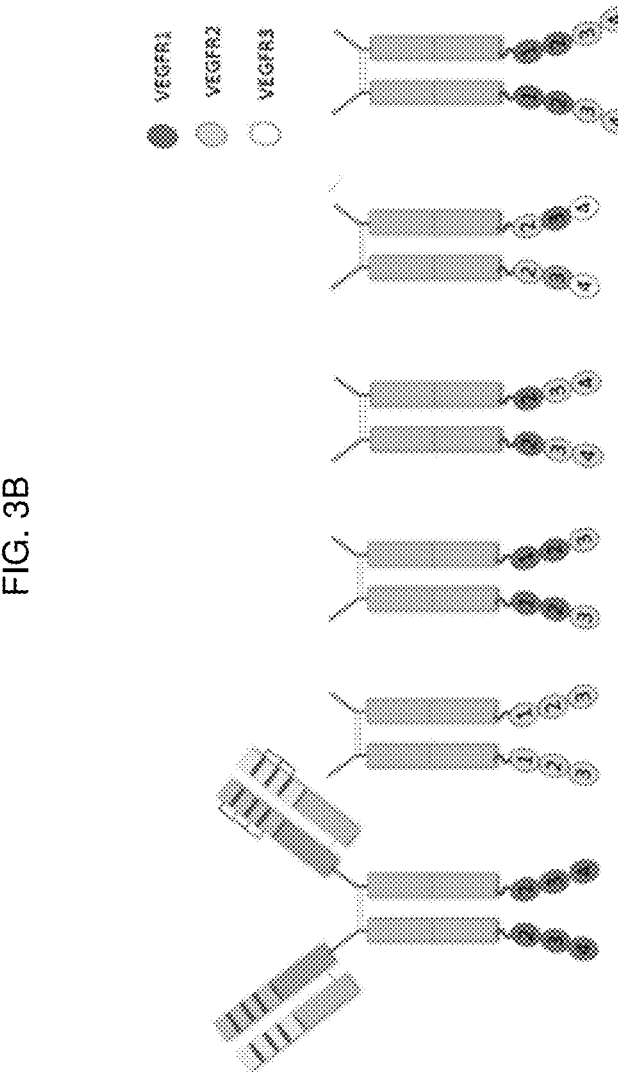

In some embodiments, the carboxy termini of the chimeric H3 heavy chain is fused to a soluble VEGF receptor (VEGF trapper). The VEGF trapper preferably is made by fusing the VEGF receptor 2 (VEGFR2) ligand binding domain with another protein at the carboxyl terminal via a linker. In this instance, the ligand binding domain consists of sequences from D2 and D3 of VEGFR2; the linker sequence here is a tandem repeat of G4S, but other types of linkers, such as a polypeptide or synthetic linker, are possible. In some embodiments, the VEGF trapper is constructed using the ligand binding domain of VEGFR1, VEGFR2 or VEGFR3; or a hybrid ligand binding domain consisting of a D2 domain selected from VEGFR1, VEGFR2 or VEGFR3, and a D3 domain selected from VEGFR1, VEGFR2 or VEGFR3; or a hybrid ECD consisting of the fusion of a D2 domain containing ECD and a D3 domain containing ECD. See FIG. 1 and FIG. 3 for examples of VEGF trapper constructions.

Without being bound by theory, the majority of the methods of making a soluble receptor derived from type I trans membrane protein/type I receptor is to fuse the N-terminal extracellular domain to the N-termini of Fc fragment due to: 1) the natural topology of the receptor protein, 2) the requirement of many of these receptors to dimerize upon binding the ligand which is often dimerized, 3) favorable PK due to similarity to antibody. Although expression as Fc fusion protein is the easiest way, it is possible to make multi-functional molecule or nanoparticle by covalent or non-covalent conjugation of VEGFR monomer or dimer, as long as it can form a dimer before or upon GF dimer binding.

The VEGF trapper has an amino acid sequence set forth in SEQ ID NO:1. Embodiments including a VEGF trapper preferably have the VEGF trapper fused at the carboxyl termini of the human IgG heavy chain. In the following example, a human IgG1 heavy chain constant region and the VEGF binding domain are shown in SEQ ID NO:2. In other embodiments, the VEGF trapper was fused at the carboxyl termini of a chimeric H3 heavy chain. In the following example, a human IgG1 heavy chain constant region and VEGF binding domain is shown in SEQ ID NO:3. The VEGF trapper alternatively was fused at the carboxyl termini of a humanized anti-HDGF H3 heavy chain (matured peptide) in other embodiments as shown in SEQ ID NO: 4. In this instance, the TGFB trapper is shown as a carboxyl-terminal fusion via a linker in SEQ ID NO:5. The linker is (G4S) 2. Other alternative embodiments include a TGFB trapper fused at the carboxyl termini of human IgG heavy chain (SEQ ID NO:6). In a further alternative embodiment, the TGFB trapper was fused at the carboxyl termini of chimeric anti-HDGF H3 heavy chain (SEQ ID NO:7). In other embodiments, the TGFB trapper was fused at the carboxyl termini of humanized anti-HDGF H3 heavy chain (matured peptide) (SEQ ID NO: 8).

Figures 2A, 2B:
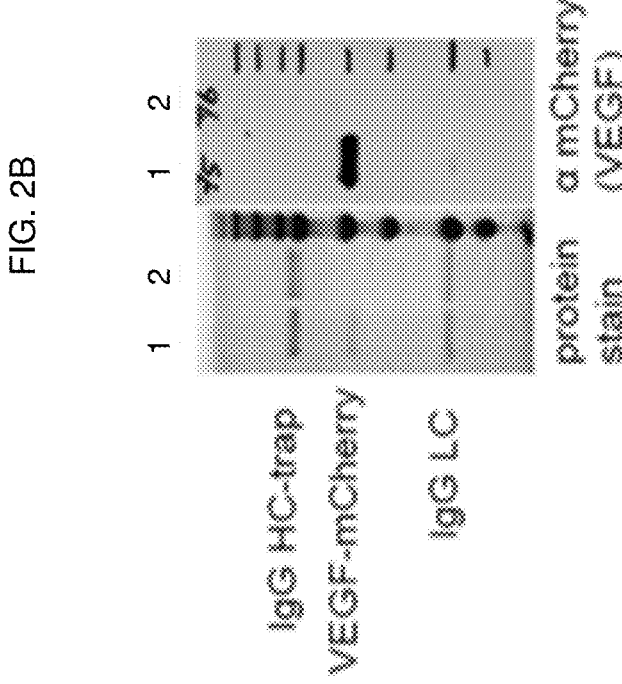
FIG. 2A and FIG. 2B are images of western blots illustrating immunoprecipitation data for hc-anti HDGF H3 and hc-H3-V/T-traps.

FIG. 2A and FIG. 2B are images of western blots illustrating immunoprecipitation data for rh-anti HDGF H3 and rh-H3-V/T-traps. Lane 1: rh-H3-V-trapper, lane 2: rh-H3-T-trapper. The results in FIG. 2A show immunoprecipitation of HDGF by recombinant rh-anti-HDGF H3. FIG. 2B shows immunoprecipitation of VEGF-mCherry fusion protein by rh-anti-HDGF H3-VEGF trapper.

H3K was produced according to the following general steps:

1. produce DNA: plasmids encoding the heavy and light chain of the recombinant antibody were amplified in *E. coli* per standard molecular biology procedure and purified.
2. transfect Expi293F (2 L): The plasmids were used to transiently transfect Expi293 cells per the manufacturer's recommended method. See thermofisher.com.
3. Antibody purification: Antibody produced in Expi293 were purified by affinity chromatograph on MabSelect SuRe as described by manufacturer's recommended method. See cdn.cytivalifesciences.com.

4. Pooled purified fractions.

6. Concentrate and formulate in phosphate formulation: the purified antibody was concentrated in formulation buffer (10 mM $Na_2PO_4$, 40 mM NaCl, 0.03% polysorbate 20, 5% sucrose, pH 6.3) by ultrafiltration to 100 mg/mL to 200 mg/mL.

Samples of the H3K in the phosphate formulation were subjected to Coomassie SDS-PAGE (4-12% BIS-Tris-MOPS) as follows. The results are shown in FIG. 4, which illustrates the analysis of purified bifunctional antibody. In FIG. 4A, the lanes were loaded as follows: L, ladder; 1, purified rh-anti-HDGF H3-VEGF trapper (non-reducing, 40 μg); 2, purified rh-anti-HDGF H3-VEGF trapper (reducing, 40 μg). In FIG. 4B, the lanes were loaded as follows: L, ladder; 1, rh-anti-HDGF H3-VEGF trapper only; 2, rh-anti-HDGF H3-VEGF trapper plus VEGF-mCherry; 3, rh-anti-HDGF H3-VEGF trapper plus HDGF; 4, rh-anti-HDGF H3-VEGF trapper plus VEGF-mCherry plus HDGF.

B. Biologically Active Fragments and Variants

As indicated above, the term "antibody" as used herein, unless otherwise stated or clearly contradicted by context, includes any fragment of an antibody that retains the ability to specifically interact, for example bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_{H1}$ domains, or a monovalent antibody as described in WO2007059782 (Genmab A/S); (ii) F(ab')$_2$ fragments, bivalent fragments comprising two Fab fragments linked by a disulfide bridge at the hinge region; (iii) a Fd fragment consisting essentially of the $V_H$ and $C_{H1}$ domains; and (iv) a Fv fragment consisting essentially of the $V_L$ and $V_H$ domains of a single arm of an antibody. Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

"Biologically active fragments" of an antibody as used herein, mean any fragment that retains binding affinity for HDGF. The fragments retain one or more CDR regions from the original antibody. CDRs are the sites of the antibody that bind to the antigen and in most cases are unique to that antibody. For a fragment to retain binding to the antigen, it would need to have at a set of CDRs with 3D structure such that they are combined to form a binding pocket or the like.

Biologically active fragments may also contain minor variations provided that the variations in the amino acid sequence maintain at least 75%, more preferably at least 80%, 90%, 95%, and most preferably 99% sequence identity and the molecule retains its affinity for binding.

"Variants" of a bi-functional chimeric antibody or fragment thereof include amino acid sequence modification(s) of the antibodies described herein that may, for example, improve the binding affinity and/or other biological properties of the antibody for the intended purpose of treating or mitigating an enumerated disease. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired affinity for HDGF. The amino acid alterations may be introduced in the subject antibody amino acid sequence at the time that sequence is made.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

C. Pharmaceutical Compositions

In some embodiments, pharmaceutical compositions comprising the bifunctional hepatoma-derived growth factor (HDGF)-specific antibody with a pharmaceutically acceptable carrier are provided. The pharmaceutical composition may be formulated for parenteral, intravenous, intraocular, or topical administration, or can be formulated as eye drops. Preferably the pharmaceutical composition is formulated for administration by intraocular injection in an amount from about 0.5 mg to about 10 mg per eye every 5-60 days. Most preferably the intraocular injection is in an amount of about 2 mg per eye every 6-10 days. The pharmaceutical compositions may be formulated with pharmaceutically acceptable carriers or diluents as well as any other known adjuvants and excipients in accordance with conventional techniques known in the art.

The pharmaceutically acceptable carriers or diluents as well as any other known adjuvants and excipients should be suitable for the humanized or chimeric antibodies of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding and on safety for the subject.

Pharmaceutically acceptable carriers include any and all suitable solvents, dispersion media, coatings, antibacterial and antifungal agents, isotonicity agents, antioxidants and absorption-delaying agents, and the like that are physiologically compatible with a humanized or chimeric antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Ointments also are known in the art and can be used as a carrier for embodiments of the invention. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. When referring to the "active compound" it is contemplated to also refer to the humanized or chimeric antibody according to the present invention.

Suitable formulations for use as eye drops can include solutions, emulsions or suspensions. Intraocular injection formulas can be prepared using, for example, sterile solutions, suspensions, or intraocular implants for delivery to the vitreous cavity. Any known carrier suitable for application to or into the eye is contemplated for use with the invention, including any known in the art.

Proper fluidity may be maintained, for example, using coating materials such as lecithin, by maintaining the required particle size in the case of dispersions, and by using surfactants.

A pharmaceutical composition of the present invention may also include diluents, fillers, salts, buffers, detergents, stabilizers, preservatives, solubilizers, pH adjusters, solvents, emulsifiers, thickeners, and/or other materials suitable for inclusion in a pharmaceutical composition, particularly formulations for use in or on the eye.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition can be administered by any suitable route and mode. Suitable routes of administering a humanized or chimeric antibody of the present invention in vivo and in vitro are well known in the art and may be selected by those of ordinary skill in the art.

In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intra-arterial, intrathecal, intracapsular, intra-orbital (intraocular), intracardiac, intradermal, intraperitoneal, intratendinous, local injection, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion. The pharmaceutical compositions of the present invention may also contain one or more adjuvants appropriate for the chosen route of administration such as preservatives, wetting agents, emulsifying agents, dispersing agents, preservatives, or buffers, which may enhance the shelf life or effectiveness of the pharmaceutical composition. The humanized or chimeric antibody of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-orthoesters, and polylactic acid alone or with a wax, or other materials well known in the art. Methods for the preparation of such formulations are generally known to those skilled in the art.

In one embodiment, the humanized or chimeric antibody of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g., as enumerated above, as required, followed by sterilization microfiltration. Generally, dispersions are prepared by incorporating the active compound into a sterile vehicle that contains a basic dispersion medium and the required other ingredients e.g., from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Formulations for eye formulations generally are prepared as sterile solutions, suspensions, and emulsions, however ointments, gels, and the like, also may be used, incorporating the active compound in an amount for effective treatment of the eye. Such pharmaceutical compositions and formulations are known in the art and can be devised by a person of skill in the pharmaceutical arts.

D. Therapeutic Applications

Chimeric antibodies have been developed for therapeutic use. Representative publications related to such therapies include Chamow et al., 1996, Trends Biotechnol. 14:52-60; Ashkenazi et al., 1997, Curr. Opin. Immunol. 9:195-200, Cragg et al., 1999, Curr. Opin. Immunol. 11:541-547; Glennie et al., 2000, Immunol. Today 21:403-410, Mclaughlin et al., 1998, J. Clin. Oncol. 16:2825-2833, and Cobleigh et al., 1999, J. Clin. Oncol. 17:2639-2648, all entirely incorporated by reference. Currently for anticancer therapy, any small improvement in mortality rate defines success. Certain IgG variants disclosed herein enhance the capacity of antibodies to limit further growth or destroy at least partially, targeted cancer cells.

Anti-tumor potency of antibodies is via enhancement of their ability to mediate cytotoxic effector functions such as ADCC, ADCP, and CDC. Examples include Clynes et al., 1998, Proc. Natl. Acad. Sci. USA 95:652-656; Clynes et al., 2000, Nat. Med. 6:443-446 and Cartron et al., 2002, Blood 99:754-758, both entirely incorporated by reference.

Human IgG1 is the most common antibody used for therapeutic purposes, and the majority of engineering studies have been constructed in this context. The different isotypes of the IgG class however, including IgG1, IgG2, IgG3, and IgG4, have unique physical, biological, and clinical properties. There is a need in the art to design improved IgG1, IgG2, IgG3, and IgG4 variants. There is a further need to design such variants to improve binding to FcRn and/or increase in vivo half-life as compared to native IgG polypeptides. The present application meets these and other needs.

Further embodiments include methods reducing the growth of hyperproliferative cells in a subject by administering to the subject the bifunctional hepatoma-derived growth factor (HDGF)-specific antibody in an amount of that down regulates HDGF and VEGF expression or HDGF and TGFβ expression or both VEGF and TGFβ expression and is effective to reduce the abnormal growth of the hyperproliferative cells. It is possible to co-administer a mixture of these antibodies (i.e., H3K+H3T) or with other antibody-based drugs such as Cetuximab or Herceptin. In some embodiments, the hyperproliferative cell may be a fibroblast, or a cancer cell, or a vascular endothelia cell. The cancer cell may be selected from the group consisting of lung, pancreas, colon, ovarian, liver, glioblastoma, and squamous cell carcinoma.

In some embodiments, methods are provided for simultaneously reducing expression of HDGF and VEGF or HDGF and TGFβ in a subject in need thereof by administering bifunctional hepatoma-derived growth factor (HDGF)-specific antibody. The subject in need suffers from a hyperproliferative condition selected from the group consisting of interstitial lung disease, keloids, lung fibrosis, idiopathic pulmonary fibrosis, lung cancer, pancreatic cancer, colon cancer, ovarian cancer, liver cancer, glioblastoma, diabetic retinopathy, age-related macular degeneration, and squamous cell carcinoma.

In another aspect, the present invention relates to a humanized or chimeric antibody, or pharmaceutical composition of the invention as defined in any aspect or embodiment herein described, for use in the treatment of a disease.

The humanized or chimeric antibody or pharmaceutical composition of the invention can be used as in the treatment of any cancer and certain ocular pathologies. For example, the humanized or chimeric antibody may be administered to cells in culture, e.g., in vitro or ex vivo, or to human subjects, e.g., in vivo, to treat or prevent disorders such as cancer, inflammatory or autoimmune disorders. As used herein, the term "subject" is typically a human which respond to the humanized or chimeric antibody, or pharmaceutical composition. Subjects may for instance include human patients having disorders that may be corrected or ameliorated by modulating a target function or by leading to killing of the cell, directly or indirectly. In certain embodiments, the subject is a mammal, for example a human, that suffers from an ocular pathology such as diabetic retinopathy, age-related macular degeneration, neovascular age-related macular degeration, peripheral vitreoretinopathy, reginal vein occlusion, and the like, and in particular neovascular age-related macular degeneration or diabetic retinopathy.

In another aspect, the present invention provides methods for treating or preventing a hyperproliferative condition, such as keloids or lung fibrosis or diabetic retinopathy, or age-related macular degeneration, which method comprises administration of a therapeutically effective amount of a humanized or chimeric antibody, or pharmaceutical composition of the present invention to a subject in need thereof. The method typically involves administering to a subject a humanized or chimeric antibody in an amount effective to treat or prevent the disorder.

In one particular aspect, the present invention relates to a method of treatment of lung cancer comprising administering the humanized or chimeric antibody or pharmaceutical composition of the invention as defined in any aspect and embodiments herein described, to a subject in need thereof. In another particular aspect, the present invention relates to a method of treatment or use for treatment of an ocular pathology such as, diabetic retinopathy, neovascular age-related macular degeneration, and the like.

In another aspect, the present invention relates to the use or the method as defined in any aspect or embodiments herein described wherein the humanized or chimeric antibody is a bi-functional antibody specifically binding to both VEGF or TGFβ or both and a cancer-specific target, or a target that is overexpressed in cancer or associated with cancer, such as HDGF and wherein the disease is cancer, such as breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, a soft-tissue cancer (e.g., synovial sarcoma), an indolent or aggressive form of B-cell lymphoma, chronic lymphatic leukemia or acute lymphatic leukemia.

E. Dosage and Administration

The efficient dosages and dosage regimens for the targeting protein composition depend on the disease or condition to be treated and may be determined by the persons skilled in the art and the route of administration.

A physician having ordinary skill in the art may readily determine and prescribe the effective amount of the pharmaceutical composition required. For example, the physician could start doses of the humanized or chimeric antibody employed in the pharmaceutical composition at levels lower than that required in order to achieve the desired therapeutic effect and gradually increase the dosage until the desired effect is achieved. In general, a suitable dose of a composition of the present invention will be that amount of the humanized or chimeric antibody which is the lowest dose effective to produce a therapeutic effect according to a particular dosage regimen. Such an effective dose will generally depend upon the factors described above.

For example, an "effective amount" for therapeutic use may be measured by its ability to stabilize or slow progression of disease. The ability of a compound to inhibit cancer may, for example, be evaluated in an animal model system predictive of efficacy in human tumors. Alternatively, this property of a composition may be evaluated by examining the ability of the humanized or chimeric antibody to inhibit cell growth or to induce cytotoxicity by in vitro assays known to the skilled practitioner. A therapeutically effective amount of a therapeutic compound, i.e., a therapeutic humanized or chimeric antibody, or pharmaceutical composition according to the invention, may decrease tumor size, or otherwise ameliorate symptoms in a subject. One of ordinary skill in the art would be able to determine such amounts based on such factors as the subject's size, the severity of the subject's symptoms, and the particular composition or route of administration selected.

With respect to an ocular pathology, disease or condition, a therapeutically effective amount of the compounds of the invention includes amounts, doses, series of doses, and dosage regimens that slow progression of the ocular disease, halt progression of the disease, improve the condition of the subject or the subject's vision, improvement of the disease symptoms, or cure the condition. Improvements in the condition of the subject of this type may not occur after the first administration of the inventive compounds, but occur after a series of doses. The administration of several doses over days, weeks, months, years, or a lifetime, may constitute a therapeutically effective amount.

An exemplary, non-limiting range for a therapeutically effective amount of a humanized or chimeric antibody of the invention for treatment of the eye comprises doses of about 0.5 mg to about 25 mg, such as about 1 mg to about 20 mg or about 1 mg to about 10 mg. More preferred amounts for a dose is about 1 mg to about 5 mg, and most preferably about 1 mg to about 2 mg. Most preferably, the dose is about 2 mg of the targeting protein composition. The composition most preferably is delivered by intraocular injection.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In one embodiment, the efficacy of the treatment is monitored during the therapy, e.g., at predefined points in time.

If desired, an effective daily dose of a pharmaceutical composition may be administered as two, three, four, five, six or more sub-doses administered separately at appropriate intervals throughout the day, optionally, in unit dosage forms, or using a dropper or squeeze bottle to administer eye drops. The container for the pharmaceutical formulation can be single use or multiple use, and the formulation can be a solution, suspension, dispersion ointment, or the like as are known in the art. In another embodiment, the humanized or chimeric antibody, or pharmaceutical composition is administered by slow continuous infusion over a long period, such as more than 24 hours, for example to minimize any unwanted side effects.

While it is possible for a humanized or chimeric antibody of the present invention to be administered alone, it is preferable to administer the humanized or chimeric antibody with a pharmaceutically acceptable carrier as a pharmaceutical composition as described above.

An effective dose of a humanized or chimeric antibody of the invention preferably is administered by intraocular injection on a schedule, including weekly, every 2 weeks, every 3 weeks, every 4 weeks, every 5 weeks, every 6 weeks, or every 8 weeks. The dosing period may be restricted to, e.g., 8 weeks, 12 weeks, 6 months, or until clinical progression has been established, or it can be administered for an indefinite period. Preferable dosing schedules are about every 3-6 weeks or about every 4 weeks or monthly.

In one embodiment, the humanized or chimeric antibody may be administered by infusion in a weekly dosage of calculated by mg/m$^2$. Dosages can, for example, be based on the mg/kg dosage or by volume and concentration or by weight. Administration may be repeated, e.g., 1 to 8 times, such as 3 to 5 times. The administration may be performed by continuous infusion over a period of from 2 to 24 hours, such as from 2 to 12 hours. In one embodiment, the humanized or chimeric antibody may be administered by slow continuous infusion over a long period, such as more than 24 hours, in order to reduce toxic side effects. Alternatively, the composition can be administered once a day, two or three times per day, four times per day, or more often for a period of one day, one week or longer, including for a period of many weeks or months, or indefinitely.

In one embodiment, the humanized or chimeric antibody may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of humanized or chimeric antibody of the present invention in the blood or tears upon administration by for instance taking out a biological sample and using anti-idiotypic antibodies which target the binding region of the humanized or chimeric antibodies of the present invention.

In one embodiment, the humanized or chimeric antibody may be administered by maintenance therapy, such as, e.g., once a week, or any interval for a period of days, weeks, months, 6 months, a year, many years or indefinitely.

A humanized or chimeric antibody may also be administered prophylactically in order to reduce the risk of developing an ocular pathology, delay the onset of the occurrence of an event in ocular pathology progression, and/or reduce the risk of recurrence when a pathology is in remission.

Parenteral compositions may be formulated in dosage unit form for case of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specifications for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Pharmaceutical compositions comprising a humanized or chimeric antibody according to the present invention will be formulated as solutions, suspensions, or other dosage forms for topical ophthalmic administration in a pharmaceutically acceptable carrier, adjuvant, or vehicle for treatment of any ocular pathology, such as diabetic retinopathy and age-related macular degeneration. Preferred embodiments include aqueous solutions due to their case of formulation, as well as a subject's ability to easily administer these compositions to the eye, for example via one to two drops of the solution, suspension, or emulsion in the affected eyes. The compositions, however, may also be suspensions, viscous or semi-viscous gels, ointments, or other types of solid or semi-solid compositions. Additional ingredients that may be included in the formulation include carriers, tonicity enhancers, preservatives, solubilizers, non-toxic excipients, demulcents, sequestering agents, pH adjusting agents, co-solvents, viscosity binding agents, liposomes, and the like.

A humanized or chimeric antibody may also be administered prophylactically in order to reduce the risk of developing a hyperproliferative condition or ocular pathology (e.g., lung fibrosis, keloids, interstitial lung disease, lung cancer, diabetic retinopathy, or macular degeneration), delay the onset of the occurrence of an event in cancer progression or progression of an ocular pathology, and/or reduce the risk of recurrence when a cancer is in remission. This may be especially useful in patients wherein it is difficult to locate a tumor that is known to be present due to other biological factors.

F. Diagnostic Applications

The humanized or chimeric antibody of the invention may also be used for diagnostic purposes, using a composition comprising a humanized or chimeric antibody as described herein. Accordingly, the invention provides diagnostic methods and compositions using the humanized or chimeric antibodies described herein. Such methods and compositions can be used for purely diagnostic purposes, such as detecting or identifying a disease, as well as for monitoring of the progress of therapeutic treatments, monitoring disease progression, assessing status after treatment, monitoring for recurrence of disease, evaluating risk of developing a disease, and the like.

In one aspect, the humanized or chimeric antibody of the present invention is used ex vivo, such as in diagnosing a disease in which cells expressing a specific target of interest and to which the humanized or chimeric antibody binds, are indicative of disease or involved in the pathogenesis, by detecting levels of the target or levels of cells which express the target of interest on their cell surface in a sample taken from a patient. This may be achieved, for example, by contacting the sample to be tested, optionally along with a control sample, with the humanized or chimeric antibody according to the invention under conditions that allow for binding of the antibody to the target. Complex formation can then be detected (e.g., using an ELISA). When using a control sample along with the test sample, the level of humanized or chimeric antibody or antibody-target complex is analyzed in both samples and a statistically significant higher level of humanized or chimeric antibody or antibody-target complex in the test sample indicates a higher level of the target in the test sample compared with the control sample.

Examples of conventional immunoassays in which humanized or chimeric antibodies of the present invention can be used include, without limitation, ELISA, RIA, FACS assays, plasmon resonance assays, chromatographic assays, tissue immunohistochemistry, western blot, and/or immunoprecipitation, immunofluorescent assay methods including microarrays.

Accordingly, in one embodiment, the present invention relates to a method of diagnosing a disease characterized by involvement or accumulation of HDGF-expressing cells, comprising administering an antibody, bispecific antibody, composition or pharmaceutical composition according to any aspect or embodiment herein described, to a subject, optionally wherein the antibody is labeled with a detectable label.

In one embodiment, the invention relates to a method for detecting the presence of a target, or a cell expressing the target, in a sample comprising: contacting the sample with a humanized or chimeric antibody of the invention under conditions that allow for binding of the humanized or chimeric antibody to the target in the sample; and analyzing whether a complex has been formed. Typically, the sample is a biological sample.

In one embodiment, the sample is a tissue sample known or suspected of containing a specific target and/or cells expressing the target, a non-tissue sample or fluid with or without cells. For example, in situ detection of the target expression may be accomplished by removing a histological specimen from a patient and providing the humanized or chimeric antibody of the present invention to such a specimen. The humanized or chimeric antibody may be provided by applying or by overlaying the humanized or chimeric antibody to the specimen, which is then detected using suitable means. It is then possible to determine not only the presence of the target or target-expressing cells, but also the distribution of the target or target-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the humanized or chimeric antibody can be labeled with a detectable substance to allow bound antibody to be detected. Alternatively, bound (primary) specific humanized or chimeric antibody may be detected by an antibody which is labeled with a detectable substance and which binds to the primary specific humanized or chimeric antibody. Furthermore, in the above assays, a diagnostic composition comprising an antibody or bispecific antibody according to any aspect or embodiments herein described may be used. Thus, in one aspect, the present invention relates to a diagnostic composition comprising an antibody or bispecific antibody according to any aspect or embodiment herein described.

Suitable labels for the target-specific humanized or chimeric antibody, secondary antibody and/or target standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}I$, $^{131}I$, $^{35}S$, and $^{3}H$.

G. Kits

The invention also provides kits (or articles of manufacture) for use in the treatment of the disorders described above. Kits of the invention include one or more containers comprising a purified engineered polypeptide conjugate and instructions for using the conjugate for treating a disease. For example, the instructions comprise a description of administration of the engineered polypeptide conjugate to treat a disease, such as cancer (e.g., colon, esophageal, gastric, head and neck, lung, ovarian, or pancreatic cancer) or an ocular pathology. The kit may further comprise a description of selecting an individual suitable for treatment based on identifying whether that individual has the disease and the stage of the disease.

The instructions relating to the use of the engineered polypeptide conjugate generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, single-use squeeze droppers, jars, flexible packaging (e.g., sealed Mylar or plastic bags), and the like. Also contemplated are packages for use in combination with a specific device, such as a dropper, an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an engineered polypeptide as described herein. The container may further comprise a second pharmaceutically active agent.

Kits may optionally provide additional components such as buffers and interpretive information. Normally, the kit comprises a container and a label or package insert(s) on or associated with the container.

Thus, in one aspect, the present invention provides a kit for detecting the presence of a growth factor (HDGF, VEGF, and TGFβ) in a sample comprising the steps of;
a) contacting the sample with an antibody or bispecific antibody according to the invention, under conditions that allow for formation of a complex between the antibody or bifunctional antibody and the target of interest; and b) analyzing whether a complex has been formed. In some embodiments, anti-human or anti mouse IgG antibodies may be used to detect binding. It is possible to also use the antibody in certain types of array or micro-fluidic device which can use electron-optical method to detect the binding. An example of this is surface plasmon resonance or other methods based on surface interaction and optical or surface atomic force scanning.

In one embodiment, the present invention provides a kit for diagnosis of cancer comprising a container comprising a target-specific humanized or chimeric antibody, and one or more reagents for detecting binding of the target-specific humanized or chimeric antibody to the target. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more target-specific humanized or chimeric antibodies of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with a target-specific humanized or chimeric antibody, such as a labeled target-specific antibody, for the detection of the presence of the target in a tissue sample or host. In such diagnostic kits, as well as in kits for therapeutic uses described elsewhere herein, a target-specific humanized or chimeric antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the target-specific humanized or chimeric antibody, which typically is present in a separate container, is also included. The second antibody is typically conjugated to a label and formulated in a manner similar to the target-specific humanized or chimeric antibody of the present invention. Using the methods described above and elsewhere herein, target-specific humanized or chimeric antibodies may be used to define subsets of cancer/tumor cells and characterize such cells and related tumor tissues.

H. Therapeutic Agents

Many therapeutic agents are available that can be conjugated to an antibody or used in conjunction with antibody therapies described herein. In embodiments, therapeutic agents, including, but not limited to, lubricants, numbing agents, anti-redness agents, anti-itch agents, moisturizers, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the antibody/peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents and combinations thereof. Other examples include paclitaxel, docetaxel, doxorubicin, cis platinum, and ricin.

In the following description, for the purposes of explanation, numerous specific details are set forth in order to provide a thorough understanding of the present invention. It will be apparent, however, to one skilled in the art that the present invention may be practiced without these specific details. In order that the invention may be readily understood and put into practical effect, particular preferred embodiments will now be described by way of the following non-limiting examples.

6. Examples

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1. Production of Anti-HDGF Antibody Secreting Hybridoma Clones C1, C4, H3, and L5-9

To explore a bi-functional antibody-based therapeutic strategy, a panel of anti-HDGF antibodies (HDGF-C1, -C4, -H3, and L5-9) as previously described in Table 1 were created to bind native HDGF. In some embodiments, the antibodies are IgG1 and recognize HDGF and can recognized modified forms or variants, or fragments of HDGF. The cDNA fragment that encodes HDGF was PCR amplified and cloned into pGEX-4-T1 vector (GE Health Care, Piscataway, NJ). The resulting plasmid, pGST-HDGF, was used to generate GST-HDGF fusion protein in *E. coli* strain BL21 (DE) 3. The recombinant protein was purified using GST affinity chromatography. Balb/c mice were then immunized with the fusion protein and boosted twice. Three days after the last boost, mice were sacrificed and splenocytes were fused with P3X63Ag8.653 cells followed by culturing in selecting medium. Anti-HDGF antibody secreting hybridoma clones were identified and verified. For large scale antibody production, hybridoma cells were cultured in RPMI 1640 supplemented with Nutridoma™ CS (Roche™ Applied Science, Indianapolis, IN). The antibodies were purified using protein G-agarose (GE Health Care) affinity chromatograph. Purified antibody was then dialyzed and sterile filtered through a 0.22 μm filter. Sequence analysis produced the following amino acid sequences of antibody clones C1, C4, H3, and L5-9 set forth below in Table 3.

TABLE 3

| Amino Acid Sequences of Antibody Clones C1, C4, H3, and L5-9 |
| --- |

Variable domains of anti-HDGF antibody clones
H3, C1, C4, and L5

2.1 Clone H3

| 2.1.1 H3HD4 (H3 heavy chain) | MGRLTSSFLLLVVPIYVLSQITLKQSGPGIVQPSQPVRLTCTFSGFSLSTSGI GVAWIRQPSGKGLEWLATIWWDDDNRYNPSLKSRLAVSKDTSNNQAFL NIITVETADTAIYYCAQIYDYAVGFAYWGQGTLVTVSAAKTTPPSVYPLA PGSLGRAN (SEQ ID NO: 9) |
| --- | --- |
| 2.1.2 H3LF2 (H3 light chain) | MVSTAQFLGLLLLCFQGTRCDIQMIQTTSSLSASLGDRVTISCRASQDISN YLNWYQQKPDGTVKLLIYYTSRLHSGVPSRFSGSGSGTDYSLTISNLEPDD IATYYCQQYGKLWTFGGGTKLEIKRADAAPTVSIFPPPSSKLGKGEF (SEQ ID NO: 10) |

2.2 Clone C1

| 2.2.1 C1HA5 (C1 heavy chain) | MNLGLSWIFFAVFYQGVHCEVQLVESGGRLVQPKGSLKLSCAASGFTFN TYAMYWIRQAPGKGLEWVARIRSKSYNYATYYADSVKDRFTISRDDSQS MSYLQMNNLKTADTAMYYCVSEGFWGQGTSVTVSSAKTTPPSVYPLVP GSLGRANSADIHHTG (SEQ ID NO: 11) |
| --- | --- |
| 2.2.2 C1LG1 (C1 light chain) | MKLPVRLLVLMFWIPASSSDVLMTQTPLSLPVSLGDQASISCRSSQSIVHS SGNTYLEWYLQKPGQSPKLLIYKVSNRFSGVPDRFSGSGSGTDFTLKISRV EAEDLGVYYCFQGSHVPWTFGGGTKLEIKRADAAPTVSIFPPPSSKLGKGE F (SEQ ID NO: 12) |

2.3 Clone C4

| 2.3.1 C4HD1 (C4 heavy chain) | MDRLTSSFLLLIVPAYVLSQVTLKESGPGILQPSQTLSLTCSFSGFSLSTSG MGVGWIRQPSGKGLEWLAHIWWDDVKRFNPDLKSRLTISKDTSSAQVFL KIASVDTADTATYYCTRIEDYDGALDYWGQGTSVTVSSAKTTPPSVYPLA PGSLGRAN (SEQ ID NO: 13) |
| --- | --- |
| 2.3.2 C4LA1 (C4 light chain) | MESQSQVFLSLLLWVSGTCGNIMMTQSPSSLAVSTGEMVTMSCKSSQSV LYSSNQKNYLAWFQQTPGQSPKLLIYWASTRESGVPDRFTGSGSGTDFTL TISNVQAADLAVYYCHQYLSSWTFGGGTKLEIKRADAAPTVSIFPPPSSKLG KGEF (SEQ ID NO: 14) |

2.4 clone L5 (also marked as L5-9)

| 2.4.1 L5HB-1 (L5 heavy chain) | MKWSWVFLFLVATATGVRSQVQLQQPGAELVKPGASVKLSCKASGYTF TSYWIHWVKQRPGQGLEWIGNINPNSGSTDNNEKFTSKATLTVDTSSSTA YMQLSSLTSEDSAVYYCTTLLGRTGFAYWGQGTLVTVSAAKTTPPSVYP LAPGSLGRAN (SEQ ID NO: 15) |
| --- | --- |

TABLE 3-continued

Amino Acid Sequences of Antibody Clones C1, C4, H3, and L5-9

Variable domains of anti-HDGF antibody clones
H3, C1, C4, and L5

| | |
|---|---|
| 2.4.2 L5LD1<br>(L5 light chain) | MRAPAQILGILLLWFPGIKCDIKMTQSPSSMYASLGERVTITCKASQDINS<br>YLSWFQQKPGKSPKTLIYRANRLLDGVPSRFSGSGSGQDYSLTISSLEYED<br>LGIYYCLQYDEFPLTFGAGTKLELKRADAAPTVSIFPPSSKLGKGEF (SEQ<br>ID NO: 16) |

Example 2. Humanized Anti-HDGF H3 Antibody (hH3)

The humanized anti-HDGF H3 (hH3) was created by grafting the complement determent region (CDR) of mouse H3 to a human IgG1 framework. Methods for making monoclonal mouse H3 antibody are described in Ren, H., et al., "Antibodies targeting hepatoma-derived growth factor as a novel strategy in treating lung cancer," Mol. Cancer Ther. 2009 May; 8 (5): 1105-1112.

Humanization of H3 was performed to generate a humanized H3 (hH3) monoclonal antibody by the CDR grafting method. Usually, rodent antibodies can be immunogenic to human and cause very serious side effects including the HAMA (human anti-mouse antibodies) response or anaphylactic shock. With this CDR grafting approach, CDR loops that make up the antigen-binding site of the mouse Mab are grafted into corresponding human framework regions. Initially, the variable light and heavy chain sequences of H3 were determined as shown in Table 3. To do so, H3 hybridoma cells were harvested by centrifugation and total RNA was extracted from cells. Total RNA was used for cDNA synthesis, and V-region genes of H3 were amplified, cloned and sequenced using standard primer sets.

Figure 5:
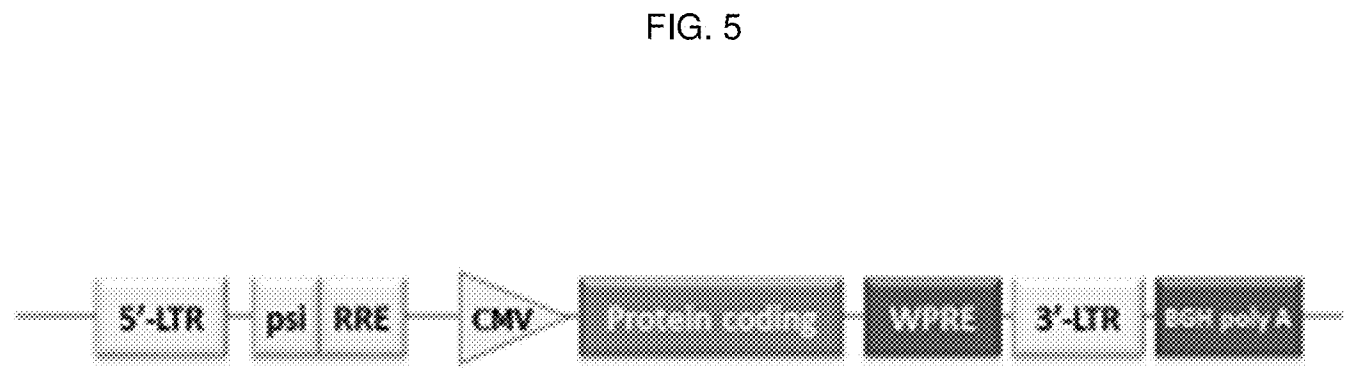

CDR sequences were grafted into these VL and VH, such that the synthesized sequences each CDRs in the selected human framework sequences. To construct humanized H3 IgG1 in a mammalian expression vector, pLVBHN vectors were used. The following is a brief vector map. The vector was synthesized from several sources (e.g., see FIG. 5). However, it can be expressed from any mammalian expression vectors. The backbone of the vector for expression of recombinant antibody is modified from pTRIPZ (Open biosystems or GE Dharmacon™), including LTR, psi, RRE, WPRE; the CMV promoter is from pHTN (Promega™). However, any mammalian expression vector can be used to express the recombinant antibody. Transient transfection was used using Expi293 system from Invitrogen™. Sequences are provided below in Table 4.

TABLE 4

Humanized H3 Sequences 2.1 Humanized H3 heavy chain variable region,
mature sequence.
　　　　　　　　　　　　　　　　　　　　SEQ ID NO: 17
QITLKESGPTLVKPTQTLTLTCTFSGFSLSTSGIGVAWIRQPPGKALE

WLATIWWDDDNRYNPSLKSRLTITKDTSKNQVVLTMTNMDPVDTATYY

CAQIYDYAVGFAYWGQGTLVTVSS.

TABLE 4-continued

Humanized H3 Sequences 2.2 Humanized H3 light chain variable region,
mature sequence.
　　　　　　　　　　　　　　　　　　　　SEQ ID NO: 18
DIQMTQSPSSLSASLGDRVTISCRASQDISNYLNWYQQKPGKAPKLLI

YYTSRLHSGVPSRFSGSGSGTDYSLTISSLQPEDIATYYCQQYGKLWT

FGQGTKLE.

2.3 Humanized H3 heavy chain, mature sequence.
　　　　　　　　　　　　　　　　　　　　SEQ ID NO: 19
QITLKESGPTLVKPTQTLTLTCTFSGFSLSTSGIGVAWIRQPPGKALE

WLATIWWDDDNRYNPSLKSRLTITKDTSKNQVVLTMTNMDPVDTATYY

CAQIYDYAVGFAYWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMH

EALHNHYTQKSLSLSPGK.

2.4 Humanized H3 light chain, mature sequence.
　　　　　　　　　　　　　　　　　　　　SEQ ID NO: 20
DIQMTQSPSSLSASLGDRVTISCRASQDISNYLNWYQQKPGKAPKLLI

YYTSRLHSGVPSRFSGSGSGTDYSLTISSLQPEDIATYYCQQYGKLWT

FGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC.

Example 3: Construction of Chimeric H3 Antibody (cH3)

The chimeric H3 was constructed by fusing the variable domain of mouse anti-HDGF H3 with human IgG1 constant region. Sequences are provided below in Table 5.

TABLE 5

Chimeric H3 sequences with variable domain from
mouse and human IgG1 constant region.

3.1 Heavy chain.

SEQ ID NO: 21

MVSTAQFLGLLLLCFQGTRCQITLKQSGPGIVQPSQPVRLTCTFSGFS

LSTSGIGVAWIRQPSGKGLEWLATIWWDDDNRYNPSLKSRLAVSKDTS

NNQAFLNIITVETADTAIYYCAQIYDYAVGFAYWGQGTLVTVSSASTK

GPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKN

QVSLTCLVKGFYPSDIAVEWESNGQPENNYKTTPPVLDSDGSFFLYSK

LTVDKSRWQQGNVFSCSVMHEALHNHYTQKSLSLSPGK.

3.2 Light chain.

SEQ ID NO: 22

MVSTAQFLGLLLLCFQGTRCDIQMTQTTSSLSASLGDRVTISCRASQD

ISNYLNWYQQKPDGTVKLLIYYTSRLHSGVPSRFSGSGSGTDYSLTIS

NLEPDDIATYYCQQYGKLWTFGGGTKLEIKRTVAAPSVFIFPPSDEQL

KSGTASVVCLLNNFYPREAKVQWKVDNALQSGNSQESVTEQDSKDSTY

SLSSTLTLSKADYEKHKVYACEVTHQGLSSPVTKSFNRGEC.

Example 4: Construction of Chimeric Bifunctional Antibodies H3K and H3T

Method of Generating Anti-HDGF Hybridomas

Balb/c mice were immunized with recombinant HDGF in freund's adjuvant. Splenocytes from immunized animals were fused with P3x63Ag8.653 cells and screened for HDGF reactivity in the culture supernatant. Positive clones were identified and anti-HDGF antibody secretion was verified by immunoblot analysis of cancer cell lysate and purified HDGF.

Determination of the Amino Acid Sequences of Anti-HDGF Antibody

RNA from anti-HDGF antibody producing hybridoma was extracted, reverse transcribed into cDNA. Primers designed to amplify the Ig variable region (Larrick, J. W., et al. 1989. Biochem. Biophys. Res. Comm. 160, 1250. Jones, S. T. and Bendig, M. M. 1991. Biotechnology 9, 88.) were used to amplify the cDNA encoding the mouse Ig heavy and light chain. The amplified product were cloned and sequenced. The cDNA sequence that encoded the murine Ig heavy chain and light chain, and the CDRs were identified as described in http://www.bioinf.org.uk/abs/.

Generation of the Chimeric Antibody

The DNA fragment s that encoded the murine antibody variable domain (VH and VL) were grafted to the N-terminal of the constant region of their human IgG1 count part by standard molecular biology techniques, and cloned into a mammalian expression vector respectively. To produce the chimeric antibody, plasmids encoding for the heavy and light chain were co-transfected into Expi293 cells (Invitrogen) at a ratio of 1:2. The antibody was purified from the conditioned media by protein G affinity chromatograph.

Humanization of the Murine Anti-HDGF Antibody H3

The cDNA sequence that encoded the murine Ig heavy chain and light chain, and the CDRs were identified as described by Martin A.C.R. (http://www.bioinf.org.uk/abs/). The humanized anti-HDGF Vh sequences were then created by replacing the CDRs in human Ig G1 Vh with the corresponding murine CDRs. The DNA sequence that encode the humanized sequence is then synthesized and grafted on the N-termini of the human IgG1 heavy chain constant region, cloned into a mammalian expression vector to generate a humanized Ig heavy chain expression construct. The humanized VL expression construct was created similarly. To produce the humanized anti-HDGF antibody, the plasmids that encode for the heavy and light chain was used to transfect Expi293 cell at a ratio of 1:2. The antibody was purified from the conditioned media by protein G affinity chromatograph.

Construction of Fc-Fused Growth Factor Binding Domain (GF Trapper)

Construction of Fc-VEGF trapper: DNA fragment corresponding to domain 2 and 3 (D2 and D3) of human VEGF receptor 2 (kinase insert domain receptor) amino acid residue 122 to residue 327 (based on NP_002253) was amplified from HEK 293 cDNA. The amplified sequence was fused to the C-terminus of the human IgG1 heavy chain via a poly-GlySer linker, (GlyGlyGlyGlySer)$_2$ (SEQ ID NO:23), or (G4S)2. The full-length anti-HDGF antibody heavy chain-VEGF trapper sequence was cloned into a mammalian expression plasmid.

Construction of Fc-TGFB trapper: DNA fragment corresponding to human TGFBR2 extracellular domain amino acid residue 27 to residue 184 (based on NP_001020018) was amplified from human lung cDNA. The amplified sequence was fused to the C-terminus of the human IgG1 heavy chain via a poly-GlySer linker, (GlyGlyGlyGlySer)$_2$ (SEQ ID NO:23), or (G4S) 2. The full-length anti-HDGF antibody heavy chain-TGFB trapper sequence was cloned into a mammalian expression plasmid.

Production of Recombinant Antibody (Chimeric, and Trapper)

To produce the recombinant anti-HDGF antibody, plasmids encoding for the heavy and light chain were co-transfected into Expi293 cells (Invitrogen) at a ratio of 1:2. The antibody was purified from the conditioned media by protein G affinity chromatograph.

Figure 6:
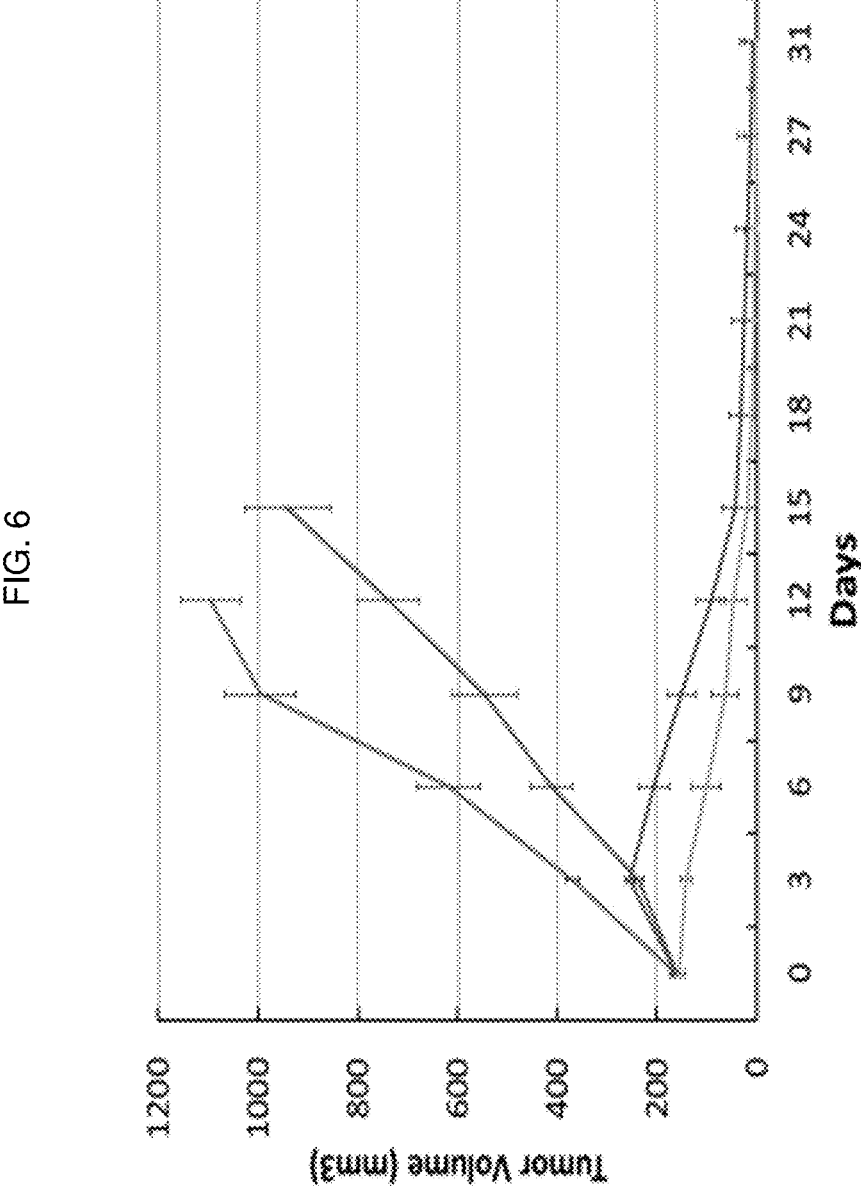
FIG. 6 is a graph illustrating growth curves of PDX model 2131-8 receiving different treatments and showing that anti-HDGF antibody inhibits tumor drug resistance. Human Patient Derived tumor Xenograph (PDX) model 2131-8, a poorly differentiated adenocarcinoma of the lung, was implanted on the flank of athymic nude mice. Established tumors (150-400 mm³, 10 tumors per group) were treated with chemotherapy or combined chemotherapy plus antibody regimen. Arm A (top curve): PBS; Arm B (third top curve): Gemcitabine, 1.2 mg/kg; Arm C (bottom curve): Gemcitabine 1.2 mg/kg plus anti-HDGF H3 at 12.5 mg/kg; Arm D (second top curve): Gemcitabine 1.2 mg/kg plus anti-HDGF H3/VEGF trapper (H3K) at 12.5 mg/kg. The drugs were given intraperitoneally every 3 days until tumor regression or sacrifice due to excess tumor burden.
Figure 7B:
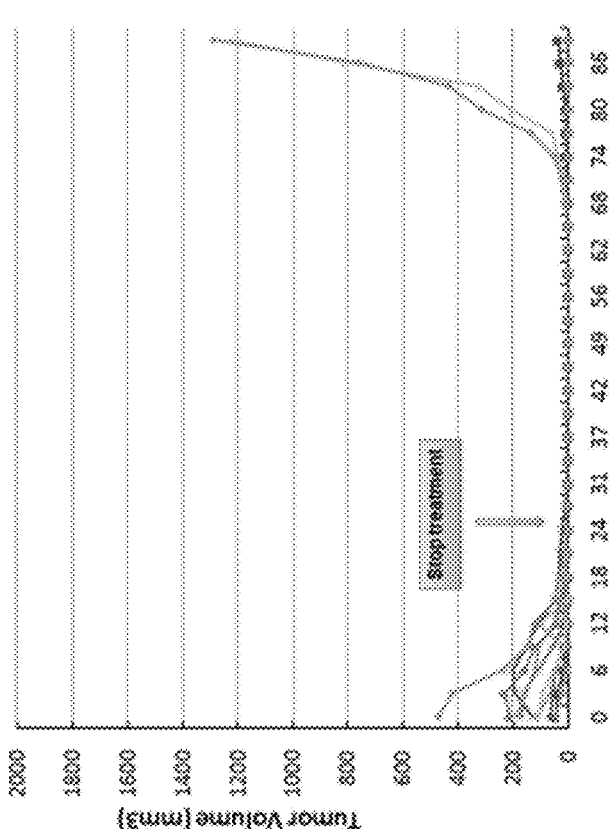
FIG. 7A and FIG. 7B are two graphs illustrating bifunctional antibody-induced extended tumor (volume) remission and plots each individual tumor volume in the ten individuals treated in arm C (FIG. 7A) and arm D (FIG. 7B). Treatments were terminated after complete tumor remission in animals receiving Gemzar™ plus antibody; each curve represents one animal. Arm C: Gemzar™ plus anti-HDFG H3 treated; Arm D: Gemzar™ plus anti-HDGF/VEGF trapper (H3K) treated.
Figure 7A:
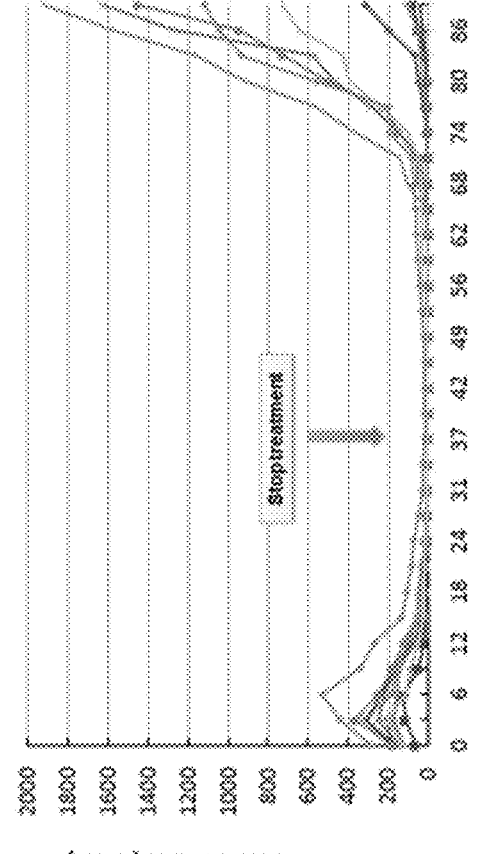

Example 5. Treatment of MDA-2131-8 PDX Cells with H3K Chimeric Bifunctional Antibody Human patient derived tumor xenograph (PDX) model 2131-8, a poorly differentiated adenocarcinoma of the lung, was implanted on the flank of athymic nude mice. As shown in FIG. 6, established tumor (150-400 mm³, 10 tumors per group) were treated with chemotherapy or combined chemo-plus antibody regimen. Arm A: PBS; Arm B: Gemcitabine, 1.2 mg/kg; Arm C: Gemcitabine 1.2 mg/kg plus anti-HDGF H3 at 12.5 mg/kg; Arm D: Gemcitabine 1.2 mg/kg plus anti-HDGF H3/VEGF trapper (H3K) at 12.5 mg/kg. The drugs were given intraperitoneally every 3 days till tumor regression or sacrifice due to excess tumor burden. As shown in FIG. 6, the H3K bifunctional antibody induces extended tumor remission. Treatment was terminated after complete tumor remission in animals receiving Gemzar™ plus antibody. Therapy relapse were monitored. Arm C: Gemzar™ plus anti-HDFG H3 treated; Arm D: Gemzar™ plus anti-HDGF/VEGF trapper (H3K) treated. FIG. 7 shown extended remission in anti-HDGF plus chemo treatment, and even fewer relapse in h3k plus chemo group.

Example 6. Treatment of Bleomycin Induced Lung Fibrosis

Figure 8:
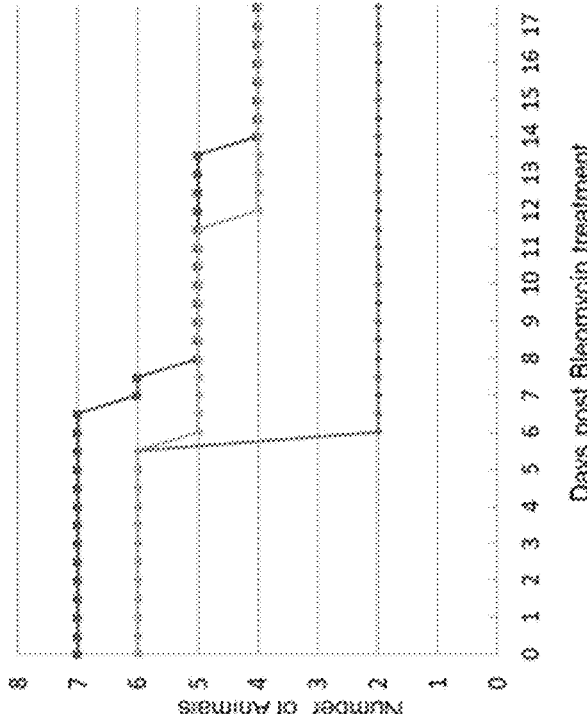
FIG. 8 is a graph illustrating results after treatment with bleomycin (36 ug/animal) given intratracheally to C57/B6 mice (5-6 weeks old, 7 per group) under anesthesia. Antibodies were given twenty-four hours later intraperitoneally in the following treatment groups: (1) control (PBS, diamonds); (2) mouse anti-HDGF H3 plus anti-HDGF C1 125

FIG. 8 illustrates results for mouse survival after bleomycin (36 ug/animal) was given intratracheally to C57/B6 mice (5-6 weeks old, 7 per group) under anesthesia. Antibodies were given twenty-four hours later intraperitoneally in the following treatment groups: 1) mouse anti-HDGF H3 plus anti-HDGF C1 125 ug each (H3+C1); 2) anti-HDGF H3 250 ug plus Avastin 100 μg (H3+A); 3) PBS. The treatments were given every 3 days thereafter for a total 6 doses. Animals were monitored daily. For the data provided in FIG. 9, mice (5-6 weeks old, 7 per group) were primed with antibody intraperitoneally according to the following treatment groups: 1) anti-HDGF H3 plus anti-HDGF C1 125 ug each (H3+C1); 2) chimeric anti-HDGF H3/VEGF trapper plus anti-HDGF C1, 125 ug each (H3K+C1); 3) chimeric anti-HDGF H3/TGFB trapper plus anti-HDGF C1, 125 ug each; 4) PBS control group (PBS). Bleomycin (36 ug/animal) was given intratracheally 24-hours later under anesthesia. Antibodies were again given on day 3 (24-hr post-bleomycin instillation), and every three days thereafter for a total of 7 doses (including priming). Animals were monitored daily.

Bleomycin or PBS was given intratracheally to the lung of C57 mice. Lung tissue was dissected 24 or 48 hours post treatment, and homogenized in lysis buffer with proteinase inhibitors and 1% Triton X-100. Supernatants were separated by SDS gel, blotted on nitrocellulose membrane and stained with anti-HDGF antibodies. Lanes marked 1 indicate PBS-treated lung; lanes marked 2 indicate 24 hours post bleomycin treatment; lanes marked 3 indicate 48 hours post bleomycin treatment, showing significant increase of HDGF expression after tissue injury. See FIG. 10.

These data indicate anti-HDGF antibody, give prior or post bleomycin instilment delayed the onset and reduced the mortality of animals due to lung fibrosis. FIG. 10 shows high-level, sustained HDGF expression after Bleomycin treatment in mouse lung. FIG. 11 shown histological changes in bleomycin treated animals. Hyper-proliferation of fibroblast in mouse lung after bleomycin treatment was seen in untreated or sham (PBS) treated animals (FIG. 11B and FIG. 11C), whereas anti-HDGF treatment reduce the severity of lung fibrosis.

Example 7. Immunoprecipitation of HDGF by Humanized H3K

Humanized H3 was incubated with lung cancer cell lysate to bind HDGF. The immune complex was captured with Protein G beads and analyzed by western blotting. See FIG. 12. The lane marked HH was produced using humanized heavy chain-V trap and humanized light chains; the lane marked HM was produced using humanized heavy chain-V trap and chimeric light chain. FIG. 12A shows staining with mouse anti-HDGF H3 antibody. In FIG. 12B, shows blot re-staining with goat-anti-human IgG HRP conjugate.

Example 8. Human NSCLC PDX Tumor MDA274 Response to Anticancer Therapies

Nude mice carrying human NSCLC PDX tumor MDA274 were subjected to anticancer therapies. Using the methods described in Example 5, above, a second different human patient derived tumor xenograph (PDX) model, also a poorly differentiated adenocarcinoma of the lung, was implanted on the flank of athymic nude mice. Drugs were administered every three days.

As shown in FIG. 13, established tumor (10 tumors per group) were treated with chemotherapy or with combined chemotherapy plus antibody regimen. Tumor volumes were measured every three days. FIG. 13A shows a summary of average tumor volumes after five treatment regimens. Diamonds indicate negative control (PBS) treatment; squares indicate chemotherapy (Gemcitabine, 50 mg/kg, and Pemetrexed, 30 mg/kg); triangles indicate chemotherapy as above plus anti-VEGF antibody. 12.5 mg/kg; X indicates chemotherapy as above plus anti-HDGF antibody, 12.5 mg/kg; asterisk indicates chemotherapy as above plus H3K (anti-HDGF/anti-VEGF bifunctional antibody), 12.5 mg/kg.

FIG. 12B and FIG. 13C show the tumor volumes of individual mice with treatment consisting of chemotherapy as above plus anti-VEGF antibody (FIG. 13B) and chemotherapy as above plus H3K anti-HDGF/anti-VEGF bifunctional antibody. Progression-free survival was routinely observed in the chemotherapy (Gemcitabine/Pemetrexed) plus H3K group (see FIG. 13C).

Example 9. Immunohistochemical Staining

Mice bearing MDA 2131-8 (PDX) tumors were euthanized at 30% and 70% tumor volume reduction and the tumors dissected (about 500 mm$^3$). Thus, tumor tissues at 30% and 70% volume reduction were collected.

The tissues were prepared as follows. The tissues were fixed in 4% formaldehyde-PBS, and embedded in paraffin. Four-micron (4 μm) sections of the embedded tissue were cut, mounted on Superfrost® plus microscope slides. The slides were baked at 55° C., and deparaffined in xylene, followed by rehydration in graded alcohol solutions. The slides then were treated in 50 mM Tris-HCl, pH 8.5 for 30 minutes at 100° C. to retrieve antigen, quenched in 3% hydrogen peroxide and blocked in 1% goat serum. Primary antibody at the manufacture recommended dilution (1:100 to 1:1000) was added and incubated with the tissue section at 4° C. overnight. The following day, the sections were washed with PBS, then developed with VECTORSTAIN ABC® HRP kit or Vector MOM Elite® HRP kit per the manufacture's standard protocol, using diaminobenzidine (DAB) as the chromogenic agent. The developed sections were counterstained with hematoxylin, dehydrated in graded alcohol and xylene, and mounted in Permount® mounting medium. Results are presented in FIG. 14, FIG. 15, and FIG. 16 at magnification 20×.

For FIG. 14, MDA 2131-8 tissue was stained with anti-SOX2 antibody from Cell Signaling Technology® CST3579. FIG. 14A: treatment naïve tumor; FIG. 14B: Gemcitabine plus anti-VEGF treatment at 30% tumor volume reduction; FIG. 14C: Gemcitabine plus H3K bifunctional antibody treatment at 30% tumor volume reduction. These results show significant reduction of SOX2-positive tumor cells for samples treated with H3K compared to anti-VEGF treatment. SOX2 is a stem cell factor essential for maintaining cell renewal of undifferentiated embryonic stem cells. It is re-expressed in some cancer cells and is correlated with more aggressive tumor phenotypes and drug resistance.

For FIG. 15, MDA 2131-8 tissue was stained with anti-CD34 antibody from Abcam® ab81289. FIG. 15A: treatment naïve tumor; FIG. 15B: Gemcitabine plus anti-VEGF treatment at 70% tumor volume reduction; FIG. 15C:

Gemcitabine plus H3K bifunctional antibody treatment at 70% tumor volume reduction. CD34 is a marker of hematopoietic and mesenchymal stem cells, as well as endothelial progenitor cells. These results therefore show that in tumor treated with anti-VEGF, a significant amount of CD34-positive vasculature remains, whereas in H3K-treated tumor, no intact CD34-staining vasculature was found.

For FIG. 16, MDA 2131-8 tissue was stained with anti-CD31 antibody from Invitrogen® 170700. FIG. 16A: treatment naïve tumor; FIG. 16B: Gemcitabine plus anti-VEGF treatment at 70% tumor volume reduction; FIG. 16C: Gemcitabine plus H3K bifunctional antibody treatment at 70% tumor volume reduction. CD31 is a marker of endothelial cells. These results therefore show that in tumor treated with anti-VEGF, a significant amount of CD31-positive vasculature remains, whereas in H3K-treated tumor, no intact CD31-staining vasculature was found.

Example 10. Laser-induced Choroidal Neovascularization (CNV) Study

A study was performed to determine the anti-angiogenic efficacy of the bifunctional antibody, H3K, in a neovascular age-related macular degenerative (AMD) animal model. It took advantage of fluorescein angiography to explore the lesion size and vascular leakage. The H3K drug was prepared in a 5% sucrose formulation containing 10 mM sodium phosphate, 40 mM sodium chloride, 0.03% polysorbate 20, and 5% sucrose, pH 6.2. The laser-induced CNV model is an established model for neovascular (wet) age-related macular degeneration. The study uses: Arm 1, a vehicle only control (balanced saline solution (BSS) vehicle only), and Arm 2, the H3K test agent. See Table 6, below. Arm 1: BSS; and Arm 2: H3K (67.2 mg/ml).

TABLE 6

Laser-induced CNV Study Arms.

| Arm | Description | Formulation | N | Total Protein per eye (mg)** | Concentration (mg/mL) |
|---|---|---|---|---|---|
| 1 | Vehicle | BSS | 6 | 0.000 | 0.0 |
| 2 | H3K-2 | 5% sucrose[b] | 6 | 0.336 | 67.2 |

[b]10 mM sodium phosphate, 40 mM sodium chloride, 0.03% polysorbate 20, 5% sucrose, pH 6.2;
***5 µL intravitreal injection volume.

A 22-day study was conducted in a rat model of laser-induced choroidal neovascularization (CNV) to determine the potential beneficial effects of H3K. Female Brown Norway rats (6-8 weeks of age, 130-150 g) were divided into 2 separate treatment groups as shown in Table 6. On Day 1, laser-induced lesions in the Bruch's membrane were created bilaterally using a 520 nm thermal laser to generate a total of three lesions per eye to all study animals. Animal eyes were dilated with Cyclopentolate and phenylephrine and kept in dim light for the duration of the procedure. Following observable dilation, the animals were sedated with ketamine/xylazine. Ketamine and Xylazine were administered at 60 and 9 mg/kg, respectively, via IP injection at 1 µl/g and 0.5 µl/g, respectively (body weight). The fundus of sedated animals). Laser treatments were performed using a thermal laser connected through the Micron IV custom laser attachment. A total of 3 lesions were placed per eye using a wavelength of 520 nm. The resultant fundus images were recorded and evaluated to confirm that the laser has successfully produced a bubble through the Bruch's membrane. At the completion of the procedure, the animals received the reversal agent, Yohimbine, administered via intraperitoneal injection at a concentration of 0.5 mg/kg. A subsequent subcutaneous injection of 1 ml of sterile saline was then administered, and the animal was placed on a 37° C. heating pad and monitored until full mobility was regained.

On Day 3, rats were administered a single 5 µl bilateral intravitreal (IVT) injection of BSS vehicle control (Arm 1) or H3K (Arm 2). Animals were anesthetized with ketamine/xylazine and pupils dilated with topical administration Cyclopentolate and phenylephrine. Following sedation and dilation, a total volume of 5 µl per eye was injected into the vitreous at the pars plana using a Hamilton syringe and a 32-gauge needle.

On Day 15 and Day 22, fluorescein angiography (FA) was performed. Lesion size area was determined to calculate neovascularization, and integrated density of fluorescein intensity was determined to calculate the extent of vascular leakage within the neovascular area. Animals were anesthetized with ketamine/xylazine and then received an IP injection of 10% fluorescein sodium at 1 µl/gram of body weight. Fundus images were then captured as 8-bit TIFF files using the Micron IV and exciter/barrier filters for a target wavelength of 488 nm. Standard color fundus photos were also captured for each eye. All image files were converted to bitmap and quantified using computerized image-analysis software (Photoshop™, Adobe). Lesions were individually traced free-hand in order to quantify the area in pixels and the color fundus photos were used as a reference for lesion location. Areas of avascularization in the center of lesions were excluded from area calculations. If there was hemorrhage or two lesions overlapping, these lesions were excluded from analysis. Vascular leakage was calculated by multiplying the mean fluorescein intensity by the lesion size area in pixels.

FIG. 17A and FIG. 17B show results for lesion size (neovascularization) on day 15 (FIG. 17A) and day 22 (FIG. 17B). H3K treatment reduced lesion size at day 15 and day 22 compared to the BSS vehicle control.

FIG. 18A and FIG. 18B show results for vascular leakage on day 15 (FIG. 18B) and day 22 (FIG. 18B). H3K reduced vascular leakage on day 15 and day 22.

REFERENCES

All references listed below and throughout the specification are hereby incorporated by reference in their entirety.

1. J. Zhao et al., Anti-HDGF targets cancer and cancer stromal stem cells resistant to chemotherapy, Clinical cancer research: an official journal of the American Association for Cancer Research. 19, 3567-3576 (2013), doi: 10.1158/1078-0432.CCR-12-3478.

2. J. Zhang et al., Down-regulation of hepatoma-derived growth factor inhibits anchorage-independent growth and invasion of non-small cell lung cancer cells, Cancer research. 66, 18-23 (2006), doi: 10.1158/0008-5472.CAN-04-3905.

3. C. Thirant et al., Differential proteomic analysis of human glioblastoma and neural stem cells reveals HDGF as a novel angiogenic secreted factor, Stem cells (Dayton, Ohio). 30, 845-853 (2012), doi: 10.1002/stem.1062.

4. H. Ren et al., Expression of hepatoma-derived growth factor is a strong prognostic predictor for patients with early-stage non-small-cell lung cancer, Journal of clinical oncology: official journal of the American Society of Clinical Oncology. 22, 3230-3237 (2004), doi: 10.1200/JCO.2004.02.080.

5. Iwasaki, T.; Nakagawa, K.; Nakamura, H.; Takada, Y.; Matsui, K.; Kawahara, K. (2005): Hepatoma-derived growth factor as a prognostic marker in completely resected non-small-cell lung cancer. In Oncology reports 13 (6), pp. 1075-1080.

6. H. Ren, Z. Chu, L. Mao, Antibodies targeting hepatoma-derived growth factor as a novel strategy in treating lung cancer, Molecular cancer therapeutics. 8, 1106-1112 (2009), doi: 10.1158/1535-7163.MCT-08-0779.

7. A. Zhang et al., Development and clinical evaluation of a multi-purpose mAb and a sandwich ELISA test for hepatoma-derived growth factor in lung cancer patients, Journal of immunological methods. 355, 61-67 (2010), doi: 10.1016/j.jim.2010.02.011.

8. J. V. Narron, T. D. Stoops, K. Barringhaus, M. Matsumura, A. D. Everett, Hepatoma-derived growth factor is expressed after vascular injury in the rat and stimulates smooth muscle cell migration, Pediatric research. 59, 778-783 (2006), doi: 10.1203/01.pdr.0000219299.24435.4f.

9. M. E. LeBlanc et al., The regulatory role of hepatoma-derived growth factor as an angiogenic factor in the eye, Molecular Vision. 22, 374-386 (2016).

10. C. Thirant et al., Differential proteomic analysis of human glioblastoma and neural stem cells reveals HDGF as a novel angiogenic secreted factor, Stem cells (Dayton, Ohio). 30, 845-853 (2012), doi: 10.1002/stem.1062.

11. A. D. Everett, J. V. Narron, T. Stoops, H. Nakamura, A. Tucker, Hepatoma-derived growth factor is a pulmonary endothelial cell-expressed angiogenic factor, American journal of physiology. Lung cellular and molecular physiology. 286, L1194-201 (2004), doi: 10.1152/ajplung.00427.2003.

12. B. N. Ooi et al., Hepatoma-derived growth factor and its role in keloid pathogenesis, Journal of cellular and molecular medicine. 14, 1328-1337 (2010), doi: 10.1111/j.1582-4934.2009.00779.x.

13. S. N. Greenhalgh, K. P. Conroy, N. C. Henderson, Healing scars: targeting pericytes to treat fibrosis, QJM: monthly journal of the Association of Physicians. 108, 3-7 (2015), doi: 10.1093/qjmed/hcu067

14. N. F. Voelkel, J. Gomez-Arroyo, The role of vascular endothelial growth factor in pulmonary arterial hypertension. The angiogenesis paradox, American journal of respiratory cell and molecular biology. 51, 474-484 (2014), doi: 10.1165/rcmb.2014-0045TR.

15. J. Yang et al., Hepatoma Derived Growth Factor Predicts Disease Severity and Survival in Pulmonary Artery Hypertension, American journal of respiratory and critical care medicine (2016), doi: 10.1164/rccm.201512-2498OC.

The invention claimed is:

1. A pharmaceutical composition comprising a bifunctional hepatoma-derived growth factor (HDGF)-vascular endothelial growth factor (VEGF) trapper antibody-based targeting protein and a pharmaceutically acceptable carrier, wherein the targeting protein comprises an HDGF-binding antibody binding site, and a receptor domain which specifically binds to VEGF, wherein the targeting protein comprises a heavy chain variable domain comprising the sequence of SEQ ID NO: 17 and a light chain variable domain comprising the sequence of SEQ ID NO: 18, and wherein the receptor domain is connected to the C-terminus of the heavy chain.

2. The pharmaceutical composition of claim 1, wherein the VEGF is selected from the group consisting of VEGF-A, VEGF-B, and VEGF-C.

3. The pharmaceutical composition of claim 1, wherein the targeting protein comprises a heavy chain comprising the sequence of SEQ ID NO: 19 and a light chain comprising the sequence of SEQ ID NO: 20.

4. The pharmaceutical composition of claim 1, wherein the targeting protein comprises a chain comprising the sequence of SEQ ID NO: 4 and a light chain comprising the sequence of SEQ ID NO: 20.

5. The pharmaceutical composition of claim 1, wherein the targeting protein comprises two chains comprising the sequence of SEQ ID NO: 4 and two light chains comprising the sequence of SEQ ID NO: 20.

* * * * *

SEQUENCE LISTING

```
<160> NUMBER OF SEQ ID NOS: 23

<210> SEQ ID NO 1
<211> LENGTH: 216
<212> TYPE: PRT
<213> ORGANISM: Artificial Sequence
<220> FEATURE:
<223> OTHER INFORMATION: Synthetic peptide

<400> SEQUENCE: 1

Gly Gly Gly Gly Ser Gly Gly Gly Gly Ser Arg Ser Pro Phe Ile Ala
1               5                   10                  15

Ser Val Ser Asp Gln His Gly Val Val Tyr Ile Thr Glu Asn Lys Asn
            20                  25                  30

Lys Thr Val Val Ile Pro Cys Leu Gly Ser Ile Ser Asn Leu Asn Val
        35                  40                  45

Ser Leu Cys Ala Arg Tyr Pro Glu Lys Arg Phe Val Pro Asp Gly Asn
    50                  55                  60

Arg Ile Ser Trp Asp Ser Lys Lys Gly Phe Thr Ile Pro Ser Tyr Met
65                  70                  75                  80

Ile Ser Tyr Ala Gly Met Val Phe Cys Glu Ala Lys Ile Asn Asp Glu
                85                  90                  95

Ser Tyr Gln Ser Ile Met Tyr Ile Val Val Val Gly Tyr Arg Ile
            100                 105                 110

Tyr Asp Val Val Leu Ser Pro Ser His Gly Ile Glu Leu Ser Val Gly
        115                 120                 125

Glu Lys Leu Val Leu Asn Cys Thr Ala Arg Thr Glu Leu Asn Val Gly
    130                 135                 140

Ile Asp Phe Asn Trp Glu Tyr Pro Ser Ser Lys His Gln His Lys Lys
145                 150                 155                 160

Leu Val Asn Arg Asp Leu Lys Thr Gln Ser Gly Ser Glu Met Lys Lys
                165                 170                 175

Phe Leu Ser Thr Leu Thr Ile Asp Gly Val Thr Arg Ser Asp Gln Gly
```

-continued

```
              180              185              190
Leu Tyr Thr Cys Ala Ala Ser Ser Gly Leu Met Thr Lys Lys Asn Ser
         195              200              205

Thr Phe Val Arg Val His Glu Lys
    210              215

<210> SEQ ID NO 2
<211> LENGTH: 546
<212> TYPE: PRT
<213> ORGANISM: Artificial Sequence
<220> FEATURE:
<223> OTHER INFORMATION: Synthetic peptide

<400> SEQUENCE: 2

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys Gly Gly Gly Gly Ser Gly
```

-continued

```
                325                 330                 335

Gly Gly Gly Ser Arg Ser Pro Phe Ile Ala Ser Val Ser Asp Gln His
            340                 345                 350

Gly Val Val Tyr Ile Thr Glu Asn Lys Asn Lys Thr Val Val Ile Pro
        355                 360                 365

Cys Leu Gly Ser Ile Ser Asn Leu Asn Val Ser Leu Cys Ala Arg Tyr
    370                 375                 380

Pro Glu Lys Arg Phe Val Pro Asp Gly Asn Arg Ile Ser Trp Asp Ser
385                 390                 395                 400

Lys Lys Gly Phe Thr Ile Pro Ser Tyr Met Ile Ser Tyr Ala Gly Met
                405                 410                 415

Val Phe Cys Glu Ala Lys Ile Asn Asp Glu Ser Tyr Gln Ser Ile Met
            420                 425                 430

Tyr Ile Val Val Val Val Gly Tyr Arg Ile Tyr Asp Val Val Leu Ser
            435                 440                 445

Pro Ser His Gly Ile Glu Leu Ser Val Gly Glu Lys Leu Val Leu Asn
    450                 455                 460

Cys Thr Ala Arg Thr Glu Leu Asn Val Gly Ile Asp Phe Asn Trp Glu
465                 470                 475                 480

Tyr Pro Ser Ser Lys His Gln His Lys Lys Leu Val Asn Arg Asp Leu
                485                 490                 495

Lys Thr Gln Ser Gly Ser Glu Met Lys Lys Phe Leu Ser Thr Leu Thr
                500                 505                 510

Ile Asp Gly Val Thr Arg Ser Asp Gln Gly Leu Tyr Thr Cys Ala Ala
            515                 520                 525

Ser Ser Gly Leu Met Thr Lys Lys Asn Ser Thr Phe Val Arg Val His
    530                 535                 540

Glu Lys
545

<210> SEQ ID NO 3
<211> LENGTH: 686
<212> TYPE: PRT
<213> ORGANISM: Artificial Sequence
<220> FEATURE:
<223> OTHER INFORMATION: Synthetic peptide

<400> SEQUENCE: 3

Met Val Ser Thr Ala Gln Phe Leu Gly Leu Leu Leu Leu Cys Phe Gln
1               5                   10                  15

Gly Thr Arg Cys Gln Ile Thr Leu Lys Gln Ser Gly Pro Gly Ile Val
            20                  25                  30

Gln Pro Ser Gln Pro Val Arg Leu Thr Cys Thr Phe Ser Gly Phe Ser
        35                  40                  45

Leu Ser Thr Ser Gly Ile Gly Val Ala Trp Ile Arg Gln Pro Ser Gly
    50                  55                  60

Lys Gly Leu Glu Trp Leu Ala Thr Ile Trp Trp Asp Asp Asp Asn Arg
65                  70                  75                  80

Tyr Asn Pro Ser Leu Lys Ser Arg Leu Ala Val Ser Lys Asp Thr Ser
                85                  90                  95

Asn Asn Gln Ala Phe Leu Asn Ile Ile Thr Val Glu Thr Ala Asp Thr
                100                 105                 110

Ala Ile Tyr Tyr Cys Ala Gln Ile Tyr Asp Tyr Ala Val Gly Phe Ala
            115                 120                 125

Tyr Trp Gly Gln Gly Thr Leu Val Thr Val Ser Ser Ala Ser Thr Lys
```

-continued

```
        130                135                140
Gly Pro Ser Val Phe Pro Leu Ala Pro Ser Ser Lys Ser Thr Ser Gly
145                 150                155                160

Gly Thr Ala Ala Leu Gly Cys Leu Val Lys Asp Tyr Phe Pro Glu Pro
                165                170                175

Val Thr Val Ser Trp Asn Ser Gly Ala Leu Thr Ser Gly Val His Thr
                180                185                190

Phe Pro Ala Val Leu Gln Ser Ser Gly Leu Tyr Ser Leu Ser Ser Val
                195                200                205

Val Thr Val Pro Ser Ser Ser Leu Gly Thr Gln Thr Tyr Ile Cys Asn
            210                215                220

Val Asn His Lys Pro Ser Asn Thr Lys Val Asp Lys Lys Val Glu Pro
225                230                235                240

Lys Ser Cys Asp Lys Thr His Thr Cys Pro Pro Cys Pro Ala Pro Glu
                245                250                255

Leu Leu Gly Gly Pro Ser Val Phe Leu Phe Pro Pro Lys Pro Lys Asp
                260                265                270

Thr Leu Met Ile Ser Arg Thr Pro Glu Val Thr Cys Val Val Val Asp
                275                280                285

Val Ser His Glu Asp Pro Glu Val Lys Phe Asn Trp Tyr Val Asp Gly
            290                295                300

Val Glu Val His Asn Ala Lys Thr Lys Pro Arg Glu Glu Gln Tyr Asn
305                310                315                320

Ser Thr Tyr Arg Val Val Ser Val Leu Thr Val Leu His Gln Asp Trp
                325                330                335

Leu Asn Gly Lys Glu Tyr Lys Cys Lys Val Ser Asn Lys Ala Leu Pro
                340                345                350

Ala Pro Ile Glu Lys Thr Ile Ser Lys Ala Lys Gly Gln Pro Arg Glu
                355                360                365

Pro Gln Val Tyr Thr Leu Pro Pro Ser Arg Asp Glu Leu Thr Lys Asn
            370                375                380

Gln Val Ser Leu Thr Cys Leu Val Lys Gly Phe Tyr Pro Ser Asp Ile
385                390                395                400

Ala Val Glu Trp Glu Ser Asn Gly Gln Pro Glu Asn Asn Tyr Lys Thr
                405                410                415

Thr Pro Pro Val Leu Asp Ser Asp Gly Ser Phe Phe Leu Tyr Ser Lys
                420                425                430

Leu Thr Val Asp Lys Ser Arg Trp Gln Gln Gly Asn Val Phe Ser Cys
                435                440                445

Ser Val Met His Glu Ala Leu His Asn His Tyr Thr Gln Lys Ser Leu
            450                455                460

Ser Leu Ser Pro Gly Lys Gly Gly Gly Gly Ser Gly Gly Gly Gly Ser
465                470                475                480

Arg Ser Pro Phe Ile Ala Ser Val Ser Asp Gln His Gly Val Val Tyr
                485                490                495

Ile Thr Glu Asn Lys Asn Lys Thr Val Val Ile Pro Cys Leu Gly Ser
                500                505                510

Ile Ser Asn Leu Asn Val Ser Leu Cys Ala Arg Tyr Pro Glu Lys Arg
                515                520                525

Phe Val Pro Asp Gly Asn Arg Ile Ser Trp Asp Ser Lys Lys Gly Phe
            530                535                540

Thr Ile Pro Ser Tyr Met Ile Ser Tyr Ala Gly Met Val Phe Cys Glu
545                550                555                560
```

-continued

```
Ala Lys Ile Asn Asp Glu Ser Tyr Gln Ser Ile Met Tyr Ile Val Val
            565                 570                 575

Val Val Gly Tyr Arg Ile Tyr Asp Val Val Leu Ser Pro Ser His Gly
            580                 585                 590

Ile Glu Leu Ser Val Gly Glu Lys Leu Val Leu Asn Cys Thr Ala Arg
            595                 600                 605

Thr Glu Leu Asn Val Gly Ile Asp Phe Asn Trp Glu Tyr Pro Ser Ser
            610                 615                 620

Lys His Gln His Lys Lys Leu Val Asn Arg Asp Leu Lys Thr Gln Ser
625                 630                 635                 640

Gly Ser Glu Met Lys Lys Phe Leu Ser Thr Leu Thr Ile Asp Gly Val
            645                 650                 655

Thr Arg Ser Asp Gln Gly Leu Tyr Thr Cys Ala Ala Ser Ser Gly Leu
            660                 665                 670

Met Thr Lys Lys Asn Ser Thr Phe Val Arg Val His Glu Lys
            675                 680                 685

<210> SEQ ID NO 4
<211> LENGTH: 666
<212> TYPE: PRT
<213> ORGANISM: Artificial Sequence
<220> FEATURE:
<223> OTHER INFORMATION: Synthetic peptide

<400> SEQUENCE: 4

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Ile Gly Val Ala Trp Ile Arg Gln Pro Pro Gly Lys Ala Leu Glu
            35                  40                  45

Trp Leu Ala Thr Ile Trp Trp Asp Asp Asp Asn Arg Tyr Asn Pro Ser
            50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Tyr Asp Tyr Ala Val Gly Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys Gly Gly Gly Gly Ser Gly Gly Gly Gly Ser Arg Ser Pro Phe
    450             455             460

Ile Ala Ser Val Ser Asp Gln His Gly Val Val Tyr Ile Thr Glu Asn
465             470             475             480

Lys Asn Lys Thr Val Val Ile Pro Cys Leu Gly Ser Ile Ser Asn Leu
            485             490             495

Asn Val Ser Leu Cys Ala Arg Tyr Pro Glu Lys Arg Phe Val Pro Asp
            500             505             510

Gly Asn Arg Ile Ser Trp Asp Ser Lys Lys Gly Phe Thr Ile Pro Ser
            515             520             525

Tyr Met Ile Ser Tyr Ala Gly Met Val Phe Cys Glu Ala Lys Ile Asn
    530             535             540

Asp Glu Ser Tyr Gln Ser Ile Met Tyr Ile Val Val Val Gly Tyr
545             550             555             560

Arg Ile Tyr Asp Val Val Leu Ser Pro Ser His Gly Ile Glu Leu Ser
            565             570             575

Val Gly Glu Lys Leu Val Leu Asn Cys Thr Ala Arg Thr Glu Leu Asn
            580             585             590

Val Gly Ile Asp Phe Asn Trp Glu Tyr Pro Ser Ser Lys His Gln His
            595             600             605

Lys Lys Leu Val Asn Arg Asp Leu Lys Thr Gln Ser Gly Ser Glu Met
    610             615             620

Lys Lys Phe Leu Ser Thr Leu Thr Ile Asp Gly Val Thr Arg Ser Asp
625             630             635             640

Gln Gly Leu Tyr Thr Cys Ala Ala Ser Ser Gly Leu Met Thr Lys Lys
            645             650             655
```

Asn Ser Thr Phe Val Arg Val His Glu Lys
        660                665

<210> SEQ ID NO 5
<211> LENGTH: 127
<212> TYPE: PRT
<213> ORGANISM: Artificial Sequence
<220> FEATURE:
<223> OTHER INFORMATION: Synthetic peptide

<400> SEQUENCE: 5

Gly Gly Gly Gly Ser Gly Gly Gly Ser Gly Ala Val Lys Phe Pro
1            5                10                15

Gln Leu Cys Lys Phe Cys Asp Val Arg Phe Ser Thr Cys Asp Asn Gln
        20              25              30

Lys Ser Cys Met Ser Asn Cys Ser Ile Thr Ser Ile Cys Glu Lys Pro
        35              40              45

Gln Glu Val Cys Val Ala Val Trp Arg Lys Asn Asp Glu Asn Ile Thr
    50              55              60

Leu Glu Thr Val Cys His Asp Pro Lys Leu Pro Tyr His Asp Phe Ile
65               70            75            80

Leu Glu Asp Ala Ala Ser Pro Lys Cys Ile Met Lys Glu Lys Lys Lys
        85              90              95

Pro Gly Glu Thr Phe Phe Met Cys Ser Cys Ser Ser Asp Glu Cys Asn
           100            105           110

Asp Asn Ile Ile Phe Ser Glu Glu Tyr Asn Thr Ser Asn Pro Asp
        115              120           125

<210> SEQ ID NO 6
<211> LENGTH: 457
<212> TYPE: PRT
<213> ORGANISM: Artificial Sequence
<220> FEATURE:
<223> OTHER INFORMATION: Synthetic peptide

<400> SEQUENCE: 6

Ala Ser Thr Lys Gly Pro Ser Val Phe Pro Leu Ala Pro Ser Ser Lys
1            5                10                15

Ser Thr Ser Gly Gly Thr Ala Ala Leu Gly Cys Leu Val Lys Asp Tyr
        20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65               70           75           80

Tyr Ile Cys Asn Val Asn His Lys Pro Ser Asn Thr Lys Val Asp Lys
        85              90              95

Lys Val Glu Pro Lys Ser Cys Asp Lys Thr His Thr Cys Pro Pro Cys
           100            105           110

Pro Ala Pro Glu Leu Leu Gly Gly Pro Ser Val Phe Leu Phe Pro Pro
        115              120           125

Lys Pro Lys Asp Thr Leu Met Ile Ser Arg Thr Pro Glu Val Thr Cys
        130              135           140

Val Val Val Asp Val Ser His Glu Asp Pro Glu Val Lys Phe Asn Trp
145             150          155           160

Tyr Val Asp Gly Val Glu Val His Asn Ala Lys Thr Lys Pro Arg Glu
           165           170          175

-continued

```
Glu Gln Tyr Asn Ser Thr Tyr Arg Val Val Ser Val Leu Thr Val Leu
        180                 185             190

His Gln Asp Trp Leu Asn Gly Lys Glu Tyr Lys Cys Lys Val Ser Asn
        195                 200             205

Lys Ala Leu Pro Ala Pro Ile Glu Lys Thr Ile Ser Lys Ala Lys Gly
        210                 215             220

Gln Pro Arg Glu Pro Gln Val Tyr Thr Leu Pro Pro Ser Arg Asp Glu
225                 230             235                 240

Leu Thr Lys Asn Gln Val Ser Leu Thr Cys Leu Val Lys Gly Phe Tyr
                245             250                 255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315                 320

Gln Lys Ser Leu Ser Leu Ser Pro Gly Lys Gly Gly Gly Gly Ser Gly
                325             330                 335

Gly Gly Gly Ser Gly Ala Val Lys Phe Pro Gln Leu Cys Lys Phe Cys
            340             345             350

Asp Val Arg Phe Ser Thr Cys Asp Asn Gln Lys Ser Cys Met Ser Asn
            355             360             365

Cys Ser Ile Thr Ser Ile Cys Glu Lys Pro Gln Glu Val Cys Val Ala
        370             375             380

Val Trp Arg Lys Asn Asp Glu Asn Ile Thr Leu Glu Thr Val Cys His
385             390             395                 400

Asp Pro Lys Leu Pro Tyr His Asp Phe Ile Leu Glu Asp Ala Ala Ser
                405             410             415

Pro Lys Cys Ile Met Lys Glu Lys Lys Lys Pro Gly Glu Thr Phe Phe
            420             425             430

Met Cys Ser Cys Ser Ser Asp Glu Cys Asn Asp Asn Ile Ile Phe Ser
            435             440             445

Glu Glu Tyr Asn Thr Ser Asn Pro Asp
    450             455
```

```
<210> SEQ ID NO 7
<211> LENGTH: 597
<212> TYPE: PRT
<213> ORGANISM: Artificial Sequence
<220> FEATURE:
<223> OTHER INFORMATION: Synthetic peptide

<400> SEQUENCE: 7

Met Val Ser Thr Ala Gln Phe Leu Gly Leu Leu Leu Leu Cys Phe Gln
1               5                   10                  15

Gly Thr Arg Cys Gln Ile Thr Leu Lys Gln Ser Gly Pro Gly Ile Val
            20                  25                  30

Gln Pro Ser Gln Pro Val Arg Leu Thr Cys Thr Phe Ser Gly Phe Ser
            35                  40                  45

Leu Ser Thr Ser Gly Ile Gly Val Ala Trp Ile Arg Gln Pro Ser Gly
        50                  55                  60

Lys Gly Leu Glu Trp Leu Ala Thr Ile Trp Trp Asp Asp Asp Asn Arg
65                  70                  75                  80
```

-continued

```
Tyr Asn Pro Ser Leu Lys Ser Arg Leu Ala Val Ser Lys Asp Thr Ser
            85              90              95

Asn Asn Gln Ala Phe Leu Asn Ile Ile Thr Val Glu Thr Ala Asp Thr
            100             105             110

Ala Ile Tyr Tyr Cys Ala Gln Ile Tyr Asp Tyr Ala Val Gly Phe Ala
            115             120             125

Tyr Trp Gly Gln Gly Thr Leu Val Thr Val Ser Ser Ala Ser Thr Lys
    130             135             140

Gly Pro Ser Val Phe Pro Leu Ala Pro Ser Ser Lys Ser Thr Ser Gly
145             150             155             160

Gly Thr Ala Ala Leu Gly Cys Leu Val Lys Asp Tyr Phe Pro Glu Pro
                165             170             175

Val Thr Val Ser Trp Asn Ser Gly Ala Leu Thr Ser Gly Val His Thr
                180             185             190

Phe Pro Ala Val Leu Gln Ser Ser Gly Leu Tyr Ser Leu Ser Ser Val
            195             200             205

Val Thr Val Pro Ser Ser Ser Leu Gly Thr Gln Thr Tyr Ile Cys Asn
    210             215             220

Val Asn His Lys Pro Ser Asn Thr Lys Val Asp Lys Lys Val Glu Pro
225             230             235             240

Lys Ser Cys Asp Lys Thr His Thr Cys Pro Pro Cys Pro Ala Pro Glu
                245             250             255

Leu Leu Gly Gly Pro Ser Val Phe Leu Phe Pro Pro Lys Pro Lys Asp
                260             265             270

Thr Leu Met Ile Ser Arg Thr Pro Glu Val Thr Cys Val Val Val Asp
                275             280             285

Val Ser His Glu Asp Pro Glu Val Lys Phe Asn Trp Tyr Val Asp Gly
    290             295             300

Val Glu Val His Asn Ala Lys Thr Lys Pro Arg Glu Glu Gln Tyr Asn
305             310             315             320

Ser Thr Tyr Arg Val Val Ser Val Leu Thr Val Leu His Gln Asp Trp
                325             330             335

Leu Asn Gly Lys Glu Tyr Lys Cys Lys Val Ser Asn Lys Ala Leu Pro
                340             345             350

Ala Pro Ile Glu Lys Thr Ile Ser Lys Ala Lys Gly Gln Pro Arg Glu
                355             360             365

Pro Gln Val Tyr Thr Leu Pro Pro Ser Arg Asp Glu Leu Thr Lys Asn
    370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
                405             410             415

Thr Pro Pro Val Leu Asp Ser Asp Gly Ser Phe Phe Leu Tyr Ser Lys
                420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
    450             455             460

Ser Leu Ser Pro Gly Lys Gly Gly Gly Gly Ser Gly Gly Gly Gly Ser
465             470             475             480

Gly Ala Val Lys Phe Pro Gln Leu Cys Lys Phe Cys Asp Val Arg Phe
                485             490             495
```

```
Ser Thr Cys Asp Asn Gln Lys Ser Cys Met Ser Asn Cys Ser Ile Thr
            500                 505                 510

Ser Ile Cys Glu Lys Pro Gln Glu Val Cys Val Ala Val Trp Arg Lys
            515                 520                 525

Asn Asp Glu Asn Ile Thr Leu Glu Thr Val Cys His Asp Pro Lys Leu
            530                 535                 540

Pro Tyr His Asp Phe Ile Leu Glu Asp Ala Ala Ser Pro Lys Cys Ile
545                 550                 555                 560

Met Lys Glu Lys Lys Lys Pro Gly Glu Thr Phe Phe Met Cys Ser Cys
                565                 570                 575

Ser Ser Asp Glu Cys Asn Asp Asn Ile Ile Phe Ser Glu Glu Tyr Asn
            580                 585                 590

Thr Ser Asn Pro Asp
            595
```

```
<210> SEQ ID NO 8
<211> LENGTH: 577
<212> TYPE: PRT
<213> ORGANISM: Artificial Sequence
<220> FEATURE:
<223> OTHER INFORMATION: Synthetic peptide

<400> SEQUENCE: 8

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Ile Gly Val Ala Trp Ile Arg Gln Pro Pro Gly Lys Ala Leu Glu
            35                  40                  45

Trp Leu Ala Thr Ile Trp Trp Asp Asp Asp Asn Arg Tyr Asn Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Tyr Asp Tyr Ala Val Gly Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gly Ala Val Lys
            450                 455                 460

Phe Pro Gln Leu Cys Lys Phe Cys Asp Val Arg Phe Ser Thr Cys Asp
465                 470                 475                 480

Asn Gln Lys Ser Cys Met Ser Asn Cys Ser Ile Thr Ser Ile Cys Glu
            485                 490                 495

Lys Pro Gln Glu Val Cys Val Ala Val Trp Arg Lys Asn Asp Glu Asn
            500                 505                 510

Ile Thr Leu Glu Thr Val Cys His Asp Pro Lys Leu Pro Tyr His Asp
            515                 520                 525

Phe Ile Leu Glu Asp Ala Ala Ser Pro Lys Cys Ile Met Lys Glu Lys
            530                 535                 540

Lys Lys Pro Gly Glu Thr Phe Phe Met Cys Ser Cys Ser Ser Asp Glu
545                 550                 555                 560

Cys Asn Asp Asn Ile Ile Phe Ser Glu Glu Tyr Asn Thr Ser Asn Pro
            565                 570                 575

Asp

<210> SEQ ID NO 9
<211> LENGTH: 159
<212> TYPE: PRT
<213> ORGANISM: Artificial Sequence
<220> FEATURE:
<223> OTHER INFORMATION: Synthetic peptide: H3HD4 (H3 heavy chain)

<400> SEQUENCE: 9

Met Gly Arg Leu Thr Ser Ser Phe Leu Leu Leu Val Val Pro Ile Tyr
1               5                   10                  15

Val Leu Ser Gln Ile Thr Leu Lys Gln Ser Gly Pro Gly Ile Val Gln
            20                  25                  30

Pro Ser Gln Pro Val Arg Leu Thr Cys Thr Phe Ser Gly Phe Ser Leu

-continued

```
              35              40              45

Ser Thr Ser Gly Ile Gly Val Ala Trp Ile Arg Gln Pro Ser Gly Lys
    50              55              60

Gly Leu Glu Trp Leu Ala Thr Ile Trp Trp Asp Asp Asp Asn Arg Tyr
65              70              75              80

Asn Pro Ser Leu Lys Ser Arg Leu Ala Val Ser Lys Asp Thr Ser Asn
                85              90              95

Asn Gln Ala Phe Leu Asn Ile Ile Thr Val Glu Thr Ala Asp Thr Ala
            100             105             110

Ile Tyr Tyr Cys Ala Gln Ile Tyr Asp Tyr Ala Val Gly Phe Ala Tyr
            115             120             125

Trp Gly Gln Gly Thr Leu Val Thr Val Ser Ala Ala Lys Thr Thr Pro
    130             135             140

Pro Ser Val Tyr Pro Leu Ala Pro Gly Ser Leu Gly Arg Ala Asn
145             150             155
```

```
<210> SEQ ID NO 10
<211> LENGTH: 148
<212> TYPE: PRT
<213> ORGANISM: Artificial Sequence
<220> FEATURE:
<223> OTHER INFORMATION: Synthetic peptide: H3LF2 (H3 light chain)

<400> SEQUENCE: 10

Met Val Ser Thr Ala Gln Phe Leu Gly Leu Leu Leu Leu Cys Phe Gln
1               5               10              15

Gly Thr Arg Cys Asp Ile Gln Met Thr Gln Thr Thr Ser Ser Leu Ser
            20              25              30

Ala Ser Leu Gly Asp Arg Val Thr Ile Ser Cys Arg Ala Ser Gln Asp
        35              40              45

Ile Ser Asn Tyr Leu Asn Trp Tyr Gln Gln Lys Pro Asp Gly Thr Val
    50              55              60

Lys Leu Leu Ile Tyr Tyr Thr Ser Arg Leu His Ser Gly Val Pro Ser
65              70              75              80

Arg Phe Ser Gly Ser Gly Ser Gly Thr Asp Tyr Ser Leu Thr Ile Ser
                85              90              95

Asn Leu Glu Pro Asp Asp Ile Ala Thr Tyr Tyr Cys Gln Gln Tyr Gly
            100             105             110

Lys Leu Trp Thr Phe Gly Gly Gly Thr Lys Leu Glu Ile Lys Arg Ala
            115             120             125

Asp Ala Ala Pro Thr Val Ser Ile Phe Pro Pro Ser Ser Lys Leu Gly
        130             135             140

Lys Gly Glu Phe
145
```

```
<210> SEQ ID NO 11
<211> LENGTH: 161
<212> TYPE: PRT
<213> ORGANISM: Artificial Sequence
<220> FEATURE:
<223> OTHER INFORMATION: Synthetic peptide: C1HA5 (C1 heavy chain)

<400> SEQUENCE: 11

Met Asn Leu Gly Leu Ser Trp Ile Phe Phe Ala Val Phe Tyr Gln Gly
1               5               10              15

Val His Cys Glu Val Gln Leu Val Glu Ser Gly Gly Arg Leu Val Gln
            20              25              30
```

-continued

```
Pro Lys Gly Ser Leu Lys Leu Ser Cys Ala Ala Ser Gly Phe Thr Phe
        35              40              45

Asn Thr Tyr Ala Met Tyr Trp Ile Arg Gln Ala Pro Gly Lys Gly Leu
        50              55              60

Glu Trp Val Ala Arg Ile Arg Ser Lys Ser Tyr Asn Tyr Ala Thr Tyr
65              70              75              80

Tyr Ala Asp Ser Val Lys Asp Arg Phe Thr Ile Ser Arg Asp Asp Ser
                85              90              95

Gln Ser Met Leu Tyr Leu Gln Met Asn Asn Leu Lys Thr Ala Asp Thr
                100             105             110

Ala Met Tyr Tyr Cys Val Ser Glu Gly Phe Trp Gly Gln Gly Thr Ser
            115             120             125

Val Thr Val Ser Ser Ala Lys Thr Thr Pro Pro Ser Val Tyr Pro Leu
        130             135             140

Val Pro Gly Ser Leu Gly Arg Ala Asn Ser Ala Asp Ile His His Thr
145             150             155             160

Gly
```

```
<210> SEQ ID NO 12
<211> LENGTH: 153
<212> TYPE: PRT
<213> ORGANISM: Artificial Sequence
<220> FEATURE:
<223> OTHER INFORMATION: Synthetic peptide: C1LG1 (C1 light chain)

<400> SEQUENCE: 12
```

```
Met Lys Leu Pro Val Arg Leu Leu Val Leu Met Phe Trp Ile Pro Ala
1               5               10              15

Ser Ser Ser Asp Val Leu Met Thr Gln Thr Pro Leu Ser Leu Pro Val
            20              25              30

Ser Leu Gly Asp Gln Ala Ser Ile Ser Cys Arg Ser Ser Gln Ser Ile
        35              40              45

Val His Ser Ser Gly Asn Thr Tyr Leu Glu Trp Tyr Leu Gln Lys Pro
    50              55              60

Gly Gln Ser Pro Lys Leu Leu Ile Tyr Lys Val Ser Asn Arg Phe Ser
65              70              75              80

Gly Val Pro Asp Arg Phe Ser Gly Ser Gly Ser Gly Thr Asp Phe Thr
                85              90              95

Leu Lys Ile Ser Arg Val Glu Ala Glu Asp Leu Gly Val Tyr Tyr Cys
            100             105             110

Phe Gln Gly Ser His Val Pro Trp Thr Phe Gly Gly Gly Thr Lys Leu
        115             120             125

Glu Ile Lys Arg Ala Asp Ala Ala Pro Thr Val Ser Ile Phe Pro Pro
    130             135             140

Ser Ser Lys Leu Gly Lys Gly Glu Phe
145             150
```

```
<210> SEQ ID NO 13
<211> LENGTH: 159
<212> TYPE: PRT
<213> ORGANISM: Artificial Sequence
<220> FEATURE:
<223> OTHER INFORMATION: Synthetic peptide: C4HD1 (C4 heavy chain)

<400> SEQUENCE: 13
```

```
Met Asp Arg Leu Thr Ser Ser Phe Leu Leu Leu Ile Val Pro Ala Tyr
1               5               10              15
```

-continued

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
        50                  55                  60

Gly Leu Glu Trp Leu Ala His Ile Trp Trp Asp Asp Val Lys Arg Phe
65                  70                  75                  80

Asn Pro Asp Leu Lys Ser Arg Leu Thr Ile Ser Lys Asp Thr Ser Ser
                85                  90                  95

Ala Gln Val Phe Leu Lys Ile Ala Ser Val Asp Thr Ala Asp Thr Ala
            100                 105                 110

Thr Tyr Tyr Cys Thr Arg Ile Glu Asp Tyr Asp Gly Ala Leu Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Leu Gly Arg Ala Asn
145                 150                 155

<210> SEQ ID NO 14
<211> LENGTH: 154
<212> TYPE: PRT
<213> ORGANISM: Artificial Sequence
<220> FEATURE:
<223> OTHER INFORMATION: Synthetic peptide: C4LA1 (C4 light chain)

<400> SEQUENCE: 14

Met Glu Ser Gln Ser Gln Val Phe Leu Ser Leu Leu Leu Trp Val Ser
1                   5                   10                  15

Gly Thr Cys Gly Asn Ile Met Met Thr Gln Ser Pro Ser Ser Leu Ala
            20                  25                  30

Val Ser Thr Gly Glu Met Val Thr Met Ser Cys Lys Ser Ser Gln Ser
        35                  40                  45

Val Leu Tyr Ser Ser Asn Gln Lys Asn Tyr Leu Ala Trp Phe Gln Gln
    50                  55                  60

Thr Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Asn Val Gln Ala Ala Asp Leu Ala Val Tyr
            100                 105                 110

Tyr Cys His Gln Tyr Leu Ser Ser Trp Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Lys Leu Gly Lys Gly Glu Phe
145                 150

<210> SEQ ID NO 15
<211> LENGTH: 157
<212> TYPE: PRT
<213> ORGANISM: Artificial Sequence
<220> FEATURE:
<223> OTHER INFORMATION: Synthetic peptide: L5HB-1 (L5 heavy chain)

<400> SEQUENCE: 15

Met Lys Trp Ser Trp Val Phe Leu Phe Leu Val Ala Thr Ala Thr Gly
1                   5                   10                  15

-continued

```
Val Arg Ser Gln Val Gln Leu Gln Gln Pro Gly Ala Glu Leu Val Lys
            20              25              30

Pro Gly Ala Ser Val Lys Leu Ser Cys Lys Ala Ser Gly Tyr Thr Phe
            35              40              45

Thr Ser Tyr Trp Ile His Trp Val Lys Gln Arg Pro Gly Gln Gly Leu
        50              55              60

Glu Trp Ile Gly Asn Ile Asn Pro Asn Ser Gly Ser Thr Asp Asn Asn
65                  70              75              80

Glu Lys Phe Thr Ser Lys Ala Thr Leu Thr Val Asp Thr Ser Ser Ser
            85              90              95

Thr Ala Tyr Met Gln Leu Ser Ser Leu Thr Ser Glu Asp Ser Ala Val
            100             105             110

Tyr Tyr Cys Thr Thr Leu Leu Gly Arg Thr Gly Phe Ala Tyr Trp Gly
        115             120             125

Gln Gly Thr Leu Val Thr Val Ser Ala Ala Lys Thr Thr Pro Pro Ser
    130             135             140

Val Tyr Pro Leu Ala Pro Gly Ser Leu Gly Arg Ala Asn
145             150             155
```

```
<210> SEQ ID NO 16
<211> LENGTH: 149
<212> TYPE: PRT
<213> ORGANISM: Artificial Sequence
<220> FEATURE:
<223> OTHER INFORMATION: Synthetic peptide: L5LD1 (L5 light chain)

<400> SEQUENCE: 16
```

```
Met Arg Ala Pro Ala Gln Ile Leu Gly Ile Leu Leu Leu Trp Phe Pro
1               5               10              15

Gly Ile Lys Cys Asp Ile Lys Met Thr Gln Ser Pro Ser Ser Met Tyr
            20              25              30

Ala Ser Leu Gly Glu Arg Val Thr Ile Thr Cys Lys Ala Ser Gln Asp
        35              40              45

Ile Asn Ser Tyr Leu Ser Trp Phe Gln Gln Lys Pro Gly Lys Ser Pro
    50              55              60

Lys Thr Leu Ile Tyr Arg Ala Asn Arg Leu Leu Asp Gly Val Pro Ser
65                  70              75              80

Arg Phe Ser Gly Ser Gly Ser Gly Gln Asp Tyr Ser Leu Thr Ile Ser
            85              90              95

Ser Leu Glu Tyr Glu Asp Leu Gly Ile Tyr Tyr Cys Leu Gln Tyr Asp
            100             105             110

Glu Phe Pro Leu Thr Phe Gly Ala Gly Thr Lys Leu Glu Leu Lys Arg
        115             120             125

Ala Asp Ala Ala Pro Thr Val Ser Ile Phe Pro Pro Ser Ser Lys Leu
    130             135             140

Gly Lys Gly Glu Phe
145
```

```
<210> SEQ ID NO 17
<211> LENGTH: 120
<212> TYPE: PRT
<213> ORGANISM: Artificial Sequence
<220> FEATURE:
<223> OTHER INFORMATION: Synthetic peptide: Humanized H3 heavy chain
      variable region, mature sequence

<400> SEQUENCE: 17
```

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Ile Gly Val Ala Trp Ile Arg Gln Pro Pro Gly Lys Ala Leu Glu
        35                  40                  45

Trp Leu Ala Thr Ile Trp Trp Asp Asp Asp Asn Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Tyr Asp Tyr Ala Val Gly Phe Ala Tyr Trp Gly Gln
                100                 105                 110

Gly Thr Leu Val Thr Val Ser Ser
            115                 120
```

<210> SEQ ID NO 18
<211> LENGTH: 104
<212> TYPE: PRT
<213> ORGANISM: Artificial Sequence
<220> FEATURE:
<223> OTHER INFORMATION: Synthetic peptide: Humanized H3 light chain
      variable region, mature sequence

<400> SEQUENCE: 18

```
Asp Ile Gln Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Ser Leu Gln Pro
65                  70                  75                  80

Glu Asp Ile Ala Thr Tyr Tyr Cys Gln Gln Tyr Gly Lys Leu Trp Thr
                85                  90                  95

Phe Gly Gln Gly Thr Lys Leu Glu
            100
```

<210> SEQ ID NO 19
<211> LENGTH: 450
<212> TYPE: PRT
<213> ORGANISM: Artificial Sequence
<220> FEATURE:
<223> OTHER INFORMATION: Synthetic peptide: Humanized H3 heavy chain,
      mature sequence

<400> SEQUENCE: 19

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Ile Gly Val Ala Trp Ile Arg Gln Pro Pro Gly Lys Ala Leu Glu
        35                  40                  45

Trp Leu Ala Thr Ile Trp Trp Asp Asp Asp Asn Arg Tyr Asn Pro Ser
    50                  55                  60
```

-continued

```
Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Tyr Asp Tyr Ala Val Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

```
<210> SEQ ID NO 20
<211> LENGTH: 213
<212> TYPE: PRT
```

<213> ORGANISM: Artificial Sequence
<220> FEATURE:
<223> OTHER INFORMATION: Synthetic peptide: Humanized H3 light chain,
      mature sequence

<400> SEQUENCE: 20

Asp Ile Gln Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Ser Leu Gln Pro
65                  70                  75                  80

Glu Asp Ile Ala Thr Tyr Tyr Cys Gln Gln Tyr Gly Lys Leu Trp Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 21
<211> LENGTH: 470
<212> TYPE: PRT
<213> ORGANISM: Artificial Sequence
<220> FEATURE:
<223> OTHER INFORMATION: Synthetic peptide: Heavy chain

<400> SEQUENCE: 21

Met Val Ser Thr Ala Gln Phe Leu Gly Leu Leu Leu Leu Cys Phe Gln
1               5                   10                  15

Gly Thr Arg Cys Gln Ile Thr Leu Lys Gln Ser Gly Pro Gly Ile Val
                20                  25                  30

Gln Pro Ser Gln Pro Val Arg Leu Thr Cys Thr Phe Ser Gly Phe Ser
            35                  40                  45

Leu Ser Thr Ser Gly Ile Gly Val Ala Trp Ile Arg Gln Pro Ser Gly
        50                  55                  60

Lys Gly Leu Glu Trp Leu Ala Thr Ile Trp Trp Asp Asp Asp Asn Arg
65                  70                  75                  80

Tyr Asn Pro Ser Leu Lys Ser Arg Leu Ala Val Ser Lys Asp Thr Ser
                85                  90                  95

Asn Asn Gln Ala Phe Leu Asn Ile Ile Thr Val Glu Thr Ala Asp Thr
            100                 105                 110

```
Ala Ile Tyr Tyr Cys Ala Gln Ile Tyr Asp Tyr Ala Val Gly Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

```
<210> SEQ ID NO 22
<211> LENGTH: 233
<212> TYPE: PRT
<213> ORGANISM: Artificial Sequence
<220> FEATURE:
<223> OTHER INFORMATION: Synthetic peptide: Light chain

<400> SEQUENCE: 22
```

-continued

```
Met Val Ser Thr Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Pro Asp Asp Ile Ala Thr Tyr Tyr Cys Gln Gln Tyr Gly
            100                 105                 110

Lys Leu Trp Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 23
<211> LENGTH: 10
<212> TYPE: PRT
<213> ORGANISM: Artificial Sequence
<220> FEATURE:
<223> OTHER INFORMATION: Synthetic linker

<400> SEQUENCE: 23

Gly Gly Gly Gly Ser Gly Gly Gly Gly Ser
1               5                   10
```